US007498416B2

(12) United States Patent
Yayon et al.

(10) Patent No.: US 7,498,416 B2
(45) Date of Patent: Mar. 3, 2009

(54) ANTIBODIES THAT BLOCK RECEPTOR PROTEIN TYROSINE KINASE ACTIVATION, METHODS OF SCREENING FOR AND USES THEREOF

(75) Inventors: Avner Yayon, Moshav Sitria (IL); Eran Rom, Rehovot (IL); Elisabeth Thomassen-Wolf, Martinsried (DE); Eric Borges, Krailing (DE)

(73) Assignee: Fibron Limited, Ness-Ziona (IL)

( * ) Notice: Subject to any disclaimer, the term of this patent is extended or adjusted under 35 U.S.C. 154(b) by 537 days.

(21) Appl. No.: 10/734,661

(22) Filed: Dec. 15, 2003

(65) Prior Publication Data

US 2005/0147612 A1   Jul. 7, 2005

Related U.S. Application Data

(63) Continuation of application No. PCT/IL02/00494, filed on Jun. 20, 2002.

(60) Provisional application No. 60/299,187, filed on Jun. 20, 2001.

(51) Int. Cl.
*C07K 16/00* (2006.01)

(52) U.S. Cl. ............... 530/387.1; 530/350; 530/387.3; 530/388.22

(58) Field of Classification Search ............... 530/350, 530/387.1, 387.3, 388.22; 424/141.1
See application file for complete search history.

(56) References Cited

U.S. PATENT DOCUMENTS

| 4,376,110 | A | 3/1983 | David et al. ..................... 435/5 |
|---|---|---|---|
| 4,816,567 | A | 3/1989 | Cabilly et al. ............ 530/387.3 |
| 4,946,778 | A | 8/1990 | Ladner et al. .............. 435/69.6 |
| 4,966,849 | A | 10/1990 | Vallee et al. ................. 435/199 |
| 5,091,513 | A | 2/1992 | Huston et al. ............ 530/387.3 |
| 5,096,815 | A | 3/1992 | Ladner et al. .............. 435/69.1 |
| 5,225,539 | A | 7/1993 | Winter ..................... 530/387.3 |
| 5,330,992 | A | 7/1994 | Eissenstat et al. ........... 514/312 |
| 5,459,015 | A | 10/1995 | Janjic et al. ..................... 435/6 |
| 5,530,101 | A | 6/1996 | Queen et al. ............ 530/387.3 |
| 5,585,089 | A | 12/1996 | Queen et al. ............ 424/133.1 |
| 5,677,171 | A | 10/1997 | Hudziak et al. ............ 435/7.23 |
| 5,693,761 | A | 12/1997 | Queen et al. ............ 536/23.53 |
| 5,693,762 | A | 12/1997 | Queen et al. ............ 530/387.3 |
| 5,707,632 | A | 1/1998 | Williams et al. ......... 424/198.1 |
| 5,772,997 | A | 6/1998 | Hudziak et al. ............ 424/130.1 |
| 5,840,301 | A | 11/1998 | Rockwell et al. ......... 424/143.1 |
| 5,843,450 | A | * | 12/1998 | Dawson et al. |
| 5,910,573 | A | 6/1999 | Pluckthun et al. ........ 530/387.3 |
| 5,942,602 | A | 8/1999 | Wels et al. ............. 530/388.22 |
| 6,129,915 | A | 10/2000 | Wels et al. ................ 424/143.1 |
| 6,165,464 | A | 12/2000 | Hudziak et al. .......... 424/142.1 |
| 6,183,975 | B1 | 2/2001 | Gargus et al. .............. 435/7.21 |
| 6,214,974 | B1 | 4/2001 | Rosenblum et al. ...... 530/391.9 |
| 6,294,353 | B1 | 9/2001 | Pack et al. ................. 435/69.1 |
| 6,300,064 | B1 | 10/2001 | Knappik et al. ................. 435/6 |
| 6,342,219 | B1 | 1/2002 | Thorpe et al. ............ 424/145.1 |
| 6,365,157 | B2 | 4/2002 | Rockwell et al. ......... 424/156.1 |
| 6,399,063 | B1 | 6/2002 | Hudziak et al. .......... 424/138.1 |

FOREIGN PATENT DOCUMENTS

| EP | 0 125 023 | 11/1984 |
|---|---|---|
| EP | 0 171 496 | 2/1986 |
| EP | 0 173 494 | 3/1986 |
| EP | 0 184 187 | 6/1986 |
| JP | 2004-305221 | 11/2004 |
| WO | WO 86/01533 | 3/1986 |
| WO | WO 87/02671 | 5/1987 |
| WO | WO 90/07861 | 7/1990 |
| WO | WO 92/22653 | 12/1992 |
| WO | WO 93/15210 | 8/1993 |
| WO | WO 94/10202 | 5/1994 |
| WO | WO 94/14808 | 7/1994 |
| WO | WO 96/13583 | 5/1996 |
| WO | WO 96/37621 | 11/1996 |
| WO | WO 97/08320 | 3/1997 |
| WO | WO 00/68424 | 11/2000 |

OTHER PUBLICATIONS

Skolnick et al. (Trends in Biotechnology, 18: 34-39, 2000).*
Jones (Pharmacogenomics Journal, 1:126-134, 2001).*
Tosatto et al (Current Pharmaceutical Design, 12:2067-2086, 2006).*
Trudel et al (Blood, 107(10):4039-4046, 2006).*
Mariuzza et al. (Annu. Rev. Biophys. Biophys. Chem., 16: 139-159, 1987).*
Giusti et al. (PNAS, 84 (9): 2926-2930, 1987).*
Rudikoff et al (PNAS 79:1979-1983, 1982).*
Johnston et al (JBC, 270(51):30643-30650, 1995).*
Chellaiah et al (JBC, 274(49): 34785-34794, 1999).*
Sorensen et al. (J. Cell Sci. Oct. 15, 2006; 119 (Pt 20): 4332-4341).*
Webster et al (TIG, 13(5):178-182, 1997).*
Antibody Engineering, Second Edition (Ed. Borrebaeck; 1995; Oxford University Press: New York; pp. 102-103).*
Cellular and Molecular Immunology (Eds. Abass et al.; 1991; W.B. Saunders: Philadelphia; p. 54).*
Baselga and Albanell, Mechanism of action of anti-HER2 monoclonal antibodies. Ann Oncol. 12 Suppl 1:S35-41 (2001).

(Continued)

*Primary Examiner*—Stephen L Rawlings
*Assistant Examiner*—Brad Duffy
(74) *Attorney, Agent, or Firm*—Winston & Strawn LLP

(57) ABSTRACT

Molecules comprising the antigen-binding portion of antibodies that block constitutive and/or ligand-dependent activation of a receptor protein tyrosine kinase, such as fibroblast growth factor receptor 3 (FGFR3), are found through screening methods, where a soluble dimeric form of a receptor protein tyrosine kinase is used as target for screening a library of antibody fragments displayed on the surface of bacteriophage. The molecules of the present invention which block constitutive activation can be administered to treat or inhibit skeletal dysplasia, craniosynostosis disorders, cell proliferative diseases or disorders, or tumor progression associated with the constitutive activation of a receptor protein tyrosine kinase.

6 Claims, 35 Drawing Sheets

OTHER PUBLICATIONS

Bellus et al., Identical mutations in three different fibroblast growth factor receptor genes in autosomal dominant craniosynostosis syndromes. Nature Genetics, 14:174-76 (1996).
Better et al, , *Escherichia coli* secretion of an active chimeric antibody fragment. Science 240(4855):1041-43 (1988).
Billerey, et al., Frequent FGFR3 mutations in papillary non-invasive bladder (pTa) tumors. Am J Pathol. 158(6):1955-9 (2001).
Blume-Jensen and Hunter, Oncogenic kinase signalling. Nature 411:355-65 (2001).
Boulianne et al, Production of functional chimaeric mouse/human antibody. Nature 312(5995):643-646 (1984).
Cabilly, et al., Generation of antibody activity from immunoglobulin polypeptide chains produced in *Escherichia coli*. PNAS U S A, 81(11):3273-7 (1984).
Cappellen et al., Frequent activating mutations of FGFR3 in human bladder and cervix carcinomas. Nature Genetics, 23:18-20 (1999).
Chesi et al., Activated fibroblast growth factor receptor 3 is an oncogene that contributes to tumor progression in multiple myeloma. Blood, 97(3):729-736 (2001).
Frank, Growth factors in age-related macular degeneration: pathogenic and therapeutic implications. Ophthalmic Res 29:341-53 (1997).
Galvin et al., Constitutive receptor activation by Crouzon syndrome mutations in fibroblast growth factor receptor (FGFR)2 and FGFR2/Neu chimeras. PNAS USA, 93:7894-99 (1996).
Gerwins et al., Function of fibroblast growth factors and vascular endothelial growth factors and their receptors in angiogenesis. Crit Rev Oncol Hematol 34(3):185-94 (2000).
Grigoriadis et al, Differentiation of muscle, fat, cartilage, and bone from progenitor cells present in a bone-derived clonal cell population: effect of dexamethasone. J Cell Biol 106(6):2139-51 (1988).
Knappik et al., Fully synthetic human combinatorial antibody libraries (HuCAL) based on modular consensus frameworks and CDRs randomized with trinucleotides. J. Mol. Biol., 296:57-86 (2000).
Kohfeldt et al., Properties of the extracellular calcium binding module of the proteoglycan testican. FEBS Lett. 414:557-561, 1997.
Kohler and Milstein, Continuous cultures of fused cells secreting antibody of predefined specificity. Nature, 256(5517):495-497 (1975).
Liu et al, Chimeric mouse-human IgG1 antibody that can mediate lysis of cancer cells. PNAS USA. 84(10):3439-3443 (1987).
Meinkoth and Wahl, Hybridization of nucleic acids immobilized on solid supports., Anal Biochem 138:267-284 (1984).
Meyers et al., Fibroblast growth factor receptor 3 (FGFR3) transmembrane mutation in Crouzon syndrome with acanthosis nigricans. Nature Genetics, 11:462-464 (1995).
Morrison et al., Chimeric human antibody molecules: mouse antigen-binding domains with human constant region domains. PNAS USA 81(21):6851-6855 (1984).
Muenke et al., A unique point mutation in the fibroblast growth factor receptor 3 gene (FGFR3) defines a new craniosynostosis syndrome. Am. J. Hum. Genet., 60:555-64 (1997).
Neuberger et al, A hapten-specific chimaeric IgE antibody with human physiological effector function. Nature 314(6008):268-270 (1985).
Ornitz, Regulation of chondrocyte growth and differentiation by fibroblast growth factor receptor 3. Novartis Found Symp 232:63-76; discussion 76-80, 272-82 (2001).
Ornitz and Itoh, Fibroblast Growth Factors, Genome Biol 2(3):review 3005.1-3005.12 (2001).
Plowright et al., Ectopic expression of fibroblast growth factor receptor 3 promotes myeloma cell proliferation and prevents apoptosis. Blood 95(3):992-8 (2000).
Ronchetti, et al., Deregulated FGFR3 mutants in multiple myeloma cell lines with t(4;14): comparative analysis of Y373C, K650E and the novel G384D mutations. Oncogene 20(27):3553-62 (2001).
Sahagan, et al., A genetically engineered murine/human chimeric antibody retains specificity for human tumor-associated antigen. J Immunol. 137(3):1066-74 (1986).
Sahni, et al., FGF signaling inhibits chondrocyte proliferation and regulates bone development through the STAT-1 pathway. Genes Dev. 13(11):1361-6 (1999).
Saito et al., Receptor heterodimerization: essential mechanism for platelet-derived growth factor-induced epidermal growth factor receptor transactivation. Mol Cell Biol, 21(19):6387-94 (2001).
Sato et al., Properties of two VEGF receptors, Flt-1 and KDR, in signal transduction. Ann N Y Acad Sci, 902:201-5; discussion 205-7 (2000).
Saltzman and Langer, Transport rates of proteins in porous materials with known microgeometry. Biophys. J, 55:163 (1989).
Schell et al., Mutations in FGFR1 and FGFR2 cause familial and sporadic Pfeiffer syndrome. Hum Mol Gen, 4:323-328 (1995).
Sherwood et al., Controlled antibody delivery systems. Biotechnology, 10(11):1446-9 (1992).
Tavormina et al., A novel skeletal dysplasia with developmental delay and acanthosis nigricans is caused by a Lys650Met mutation in the fibroblast growth factor receptor 3 gene. Am. J. Hum. Genet., 64:722-31 (1999).
Vajo et al., The molecular and genetic basis of fibroblast growth factor receptor 3 disorders: the achondroplasia family of skeletal dysplasias, Muenke craniosynostosis, and Crouzon syndrome with acanthosis nigricans. Endocrine Reviews, 21(1):23-39 (2000).
van Rhijn et al., Molecular grading of urothelial cell carcinoma with fibroblast growth factor receptor 3 and MIB-1 is superior to pathologic grade for the prediction of clinical outcome. J Clin Oncol. 21(10):1912-21 (2003).
Webster and Donoghue, FGFR activation in skeletal disorders: too much of a good thing. Trends Genetics 13(5):178-82 (1997).
Yamaguchi et al., Endostatin inhibits VEGF-induced endothelial cell migration and tumor growth independently of zinc binding. EMBO J. 18(16):4414-23 (1999).
Z. Fan et al., "Blockade of epidermal growth factor receptor function by bivalent and monovalent fragments of 225 anti-epidermal growth factor receptor monoclonal antibodies," Cancer Research, 53(18):4322-4328 (1993).
F.A. Montero-Julian et al., "Characterization of two monoclonal antibodies against the RON tyrosine kinase receptor," Hybridoma, 17(6):541-551 (1998).
T. Otsuki et al., "Expression of fibroblast growth factor and FGF-receptor family genes in human myeloma cells, including lines possessing t(4;14)(q16.3;q32.3) and FGFR3 translocation," International Journal of Oncology 15:1205-1212 (1999).
A. Yayon et al., "Isolation of peptides that inhibit binding of basic fibroblast growth factor to its receptor from a random phage-epitope library," Proc. Natl. Acad. Sci. USA, 90:10643-10647 (1993).
A-L Delezoide et al. "Abnormal FGFR 3 expression in cartilage of thanatophoric dysplasia fetuses", Human Molecular Genetics, 1997, vol. 6, No. 11:1899-1906.
P. A. Brittis et al. "Fibroblast Growth Factor Receptor Function is required for the Orderly Projection of Ganglion Cell Axons in the Developing Mammalian Retina", Molecular and Cellular Neuroscience 8, 5:120-128 (1996).
K. Keegan et al., "Isolation of an additional member of the fibroblast growth factor receptor family, FGFR-3", Proc Natl Acad Sci U S A. Feb. 15, 1991;88(4):1095-9.
R. Shiang et al., "Mutations in the transmembrane domain of FGFR3 cause the most common genetic form of dwarfism, achondroplasia", Cell. Jul. 29, 1994;78(2):335-42.

* cited by examiner

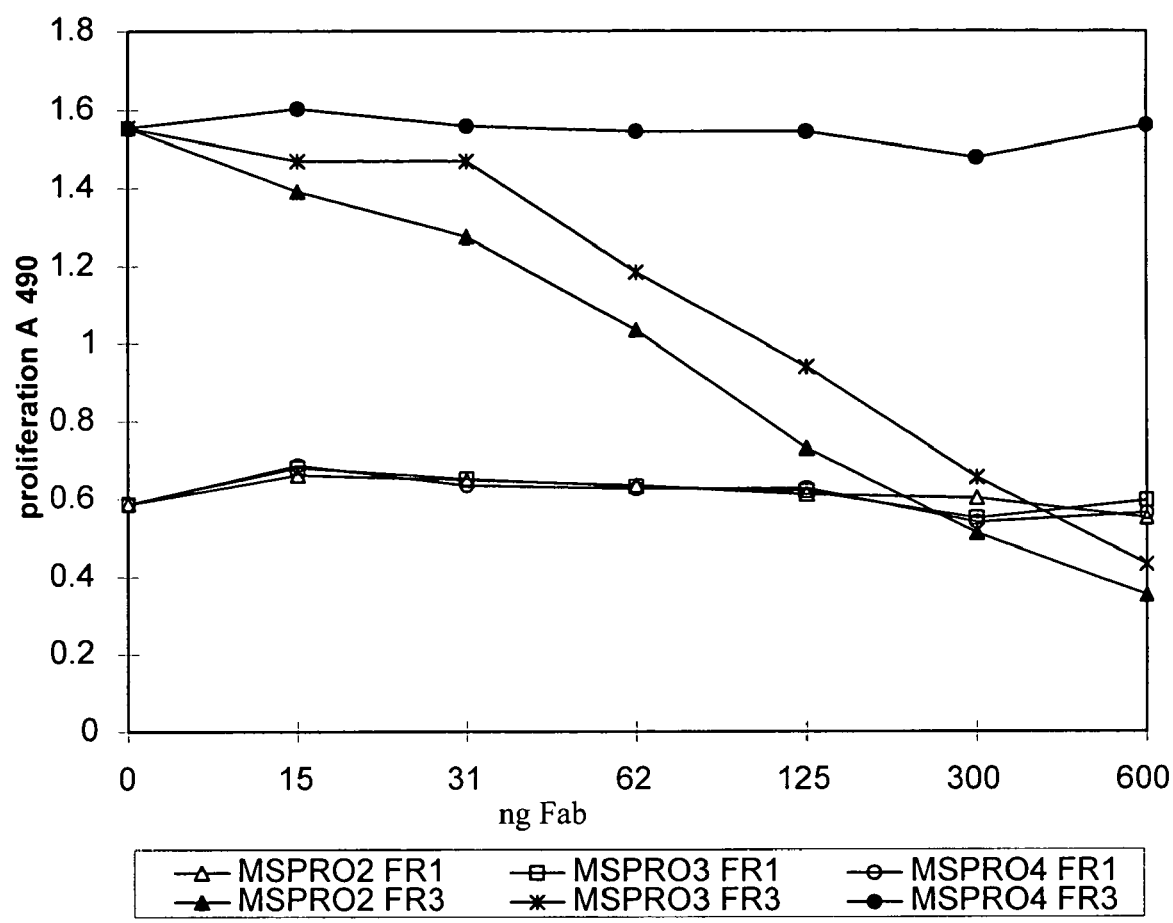

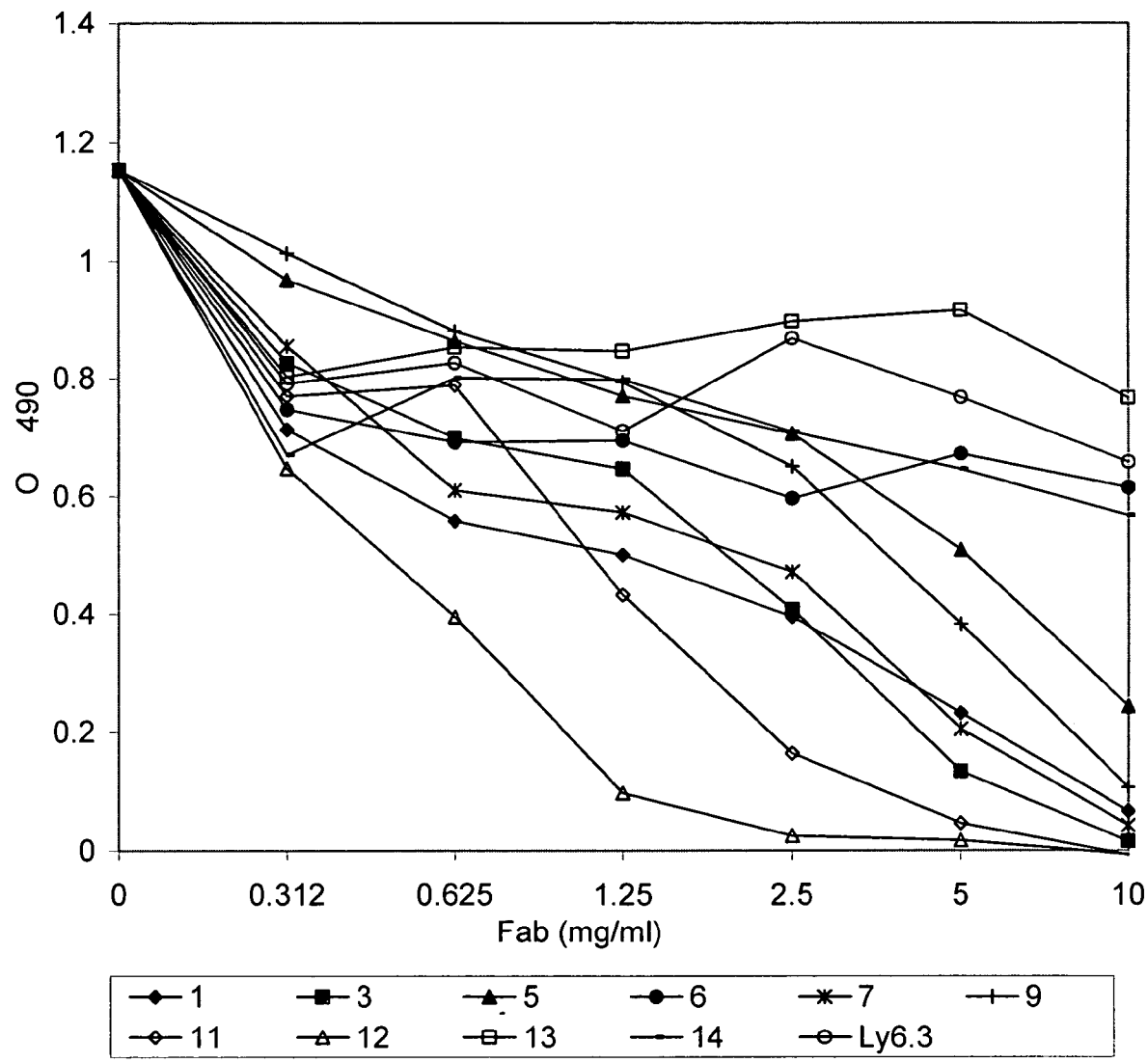

M14

W11

R1-1

R2-2

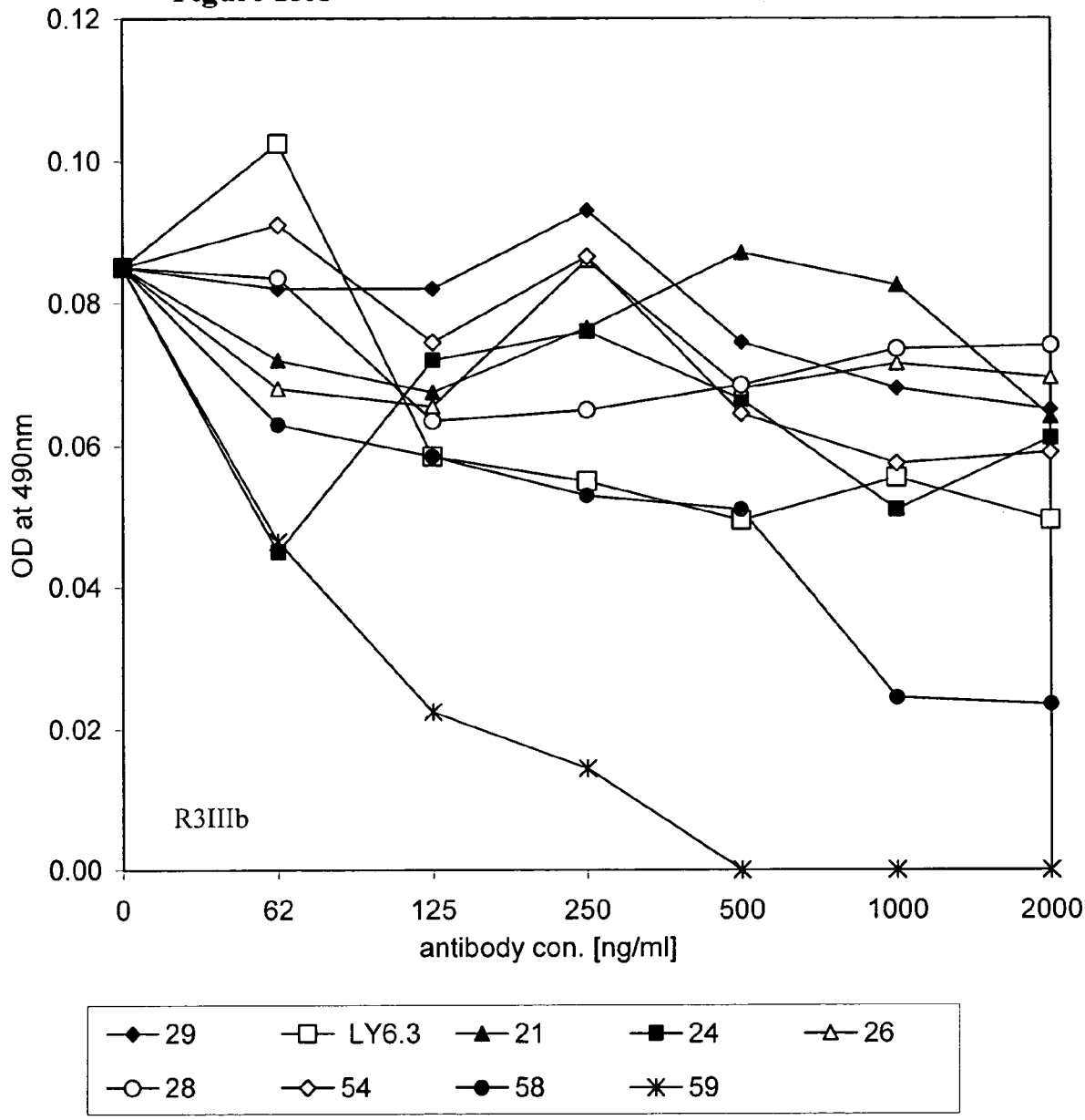

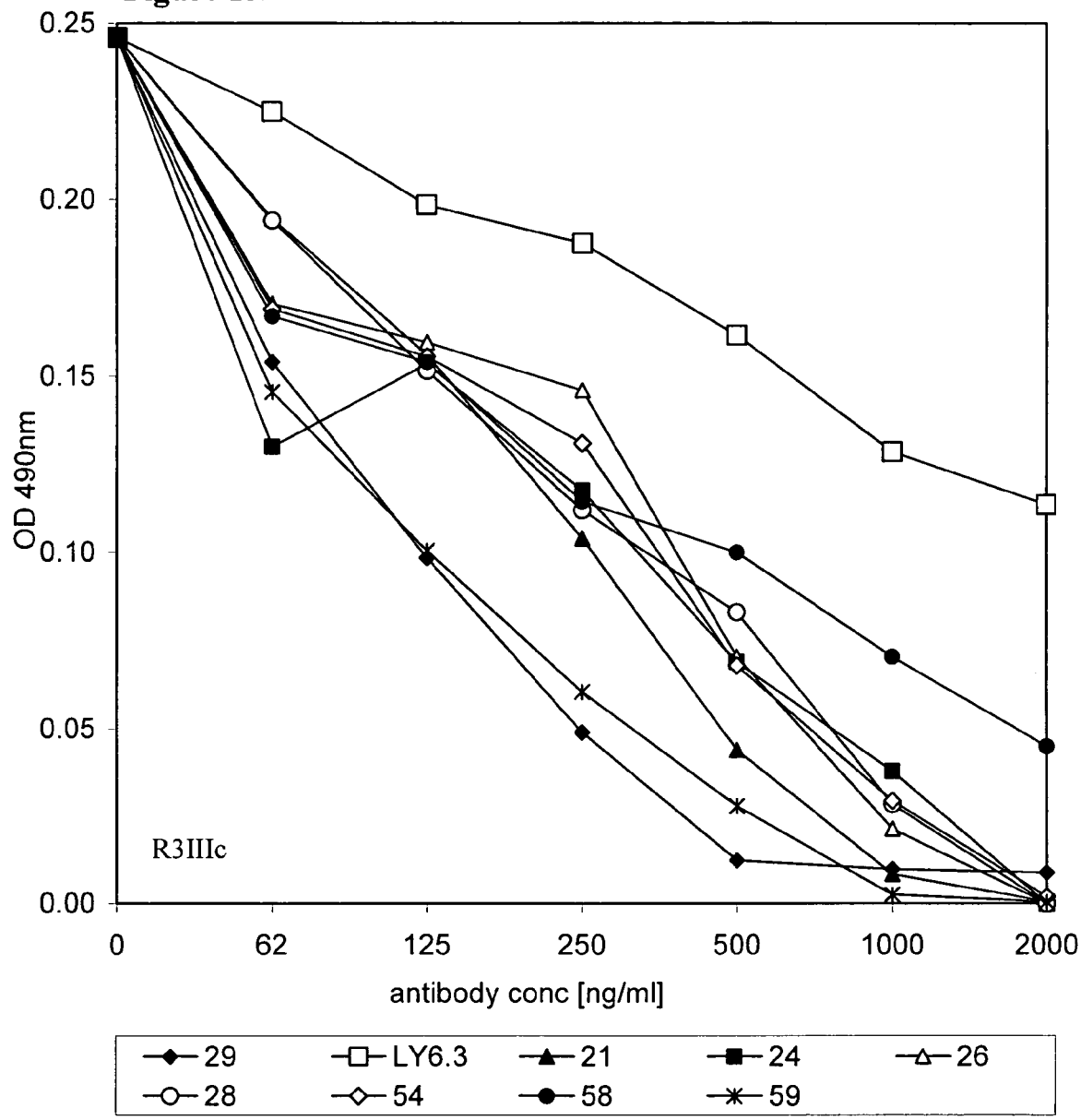

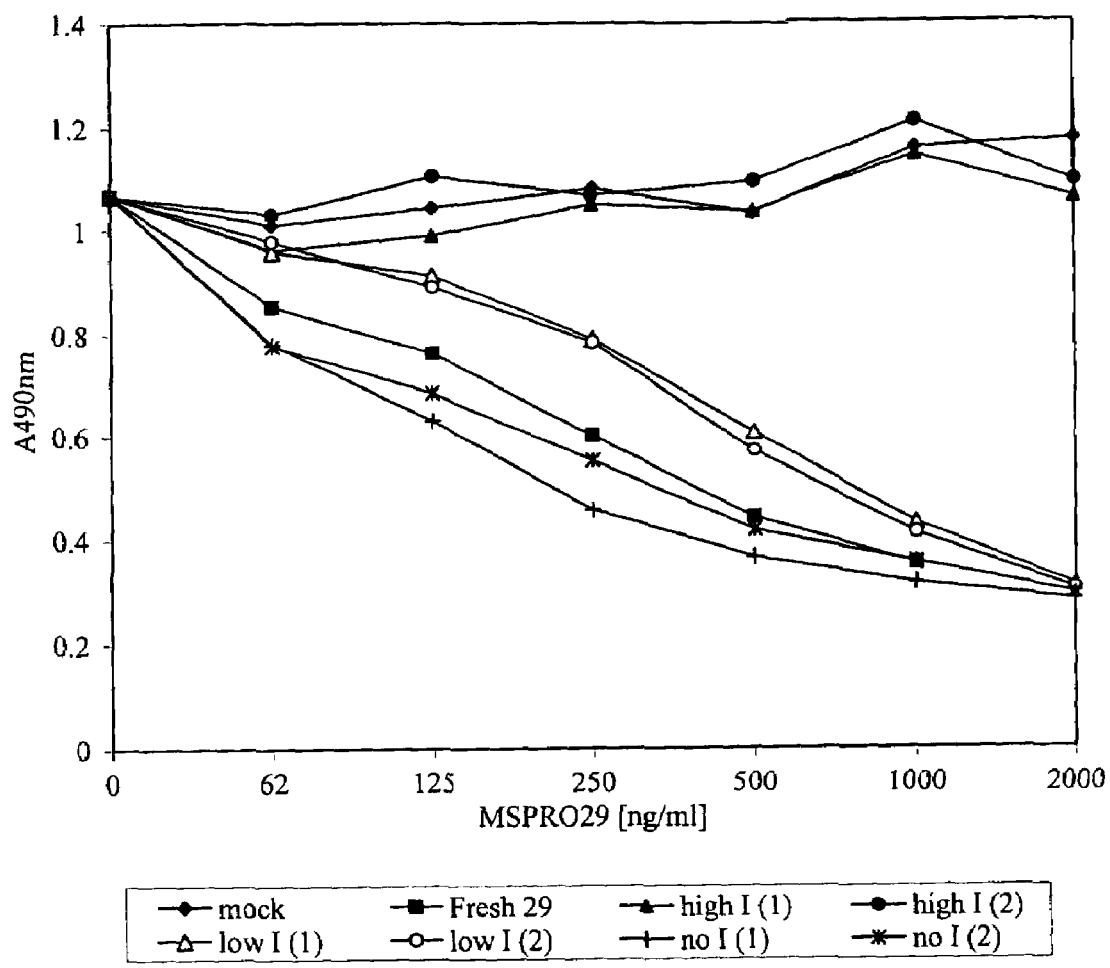

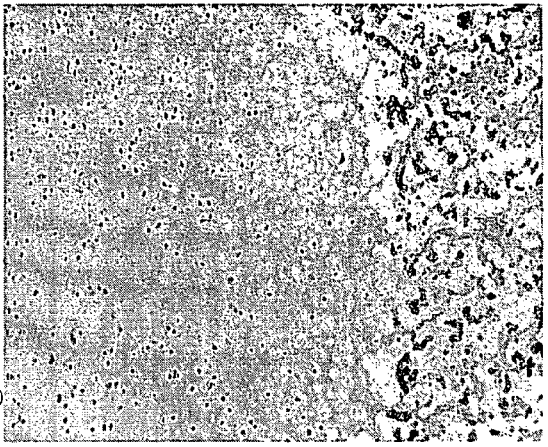
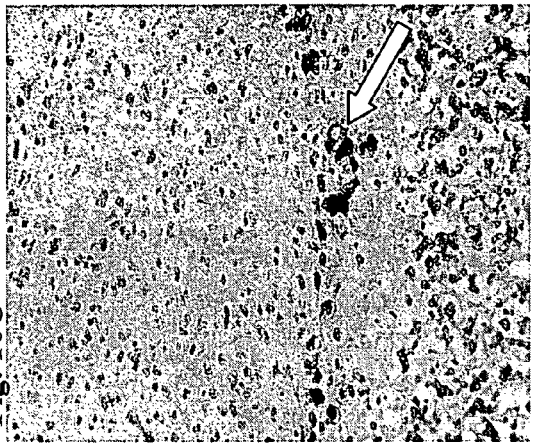
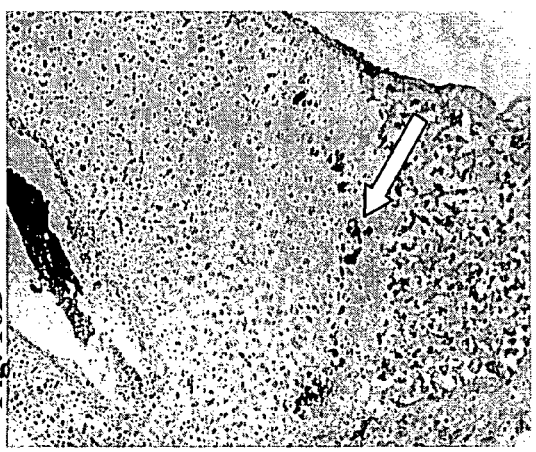

| Position | 1 | 2 | 3 | 4 | 5 | 6 | 7 | 8 | 9 | 10 | Framework 1 | | | | | | | | | 20 | 21 | 22 |
|---|---|---|---|---|---|---|---|---|---|---|---|---|---|---|---|---|---|---|---|---|---|---|
| | EcoRV | | | | | | BanII | | | | | | | | | | | | | | | |
| | | | | | | | | | | | 10 | 11 | 12 | 13 | 14 | 15 | 16 | 17 | 18 | 19 | | |
| VLK1 (SEQ ID NO: 54) | GAT | ATC | CAG | ATG | ACC | CAG | AGC | CCG | TCT | AGC | CTG | AGC | GCG | AGC | GTG | GGT | GAT | CGT | GTG | ACC | ATT | ACC |
| MSPro28 (SEQ ID NO: 55) | GAT | ATC | CAG | ATG | ACC | CAG | AGC | CCG | TCT | AGC | CTG | AGC | GCG | AGC | GTG | GGT | GAT | CGT | GTG | ACC | ATT | ACC |
| VLK3 (SEQ ID NO: 56) | GAT | ATC | GTG | CTG | ACC | CAG | AGC | CCG | GCG | ACC | CTG | AGC | CTG | TCT | CCG | GGC | GAA | CGT | GCG | ACC | CTG | AGC |
| MSPro24 (SEQ ID NO: 57) | GAT | ATC | GTG | CTG | ACC | CAG | AGC | CCG | GCG | ACC | CTG | AGC | CTG | TCT | CCG | GGC | GAA | CGT | GCG | ACC | CTG | AGC |
| MSPro29 (SEQ ID NO: 58) | GAT | ATC | GTG | CTG | ACC | CAG | AGC | CCG | GCG | ACC | CTG | AGC | CTG | TCT | CCG | GGC | GAA | CGT | GCG | ACC | CTG | AGC |
| VLK4 (SEQ ID NO: 59) | GAT | ATC | GTG | ATG | ACC | CAG | AGC | CCG | GAT | AGC | CTG | AGC | GTG | AGC | CTG | GGC | GAA | CGT | GCG | ACC | ATT | AAC |
| MSPro21 (SEQ ID NO: 60) | GAT | ATC | GTG | ATG | ACC | CAG | AGC | CCG | GAT | AGC | CTG | AGC | GTG | AGC | CTG | GGC | GAA | CGT | GCG | ACC | ATT | AAC |
| VL12 (SEQ ID NO: 61) | GAT | ATC | GCA | CTG | ACC | CAG | CCA | GCT | . | TCA | GTG | AGC | GGC | TCA | CCA | GGT | CAG | AGC | ATT | ACC | ATC | TCG |
| MSPro55 (SEQ ID NO: 62) | GAT | ATC | GCA | CTG | ACC | CAG | CCA | GCT | . | TCA | GTG | AGC | GGC | TCA | CCA | GGT | CAG | AGC | ATT | ACC | ATC | TCG |
| MSPro11 (SEQ ID NO: 63) | GAT | ATC | GCA | CTG | ACC | CAG | CCA | GCT | . | TCA | GTG | AGC | GGC | TCA | CCA | GGT | CAG | AGC | ATT | ACC | ATC | TCG |
| MSPro26 (SEQ ID NO: 64) | GAT | ATC | GCA | CTG | ACC | CAG | CCA | GCT | . | TCA | GTG | AGC | GGC | TCA | CCA | GGT | CAG | AGC | ATT | ACC | ATC | TCG |
| VL13 (SEQ ID NO: 65) | GAT | ATC | GAA | CTG | ACC | CAG | CCG | CCT | . | TCA | GTG | AGC | GTT | GCA | CCA | GGT | CAG | ACC | GCG | CGT | ATC | TCG |
| MSPro54 (SEQ ID NO: 66) | GAT | ATC | GAA | CTG | ACC | CAG | CCG | CCT | . | TCA | GTG | AGC | GTT | GCA | CCA | GGT | CAG | ACC | GCG | CGT | ATC | TCG |
| MSPro2 (SEQ ID NO: 67) | GAT | ATC | GAA | CTG | ACC | CAG | CCG | CCT | . | TCA | GTG | AGC | GTT | GCA | CCA | GGT | CAG | ACC | GCG | CGT | ATC | TCG |
| MSPro12 (SEQ ID NO: 68) | GAT | ATC | GAA | CTG | ACC | CAG | CCG | CCT | . | TCA | GTG | AGC | GTT | GCA | CCA | GGT | CAG | ACC | GCG | CGT | ATC | TCG |
| MSPro59 (SEQ ID NO: 69) | GAT | ATC | GAA | CTG | ACC | CAG | CCG | CCT | . | TCA | GTG | AGC | GTT | GCA | CCA | GGT | CAG | ACC | GCG | CGT | ATC | TCG |

VH

| Position | 1 | 2 | 3 | 4 | 5 | 6 | 7 | 8 | 9 | 10 | Framework 1 | | | | | | | | | 20 | 21 | 22 |
|---|---|---|---|---|---|---|---|---|---|---|---|---|---|---|---|---|---|---|---|---|---|---|
| | | | MfeI | | | | | | | | | | | | | | | | | | | |
| | | | | | | | | | | | 10 | 11 | 12 | 13 | 14 | 15 | 16 | 17 | 18 | 19 | | |
| VH1A (SEQ ID NO: 70) | GAA/CAG | GTG | CAA | TTG | GTT | CAG | TCT | GGC | GCG | GAA | GTG | AAA | AAA | CCG | GGC | AGC | AGC | GTG | AAA | GTG | AGC | TGC |
| MSPro21 (SEQ ID NO: 71) | CAG | GTG | CAA | TTG | GTT | CAG | TCT | GGC | GCG | GAA | GTG | AAA | AAA | CCG | GGC | AGC | AGC | GTG | AAA | GTG | AGC | TGC |
| MSPro24 (SEQ ID NO: 72) | CAG | GTG | CAA | TTG | GTT | CAG | TCT | GGC | GCG | GAA | GTG | AAA | AAA | CCG | GGC | AGC | AGC | GTG | AAA | GTG | AGC | TGC |
| MSPro28 (SEQ ID NO: 73) | CAG | GTG | CAA | TTG | GTT | CAG | TCT | GGC | GCG | GAA | GTG | AAA | AAA | CCG | GGC | AGC | AGC | GTG | AAA | GTG | AGC | TGC |
| VH1B (SEQ ID NO: 74) | GAA/CAG | GTG | CAA | TTG | GTT | CAG | AGC | GGC | GCG | GAA | GTG | AAA | AAA | CCG | GGC | GCG | AGC | GTG | AAA | GTG | AGC | TGC |
| MSPro54 (SEQ ID NO: 75) | CAG | GTG | CAA | TTG | GTT | CAG | AGC | GGC | GCG | GAA | GTG | AAA | AAA | CCG | GGC | GCG | AGC | GTG | AAA | GTG | AGC | TGC |
| MSPro55 (SEQ ID NO: 76) | CAG | GTG | CAA | TTG | GTT | CAG | AGC | GGC | GCG | GAA | GTG | AAA | AAA | CCG | GGC | GCG | AGC | GTG | AAA | GTG | AGC | TGC |
| MSPro2 (SEQ ID NO: 77) | CAG | GTG | CAA | TTG | GTT | CAG | AGC | GGC | GCG | GAA | GTG | AAA | AAA | CCG | GGC | GCG | AGC | GTG | AAA | GTG | AGC | TGC |
| MSPro11 (SEQ ID NO: 78) | CAG | GTG | CAA | TTG | GTT | CAG | AGC | GGC | GCG | GAA | GTG | AAA | AAA | CCG | GGC | GCG | CAA | GTG | AAA | GTG | AGC | TGC |
| MSPro26 (SEQ ID NO: 79) | CAG | GTG | CAA | TTG | GTT | GAA | AGC | GGC | GCG | GAA | GTG | AAA | AAA | CCG | GGC | GCG | CAA | GTG | AAA | GTG | AGC | TGC |
| MSPro29 (SEQ ID NO: 80) | CAG | GTG | CAA | TTG | GTT | GAA | AGC | GGC | GCG | GAA | GTG | AAA | AAA | CCG | GGC | GCG | CAA | GTG | AAA | GTG | AGC | TGC |
| VH2 (SEQ ID NO: 81) | GAA/CAG | GTG | CAA | TTG | AAA | GAA | AGC | GGC | CCG | GCC | CTG | GTG | AAA | CCG | ACC | CAA | ACC | CTG | ACC | CTG | ACC | TGT |
| MSPro12 (SEQ ID NO: 82) | CAG | GTG | CAA | TTG | AAA | GAA | AGC | GGC | CCG | GCC | CTG | GTG | AAA | CCG | ACC | CAA | ACC | CTG | ACC | CTG | ACC | TGT |
| VH3 (SEQ ID NO: 83) | GAA/CAG | GTG | CAA | TTG | CAA | GAA | TCT | GGT | CCG | GGC | CTG | GTG | AAA | CCG | AGC | CAG | ACC | CTG | AGC | CTG | ACC | TGT |
| MSPro59 (SEQ ID NO: 84) | CAG | GTG | CAA | TTG | CAA | CAG | TCT | GGT | CCG | GGC | CTG | GTG | AAA | CCG | AGC | CAG | ACC | CTG | AGC | CTG | ACC | TGT |

SEQUENCE LISTING

```
<160> NUMBER OF SEQ ID NOS: 106

<210> SEQ ID NO 1
<211> LENGTH: 806
<212> TYPE: PRT
<213> ORGANISM: Homo sapiens
<300> PUBLICATION INFORMATION:
<308> DATABASE ACCESSION NUMBER: np_000133
<309> DATABASE ENTRY DATE: 2001-02-21
<313> RELEVANT RESIDUES: (1)..(806)

<400> SEQUENCE: 1

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175
```

-continued

```
Pro Ala Ala Gly Asn Pro Thr Pro Ser Ile Ser Trp Leu Lys Asn Gly
            180                 185                 190
Arg Glu Phe Arg Gly Glu His Arg Ile Gly Ile Lys Leu Arg His
        195                 200                 205
Gln Gln Trp Ser Leu Val Met Glu Ser Val Val Pro Ser Asp Arg Gly
        210                 215                 220
Asn Tyr Thr Cys Val Val Glu Asn Lys Phe Gly Ser Ile Arg Gln Thr
225                 230                 235                 240
Tyr Thr Leu Asp Val Leu Glu Arg Ser Pro His Arg Pro Ile Leu Gln
                245                 250                 255
Ala Gly Leu Pro Ala Asn Gln Thr Ala Val Leu Gly Ser Asp Val Glu
            260                 265                 270
Phe His Cys Lys Val Tyr Ser Asp Ala Gln Pro His Ile Gln Trp Leu
        275                 280                 285
Lys His Val Glu Val Asn Gly Ser Lys Val Gly Pro Asp Gly Thr Pro
        290                 295                 300
Tyr Val Thr Val Leu Lys Thr Ala Gly Ala Asn Thr Thr Asp Lys Glu
305                 310                 315                 320
Leu Glu Val Leu Ser Leu His Asn Val Thr Phe Glu Asp Ala Gly Glu
                325                 330                 335
Tyr Thr Cys Leu Ala Gly Asn Ser Ile Gly Phe Ser His His Ser Ala
            340                 345                 350
Trp Leu Val Val Leu Pro Ala Glu Glu Glu Leu Val Glu Ala Asp Glu
        355                 360                 365
Ala Gly Ser Val Tyr Ala Gly Ile Leu Ser Tyr Gly Val Gly Phe Phe
        370                 375                 380
Leu Phe Ile Leu Val Val Ala Ala Val Thr Leu Cys Arg Leu Arg Ser
385                 390                 395                 400
Pro Pro Lys Lys Gly Leu Gly Ser Pro Thr Val His Lys Ile Ser Arg
                405                 410                 415
Phe Pro Leu Lys Arg Gln Val Ser Leu Glu Ser Asn Ala Ser Met Ser
            420                 425                 430
Ser Asn Thr Pro Leu Val Arg Ile Ala Arg Leu Ser Ser Gly Glu Gly
        435                 440                 445
Pro Thr Leu Ala Asn Val Ser Glu Leu Glu Leu Pro Ala Asp Pro Lys
        450                 455                 460
Trp Glu Leu Ser Arg Ala Arg Leu Thr Leu Gly Lys Pro Leu Gly Glu
465                 470                 475                 480
Gly Cys Phe Gly Gln Val Val Met Ala Glu Ala Ile Gly Ile Asp Lys
                485                 490                 495
Asp Arg Ala Ala Lys Pro Val Thr Val Ala Val Lys Met Leu Lys Asp
            500                 505                 510
Asp Ala Thr Asp Lys Asp Leu Ser Asp Leu Val Ser Glu Met Glu Met
        515                 520                 525
Met Lys Met Ile Gly Lys His Lys Asn Ile Ile Asn Leu Leu Gly Ala
        530                 535                 540
Cys Thr Gln Gly Gly Pro Leu Tyr Val Leu Val Glu Tyr Ala Ala Lys
545                 550                 555                 560
Gly Asn Leu Arg Glu Phe Leu Arg Ala Arg Arg Pro Pro Gly Leu Asp
                565                 570                 575
Tyr Ser Phe Asp Thr Cys Lys Pro Pro Glu Glu Gln Leu Thr Phe Lys
            580                 585                 590
```

```
Asp Leu Val Ser Cys Ala Tyr Gln Val Ala Arg Gly Met Glu Tyr Leu
            595                 600                 605

Ala Ser Gln Lys Cys Ile His Arg Asp Leu Ala Ala Arg Asn Val Leu
        610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
        755                 760                 765

Gln Tyr Ser Pro Gly Gly Gln Asp Thr Pro Ser Ser Ser Ser Ser Gly
770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 2
<211> LENGTH: 32
<212> TYPE: DNA
<213> ORGANISM: Artificial Sequence
<220> FEATURE:
<223> OTHER INFORMATION: artificial primer

<400> SEQUENCE: 2
acgtgctagc tgagtccttg gggacggagc ag                              32

<210> SEQ ID NO 3
<211> LENGTH: 55
<212> TYPE: DNA
<213> ORGANISM: Artificial Sequence
<220> FEATURE:
<223> OTHER INFORMATION: artificial primer

<400> SEQUENCE: 3
acgtctcgag ttaatggtga tggtgatggt gtgcatacac acagcccgcc tcgtc      55

<210> SEQ ID NO 4
<211> LENGTH: 1147
<212> TYPE: DNA
<213> ORGANISM: Homo sapiens
<300> PUBLICATION INFORMATION:
<308> DATABASE ACCESSION NUMBER: m58051
<309> DATABASE ENTRY DATE: 1994-11-08
<313> RELEVANT RESIDUES: (1)..(1147)

<400> SEQUENCE: 4
gcgcgctgcc tgaggacgcc gcggcccccg ccccgccat gggcgcccct gcctgcgccc   60
```

-continued

| | |
|---|---|
| tcgcgctctg cgtggccgtg gccatcgtgg ccggcgcctc ctcggagtcc ttggggacgg | 120 |
| agcagcgcgt cgtggggcga gcggcagaag tcccgggccc agagcccggc cagcaggagc | 180 |
| agttggtctt cggcagcggg gatgctgtgg agctgagctg tcccccgccc gggggtggtc | 240 |
| ccatggggcc cactgtctgg gtcaaggatg gcacagggct ggtgccctcg agcgtgtcc | 300 |
| tggtggggcc ccagcggctg caggtgctga atgcctccca cgaggactcc ggggcctaca | 360 |
| gctgccggca gcggctcacg cagcgcgtac tgtgccactt cagtgtgcgg gtgacagacg | 420 |
| ctccatcctc gggagatgac gaagacgggg aggacgaggc tgaggacaca ggtgtggaca | 480 |
| caggggcccc ttactggaca cggcccgagc ggatggacaa gagctgctg gccgtgccgg | 540 |
| ccgccaacac cgtccgcttc cgctgccag ccgctggcaa ccccactccc tccatctcct | 600 |
| ggctgaagaa cggcagggag ttccgcggcg agcaccgcat tggaggcatc aagctgcggc | 660 |
| atcagcagtg gagcctggtc atggaaagcg tggtgccctc ggaccgcggc aactacacct | 720 |
| gcgtcgtgga gaacaagttt ggcagcatcc ggcagacgta cacgctggac gtgctggagc | 780 |
| gctccccgca ccggcccatc ctgcaggcgg gctgccggc caaccagacg gcggtgctgg | 840 |
| gcagcgacgt ggagttccac tgcaaggtgt acagtgacgc acagcccac atccagtggc | 900 |
| tcaagcacgt ggaggtgaac ggcagcaagg tgggcccgga cggcacaccc tacgttaccg | 960 |
| tgctcaagac ggcgggcgct aacaccaccg acaaggagct agaggttctc tccttgcaca | 1020 |
| acgtcacctt tgaggacgcc ggggagtaca cctgcctggc gggcaattct attgggtttt | 1080 |
| ctcatcactc tgcgtggctg gtggtgctgc cagccgagga ggagctggtg gaggctgacg | 1140 |
| aggcggg | 1147 |

<210> SEQ ID NO 5
<211> LENGTH: 5695
<212> TYPE: DNA
<213> ORGANISM: Artificial sequence
<220> FEATURE:
<223> OTHER INFORMATION: Expression Vector pCEP-PU/AC7

<400> SEQUENCE: 5

| | |
|---|---|
| gacggatcgg gagatctccc gatcccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |

-continued

```
gtttaaactt aagcttggta ccgagctcgg atccccgtcg tgcatctatc gaaggtcgtg    960
gagatcccga ggagcccaaa tcttgtgaca aaactcacac atgcccaccg tgcccagcac   1020
ctgaactcct gggggggaccg tcagtcttcc tcttcccccc aaaacccaag gacaccctca  1080
tgatctcccg gaccoctgag gtcacatgcg tggtggtgga cgtgagccac gaagaccctg   1140
aggtcaagtt caactggtac gtggacggcg tggaggtgca taatgccaag acaaagccgc   1200
gggaggagca gtacaacagc acgtaccggg tggtcagcgt cctcaccgtc ctgcaccagg   1260
actggctgaa tggcaaggag tacaagtgca aggtctccaa caaagccctc ccagccccca  1320
tcgagaaaac catctccaaa gccaaagggc agccccgaga accacaggtg tacaccctgc  1380
ccccatcccg ggatgagctg accaagaacc aggtcagcct gacctgcctg gtcaaaggct   1440
tctatcccag cgacatcgcc gtggagtggg agagcaatgg gcagccggag aacaactaca   1500
agaccacgcc tcccgtgctg gactccgacg gctccttctt cctctacagc aagctcaccg   1560
tggacaagag caggtggcag caggggaacg tcttctcatg ctccgtgatg catgaggctc   1620
tgcacaacca ctacacgcag aagagcctct ccctgtctcc gggtaaatga tctagagggc   1680
ccgtttaaac ccgctgatca gcctcgactg tgccttctag ttgccagcca tctgttgttt   1740
gcccctcccc cgtgccttcc ttgaccctgg aaggtgccac tcccactgtc ctttcctaat   1800
aaaatgagga aattgcatcg cattgtctga gtaggtgtca ttctattctg ggggtgggg   1860
tggggcagga cagcaagggg gaggattggg aagacaatag caggcatgct ggggatgcgg  1920
tgggctctat ggcttctgag gcggaaagaa ccagctgggg ctctaggggg tatccccacg   1980
cgccctgtag cggcgcatta agcgcggcgg gtgtggtggt tacgcgcagc gtgaccgcta   2040
cacttgccag cgccctagcg cccgctcctt tcgctttctt cccttccttt ctcgccacgt   2100
tcgccggctt tccccgtcaa gctctaaatc ggggcatccc tttagggttc cgatttagtg   2160
ctttacggca cctcgacccc aaaaaacttg attagggtga tggttcacgt agtgggccat   2220
cgccctgata acggttttt cgcccttga cgttggagtc cacgttcttt aatagtggac   2280
tcttgttcca aactggaaca acactcaacc ctatctcggt ctattctttt gatttataag   2340
ggattttggg gatttcggcc tattggttaa aaaatgagct gatttaacaa aaatttaacg   2400
cgaattaatt ctgtggaatg tgtgtcagtt agggtgtgga aagtccccag gctccccagg   2460
caggcagaag tatgcaaagc atgcatctca attagtcagc aaccaggtgt ggaaagtccc   2520
caggctcccc agcaggcaga agtatgcaaa gcatgcatct caattagtca gcaaccatag   2580
tcccgcccct aactccgccc atcccgccc taactccgcc cagttccgcc cattctccgc   2640
cccatggctg actaattttt tttatttatg cagaggccga ggccgcctct gcctctgagc   2700
tattccagaa gtagtgagga ggcttttttg gaggcctagg cttttgcaaa aagctcccgg   2760
gagcttgtat atccattttc ggatctgatc agcacgtgtt gacaattaat catcggcata   2820
gtatatcggc atagtataat acgacaaggt gaggaactaa accatggcca agttgaccag   2880
tgccgttccg tgctcaccg cgcgcgacgt cgccggagcg tcgagttct ggaccgaccg    2940
gctcgggttc tcccgggact tcgtggagga cgacttcgcc ggtgtggtcc gggacgacgt   3000
gaccctgttc atcagcgcgg tccaggacca ggtggtgccg gacaacaccc tggcctgggt   3060
gtgggtgcgc ggcctggacg agctgtacgc cgagtggtcg gaggtcgtgt ccacgaactt   3120
ccggacgcc tcccggccgg ccatgaccga gatcggcgag cagccgtggg ggcgggagtt   3180
cgccctgcgc gacccggccg gcaactgcgt gcacttcgtg gccgaggagc aggactgaca   3240
cgtgctacga gatttcgatt ccaccgccgc cttctatgaa aggttgggct tcggaatcgt   3300
```

```
tttccgggac gccggctgga tgatcctcca gcgcggggat ctcatgctgg agttcttcgc   3360
ccaccccaac ttgtttattg cagcttataa tggttacaaa taaagcaata gcatcacaaa   3420
tttcacaaat aaagcatttt tttcactgca ttctagttgt ggtttgtcca aactcatcaa   3480
tgtatcttat catgtctgta taccgtcgac ctctagctag agcttggcgt aatcatggtc   3540
atagctgttt cctgtgtgaa attgttatcc gctcacaatt ccacacaaca tacgagccgg   3600
aagcataaag tgtaaagcct ggggtgccta atgagtgagc taactcacat taattgcgtt   3660
gcgctcactg cccgctttcc agtcgggaaa cctgtcgtgc cagctgcatt aatgaatcgg   3720
ccaacgcgcg gggagaggcg gtttgcgtat tgggcgctct tccgcttcct cgctcactga   3780
ctcgctgcgc tcggtcgttc ggctgcggcg agcggtatca gctcactcaa aggcggtaat   3840
acggttatcc acagaatcag gggataacgc aggaaagaac atgtgagcaa aaggccagca   3900
aaaggccagg aaccgtaaaa aggccgcgtt gctggcgttt ttccataggc tccgcccccc   3960
tgacgagcat cacaaaaatc gacgctcaag tcagaggtgg cgaaacccga caggactata   4020
aagataccag gcgtttcccc ctggaagctc cctcgtgcgc tctcctgttc cgaccctgcc   4080
gcttaccgga tacctgtccg cctttctccc ttcgggaagc gtggcgcttt ctcaatgctc   4140
acgctgtagg tatctcagtt cggtgtaggt cgttcgctcc aagctgggct gtgtgcacga   4200
accccccgtt cagcccgacc gctgcgcctt atccggtaac tatcgtcttg agtccaaccc   4260
ggtaagacac gacttatcgc cactggcagc agccactggt aacaggatta gcagagcgag   4320
gtatgtaggc ggtgctacag agttcttgaa gtggtggcct aactacggct acactagaag   4380
gacagtattt ggtatctgcg ctctgctgaa gccagttacc ttcggaaaaa gagttggtag   4440
ctcttgatcc ggcaaacaaa ccaccgctgg tagcggtggt ttttttgttt gcaagcagca   4500
gattacgcgc agaaaaaaag gatctcaaga agatcctttg atcttttcta cggggtctga   4560
cgctcagtgg aacgaaaact cacgttaagg gattttggtc atgagattat caaaaaggat   4620
cttcacctag atccttttaa attaaaaatg aagttttaaa tcaatctaaa gtatatatga   4680
gtaaacttgg tctgacagtt accaatgctt aatcagtgag gcacctatct cagcgatctg   4740
tctatttcgt tcatccatag ttgcctgact ccccgtcgtg tagataacta cgatacggga   4800
gggcttacca tctggcccca gtgctgcaat gataccgcga cccacgct caccggctcc   4860 agatttatca gcaataaacc agccagccgg aagggccgag cgcagaagtg gtcctgcaac   4920
tttatccgcc tccatccagt ctattaattg ttgccgggaa gctagagtaa gtagttcgcc   4980
agttaatagt ttgcgcaacg ttgttgccat tgctacaggc atcgtggtgt cacgctcgtc   5040
gtttggtatg gcttcattca gctccggttc ccaacgatca aggcgagtta catgatcccc   5100
catgttgtgc aaaaaagcgg ttagctcctt cggtcctccg atcgttgtca gaagtaagtt   5160
ggccgcagtg ttatcactca tggttatggc agcactgcat aattctctta ctgtcatgcc   5220
atccgtaaga tgcttttctg tgactggtga gtactcaacc aagtcattct gagaatagtg   5280
tatgcggcga ccgagttgct cttgcccggc gtcaatacgg gataataccg cgccacatag   5340
cagaacttta aaagtgctca tcattggaaa acgttcttcg ggcgaaaac tctcaaggat   5400 cttaccgctg ttgagatcca gttcgatgta acccactcgt gcacccaact gatcttcagc   5460
atcttttact ttcaccagcg tttctgggtg agcaaaaaca ggaaggcaaa atgccgcaaa   5520
aaagggaata agggcgacac ggaaatgttg aatactcata ctcttccttt ttcaatatta   5580
ttgaagcatt tatcagggtt attgtctcat gagcggatac atatttgaat gtatttagaa   5640
```
aaataaacaa atagggggttc cgcgcacatt tccccgaaaa gtgccacctg acgtc        5695

<210> SEQ ID NO 6
<211> LENGTH: 235
<212> TYPE: PRT
<213> ORGANISM: Artificial sequence
<220> FEATURE:
<223> OTHER INFORMATION: Fc domain of Immunoglobulin

<400> SEQUENCE: 6

```
Asp Pro Glu Pro Lys Ser Cys Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asn Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Lys
225                 230                 235
```

<210> SEQ ID NO 7
<211> LENGTH: 1078
<212> TYPE: DNA
<213> ORGANISM: Homo sapiens
<220> FEATURE:
<221> NAME/KEY: mutation
<222> LOCATION: (1046)..(1048)
<223> OTHER INFORMATION: BASE PAIRS ENCODING THANATOPHORIC DYSPLASIA
    (TD) SUBSTITUTION IN FGFR3

<400> SEQUENCE: 7
tgagtccttg gggacggagc agcgcgtcgt ggggcgagcg gcagaagtcc cgggcccaga        60
gcccggccag caggagcagt tggtcttcgg cagcggggat gctgtggagc tgagctgtcc       120
cccgcccggg ggtggtccca tgggccccac tgtctgggtc aaggatggca cagggctggt       180
gccctcggag cgtgtcctgg tggggcccca gcggctgcag gtgctgaatg cctcccacga       240
ggactccggg gcctacagct gccggcagcg gctcacgcag cgcgtactgt gccacttcag       300

```
tgtgcgggtg acagacgctc catcctcggg agatgacgaa gacggggagg acgaggctga    360
ggacacaggt gtggacacag gggcccctta ctggacacgg cccgagcgga tggacaagaa    420
gctgctggcc gtgccggccg ccaacaccgt ccgcttccgc tgcccagccg ctggcaaccc    480
cactccctcc atctcctggc tgaagaacgg cagggagttc cgcggcgagc accgcattgg    540
aggcatcaag ctgcggcatc agcagtggag cctggtcatg gaaagcgtgg tgccctcgga    600
ccgcggcaac tacacctgcg tcgtggagaa caagtttggc agcatccggc agacgtacac    660
gctggacgtg ctggagcgct ccccgcaccg gcccatcctg caggcggggc tgccggccaa    720
ccagacggcg gtgctgggca cgacgtggaa gttccactgc aaggtgtaca gtgacgcaca    780
gccccacatc cagtggctca agcacgtgga ggtgaacggc agcaaggtgg cccggacgg    840 cacaccctac gttaccgtgc tcaagacggc gggcgctaac accaccgaca aggagctaga    900
ggttctctcc ttgcacaacg tcacctttga ggacgccggg gagtacacct gcctggcggg    960
caattctatt gggttttctc atcactctgc gtggctggtg gtgctgccag ccgaggagga    1020
gctggtggag gctgacgagg cgggctgtgt gtatgcacac catcaccatc accattaa    1078
```

<210> SEQ ID NO 8
<211> LENGTH: 9
<212> TYPE: PRT
<213> ORGANISM: Artificial Sequence
<220> FEATURE:
<223> OTHER INFORMATION: CDR domain from phage library

<400> SEQUENCE: 8

Asp Phe Leu Gly Tyr Glu Phe Asp Tyr
1               5

<210> SEQ ID NO 9
<211> LENGTH: 9
<212> TYPE: PRT
<213> ORGANISM: Artificial Sequence
<220> FEATURE:
<223> OTHER INFORMATION: CDR domain from phage library

<400> SEQUENCE: 9

Gln Ser Tyr Asp Tyr Ser Ala Asp Tyr
1               5

<210> SEQ ID NO 10
<211> LENGTH: 17
<212> TYPE: PRT
<213> ORGANISM: Artificial Sequence
<220> FEATURE:
<223> OTHER INFORMATION: CDR domain from phage library

<400> SEQUENCE: 10

Tyr Tyr Gly Ser Ser Leu Tyr His Tyr Val Phe Gly Gly Phe Ile Asp
1               5                   10                  15

Tyr

<210> SEQ ID NO 11
<211> LENGTH: 7
<212> TYPE: PRT
<213> ORGANISM: Artificial Sequence
<220> FEATURE:
<223> OTHER INFORMATION: CDR domain from phage library

<400> SEQUENCE: 11

Gln Ser His His Phe Tyr Glu

```
<210> SEQ ID NO 12
<211> LENGTH: 20
<212> TYPE: PRT
<213> ORGANISM: Artificial Sequence
<220> FEATURE:
<223> OTHER INFORMATION: CDR domain from phage library

<400> SEQUENCE: 12

Tyr His Ser Trp Tyr Glu Met Gly Tyr Tyr Gly Ser Thr Val Gly Tyr
1               5                   10                  15

Met Phe Asp Tyr
            20

<210> SEQ ID NO 13
<211> LENGTH: 8
<212> TYPE: PRT
<213> ORGANISM: Artificial Sequence
<220> FEATURE:
<223> OTHER INFORMATION: CDR domain from phage library

<400> SEQUENCE: 13

Gln Ser Tyr Asp Phe Asp Phe Ala
1               5

<210> SEQ ID NO 14
<211> LENGTH: 10
<212> TYPE: PRT
<213> ORGANISM: Artificial Sequence
<220> FEATURE:
<223> OTHER INFORMATION: CDR domain from phage library

<400> SEQUENCE: 14

Asp Asn Trp Phe Lys Pro Phe Ser Asp Val
1               5                   10

<210> SEQ ID NO 15
<211> LENGTH: 8
<212> TYPE: PRT
<213> ORGANISM: Artificial Sequence
<220> FEATURE:
<223> OTHER INFORMATION: CDR domain from phage library

<400> SEQUENCE: 15

Gln Gln Tyr Asp Ser Ile Pro Tyr
1               5

<210> SEQ ID NO 16
<211> LENGTH: 10
<212> TYPE: PRT
<213> ORGANISM: Artificial Sequence
<220> FEATURE:
<223> OTHER INFORMATION: CDR domain from phage library

<400> SEQUENCE: 16

Val Asn His Trp Thr Tyr Thr Phe Asp Tyr
1               5                   10

<210> SEQ ID NO 17
<211> LENGTH: 8
<212> TYPE: PRT
<213> ORGANISM: Artificial Sequence
<220> FEATURE:
<223> OTHER INFORMATION: CDR domain from phage library

<400> SEQUENCE: 17
```

Gln Gln Met Ser Asn Tyr Pro Asp
1               5

<210> SEQ ID NO 18
<211> LENGTH: 17
<212> TYPE: PRT
<213> ORGANISM: Artificial Sequence
<220> FEATURE:
<223> OTHER INFORMATION: CDR domain from phage library

<400> SEQUENCE: 18

Gly Tyr Trp Tyr Ala Tyr Phe Thr Tyr Ile Asn Tyr Gly Tyr Phe Asp
1               5                   10                  15

Asn

<210> SEQ ID NO 19
<211> LENGTH: 9
<212> TYPE: PRT
<213> ORGANISM: Artificial Sequence
<220> FEATURE:
<223> OTHER INFORMATION: CDR domain from phage library

<400> SEQUENCE: 19

Gln Ser Tyr Asp Asn Asn Ser Asp Val
1               5

<210> SEQ ID NO 20
<211> LENGTH: 18
<212> TYPE: PRT
<213> ORGANISM: Artificial Sequence
<220> FEATURE:
<223> OTHER INFORMATION: CDR domain from phage library

<400> SEQUENCE: 20

Thr Trp Gln Tyr Ser Tyr Phe Tyr Tyr Leu Asp Gly Gly Tyr Tyr Phe
1               5                   10                  15

Asp Ile

<210> SEQ ID NO 21
<211> LENGTH: 8
<212> TYPE: PRT
<213> ORGANISM: Artificial Sequence
<220> FEATURE:
<223> OTHER INFORMATION: CDR domain from phage library

<400> SEQUENCE: 21

Gln Gln Thr Asn Asn Ala Pro Val
1               5

<210> SEQ ID NO 22
<211> LENGTH: 17
<212> TYPE: PRT
<213> ORGANISM: Artificial Sequence
<220> FEATURE:
<223> OTHER INFORMATION: CDR domain from phage library

<400> SEQUENCE: 22

Asn Met Ala Tyr Thr Asn Tyr Gln Tyr Val Asn Met Pro His Phe Asp
1               5                   10                  15

Tyr

<210> SEQ ID NO 23
<211> LENGTH: 8
<212> TYPE: PRT

```
<213> ORGANISM: Artificial Sequence
<220> FEATURE:
<223> OTHER INFORMATION: CDR domain from phage library

<400> SEQUENCE: 23

Gln Ser Tyr Asp Tyr Phe Lys Leu
1               5

<210> SEQ ID NO 24
<211> LENGTH: 8
<212> TYPE: PRT
<213> ORGANISM: Artificial Sequence
<220> FEATURE:
<223> OTHER INFORMATION: CDR domain from phage library

<400> SEQUENCE: 24

Ser Tyr Tyr Pro Asp Phe Asp Tyr
1               5

<210> SEQ ID NO 25
<211> LENGTH: 9
<212> TYPE: PRT
<213> ORGANISM: Artificial Sequence
<220> FEATURE:
<223> OTHER INFORMATION: CDR domain from phage library

<400> SEQUENCE: 25

Gln Ser Tyr Asp Gly Pro Asp Leu Trp
1               5

<210> SEQ ID NO 26
<211> LENGTH: 15
<212> TYPE: PRT
<213> ORGANISM: Artificial Sequence
<220> FEATURE:
<223> OTHER INFORMATION: CDR domain from phage library

<400> SEQUENCE: 26

Gly Gly Gly Trp Val Ser His Gly Tyr Tyr Tyr Leu Phe Asp Leu
1               5                   10                  15

<210> SEQ ID NO 27
<211> LENGTH: 8
<212> TYPE: PRT
<213> ORGANISM: Artificial Sequence
<220> FEATURE:
<223> OTHER INFORMATION: CDR domain from phage library

<400> SEQUENCE: 27

Phe Gln Tyr Gly Ser Ile Pro Pro
1               5

<210> SEQ ID NO 28
<211> LENGTH: 17
<212> TYPE: PRT
<213> ORGANISM: Artificial Sequence
<220> FEATURE:
<223> OTHER INFORMATION: CDR domain from phage library

<400> SEQUENCE: 28

Ser Met Asn Ser Thr Met Tyr Trp Tyr Leu Arg Arg Val Leu Phe Asp
1               5                   10                  15

His

<210> SEQ ID NO 29
<211> LENGTH: 9
```

```
<212> TYPE: PRT
<213> ORGANISM: Artificial Sequence
<220> FEATURE:
<223> OTHER INFORMATION: CDR domain from phage library

<400> SEQUENCE: 29

Gln Ser Tyr Asp Met Tyr Met Tyr Ile
1               5

<210> SEQ ID NO 30
<211> LENGTH: 27
<212> TYPE: DNA
<213> ORGANISM: Artificial Sequence
<220> FEATURE:
<223> OTHER INFORMATION: polynucleotide sequence of CDR domain from
      phage library

<400> SEQUENCE: 30
gattttcttg gttatgagtt tgattat                                       27

<210> SEQ ID NO 31
<211> LENGTH: 27
<212> TYPE: DNA
<213> ORGANISM: Artificial Sequence
<220> FEATURE:
<223> OTHER INFORMATION: polynucleotide sequence of CDR domain from
      phage library

<400> SEQUENCE: 31
cagagctatg actattctgc tgattat                                       27

<210> SEQ ID NO 32
<211> LENGTH: 51
<212> TYPE: DNA
<213> ORGANISM: Artificial Sequence
<220> FEATURE:
<223> OTHER INFORMATION: polynucleotide sequence of CDR domain from
      phage library

<400> SEQUENCE: 32
tattatggtt cttctcttta tcattatgtt tttggtggtt ttattgatta t            51

<210> SEQ ID NO 33
<211> LENGTH: 21
<212> TYPE: DNA
<213> ORGANISM: Artificial Sequence
<220> FEATURE:
<223> OTHER INFORMATION: polynucleotide sequence of CDR domain from
      phage library

<400> SEQUENCE: 33
cagtctcatc atttttatga g                                             21

<210> SEQ ID NO 34
<211> LENGTH: 60
<212> TYPE: DNA
<213> ORGANISM: Artificial Sequence
<220> FEATURE:
<223> OTHER INFORMATION: polynucleotide sequence of CDR domain from
      phage library

<400> SEQUENCE: 34
tatcattctt ggtatgagat gggttattat ggttctactg ttggttatat gtttgattat   60

<210> SEQ ID NO 35
<211> LENGTH: 24
<212> TYPE: DNA
```

```
<213> ORGANISM: Artificial Sequence
<220> FEATURE:
<223> OTHER INFORMATION: polynucleotide sequence of CDR domain from
      phage library

<400> SEQUENCE: 35
cagagctatg actttgattt tgct                                              24

<210> SEQ ID NO 36
<211> LENGTH: 30
<212> TYPE: DNA
<213> ORGANISM: Artificial Sequence
<220> FEATURE:
<223> OTHER INFORMATION: polynucleotide sequence of CDR domain from
      phage library

<400> SEQUENCE: 36
gataattggt ttaagccttt ttctgatgtt                                        30

<210> SEQ ID NO 37
<211> LENGTH: 24
<212> TYPE: DNA
<213> ORGANISM: Artificial Sequence
<220> FEATURE:
<223> OTHER INFORMATION: polynucleotide sequence of CDR domain from
      phage library

<400> SEQUENCE: 37
cagcagtatg attctattcc ttat                                              24

<210> SEQ ID NO 38
<211> LENGTH: 30
<212> TYPE: DNA
<213> ORGANISM: Artificial Sequence
<220> FEATURE:
<223> OTHER INFORMATION: polynucleotide sequence of CDR domain from
      phage library

<400> SEQUENCE: 38
gttaatcatt ggacttatac ttttgattat                                        30

<210> SEQ ID NO 39
<211> LENGTH: 24
<212> TYPE: DNA
<213> ORGANISM: Artificial Sequence
<220> FEATURE:
<223> OTHER INFORMATION: polynucleotide sequence of CDR domain from
      phage library

<400> SEQUENCE: 39
cagcagatgt ctaattatcc tgat                                              24

<210> SEQ ID NO 40
<211> LENGTH: 51
<212> TYPE: DNA
<213> ORGANISM: Artificial Sequence
<220> FEATURE:
<223> OTHER INFORMATION: polynucleotide sequence of CDR domain from
      phage library

<400> SEQUENCE: 40
ggttattggt atgcttattt tacttatatt aattatggtt attttgataa t                51

<210> SEQ ID NO 41
<211> LENGTH: 27
<212> TYPE: DNA
<213> ORGANISM: Artificial Sequence
```

<220> FEATURE:
<223> OTHER INFORMATION: polynucleotide sequence of CDR domain from
      phage library

<400> SEQUENCE: 41
cagagctatg acaataattc tgatgtt                                              27

<210> SEQ ID NO 42
<211> LENGTH: 45
<212> TYPE: DNA
<213> ORGANISM: Artificial Sequence
<220> FEATURE:
<223> OTHER INFORMATION: polynucleotide sequence of CDR domain from
      phage library

<400> SEQUENCE: 42
ggtggtggtt gggtttctca tggttattat tatcttttg atctt                           45

<210> SEQ ID NO 43
<211> LENGTH: 24
<212> TYPE: DNA
<213> ORGANISM: Artificial Sequence
<220> FEATURE:
<223> OTHER INFORMATION: polynucleotide sequence of CDR domain from
      phage library

<400> SEQUENCE: 43
tttcagtatg gttctattcc tcct                                                 24

<210> SEQ ID NO 44
<211> LENGTH: 54
<212> TYPE: DNA
<213> ORGANISM: Artificial Sequence
<220> FEATURE:
<223> OTHER INFORMATION: polynucleotide sequence of CDR domain from
      phage library

<400> SEQUENCE: 44
acttggcagt attcttattt ttattatctt gatggtggtt attattttga tatt               54

<210> SEQ ID NO 45
<211> LENGTH: 24
<212> TYPE: DNA
<213> ORGANISM: Artificial Sequence
<220> FEATURE:
<223> OTHER INFORMATION: polynucleotide sequence of CDR domain from
      phage library

<400> SEQUENCE: 45
cagcagacta ataatgctcc tgtt                                                 24

<210> SEQ ID NO 46
<211> LENGTH: 51
<212> TYPE: DNA
<213> ORGANISM: Artificial Sequence
<220> FEATURE:
<223> OTHER INFORMATION: polynucleotide sequence of CDR domain from
      phage library

<400> SEQUENCE: 46
aatatggctt atactaatta tcagtatgtt aatatgcctc attttgatta t                   51

<210> SEQ ID NO 47
<211> LENGTH: 24
<212> TYPE: DNA
<213> ORGANISM: Artificial Sequence
<220> FEATURE:

<223> OTHER INFORMATION: polynucleotide sequence of CDR domain from
      phage library

<400> SEQUENCE: 47
cagagctatg actattttaa gctt                                         24

<210> SEQ ID NO 48
<211> LENGTH: 51
<212> TYPE: DNA
<213> ORGANISM: Artificial Sequence
<220> FEATURE:
<223> OTHER INFORMATION: polynucleotide sequence of CDR domain from
      phage library

<400> SEQUENCE: 48
tctatgaatt ctactatgta ttggtatctt cgtcgtgttc tttttgatca t           51

<210> SEQ ID NO 49
<211> LENGTH: 27
<212> TYPE: DNA
<213> ORGANISM: Artificial Sequence
<220> FEATURE:
<223> OTHER INFORMATION: polynucleotide sequence of CDR domain from
      phage library

<400> SEQUENCE: 49
cagagctatg acatgtataa ttatatt                                      27

<210> SEQ ID NO 50
<211> LENGTH: 24
<212> TYPE: DNA
<213> ORGANISM: Artificial Sequence
<220> FEATURE:
<223> OTHER INFORMATION: polynucleotide sequence of CDR domain from
      phage library

<400> SEQUENCE: 50
tcttattatc ctgattttga ttat                                         24

<210> SEQ ID NO 51
<211> LENGTH: 27
<212> TYPE: DNA
<213> ORGANISM: Artificial Sequence
<220> FEATURE:
<223> OTHER INFORMATION: polynucleotide sequence of CDR domain from
      phage library

<400> SEQUENCE: 51
cagagctatg acggtcctga tctttgg                                      27

<210> SEQ ID NO 52
<211> LENGTH: 5020
<212> TYPE: DNA
<213> ORGANISM: Artificial Sequence
<220> FEATURE:
<223> OTHER INFORMATION: polynucleotide sequence of cloning vector
<300> PUBLICATION INFORMATION:
<301> AUTHORS: Knappik et al
<302> TITLE: Fully synthetic human combinatorial antibody libraries
      (HuCAL) based on modular consensus frameworks and CDRs randomized
      with trinucleotides.
<303> JOURNAL: J Mol Biol
<304> VOLUME: 296
<305> ISSUE: 1
<306> PAGES: 57-86
<307> DATE: 2000-02-11
<308> DATABASE ACCESSION NUMBER: pubmed/10656818
<309> DATABASE ENTRY DATE: 2000-02-11
<313> RELEVANT RESIDUES: (1)..(5020)

<400> SEQUENCE: 52

```
atcgtgctga cccagccgcc ttcagtgagt ggcgcaccag gtcagcgtgt gaccatctcg      60
tgtagcggca gcagcagcaa cattggcagc aactatgtga ctggtacca gcagttgccc     120
gggacggcgc cgaaactgct gatttatgat aacaaccagc gtccctcagg cgtgccggat     180
cgttttagcg gatccaaaag cggcaccagc gcgagccttg cgattacggg cctgcaaagc     240
gaagacgaag cggattatta ttgccagagc tatgacatgc ctcaggctgt gtttggcggc     300
ggcacgaagt ttaaccgttc ttggccagcc gaaagccgca ccgagtgtga cgctgtttcc     360
gccgagcagc gaagaattgc aggcgaacaa agcgaccctg gtgtgcctga ttagcgactt     420
ttatccggga gccgtgacag tggcctggaa ggcagatagc agcccgtca aggcgggagt     480
ggagaccacc acaccctcca acaaagcaa caacaagtac gcggccagca gctatctgag     540
cctgacgcct gagcagtgga gtcccacag aagctacagc tgccaggtca cgcatgaggg     600
gagcaccgtg aaaaaaccg ttgcgccgac tgaggcctga taagcatgcg taggagaaaa     660
taaaatgaaa caaagcacta ttgcactggc actcttaccg ttgctcttca cccctgttac     720
caaagcccag gtgcaattga agaaagcgg cccggccctg gtgaaaccga cccaaaccct     780
gaccctgacc tgtaccttt ccggatttag cctgtccacg tctggcgttg gcgtgggctg     840
gattcgccag ccgcctggga aagccctcga gtggctggct ctgattgatt gggatgatga     900
taagtattat agcaccagcc tgaaaacgcg tctgaccatt agcaaagata cttcgaaaaa     960
tcaggtggtg ctgactatga ccaacatgga cccggtggga acggccacct attattgcgc    1020
gcgttctcct cgttatcgtg gtgcttttga ttattgggc caaggcaccc tggtgacggt    1080
tagctcagcg tcgaccaaag gtccaagcgt gtttccgctg gctccagca gcaaaagcac    1140
cagcggcggc acggctgccc tgggctgcct ggttaaagat tatttcccgg aaccagtcac    1200
cgtgagctgg aacagcgggg cgctgaccag cggcgtgcat acctttccgg cggtgctgca    1260
aagcagcggc ctgtatagcc tgagcagcgt tgtgaccgtg ccagcagca gcttaggcac    1320
tcagacctat atttgcaacg tgaaccataa accgagcaac accaaagtgg ataaaaaagt    1380
ggaaccgaaa agcgaattcg actataaaga tgacgatgac aaaggcgcgc cgtggagcca    1440
cccgcagttt gaaaaatgat aagcttgacc tgtgaagtga aaaatggcgc agattgtgcg    1500
acatttttt tgtctgccgt ttaattaaag ggggggggg gccggcctgg gggggggtgt    1560
acatgaaatt gtaaacgtta atattttgtt aaaattcgcg ttaaattttt gttaaatcag    1620
ctcatttttt aaccaatagg ccgaaatcgg caaaatccct tataaatcaa agaatagac    1680
cgagataggg ttgagtgttg ttccagtttg gaacaagagt ccactattaa agaacgtgga    1740
ctccaacgtc aaagggcgaa aaaccgtcta tcagggcgat ggcccactac gagaaccatc    1800
accctaatca gtttttggg ggtcgaggtg ccgtaaagca ctaaatcgga accctaaagg    1860
gagccccga tttagagctt gacggggaaa gccggcgaac gtggcgagaa aggaagggaa    1920
gaaagcgaaa ggagcgggcg ctagggcgct ggcaagtgta gcggtcacgc tgcgcgtaac    1980
caccacaccc gccgcgctta atgcgccgct acagggcgcg tgctagacta gtgtttaaac    2040
cggaccgggg gggggcttaa gtgggctgca aaacaaaacg gcctcctgtc aggaagccgc    2100
ttttatcggg tagcctcact gcccgctttc cagtcgggaa acctgtcgtg ccagctgcat    2160
cagtgaatcg gccaacgcgc ggggagaggc ggtttgcgta ttgggagcca gggtggtttt    2220
tcttttcacc agtgagacgg gcaacagctg attgcccttc accgcctggc cctgagagag    2280
```

```
ttgcagcaag cggtccacgc tggtttgccc cagcaggcga aaatcctgtt tgatggtggt    2340
cagcggcggg atataacatg agctgtcctc ggtatcgtcg tatcccacta ccgagatgtc    2400
cgcaccaacg cgcagcccgg actcggtaat ggcacgcatt gcgcccagcg ccatctgatc    2460
gttggcaacc agcatcgcag tgggaacgat gccctcattc agcatttgca tggtttgttg    2520
aaaaccggac atggcactcc agtcgccttc ccgttccgct atcggctgaa tttgattgcg    2580
agtgagatat ttatgccagc cagccagacg cagacgcgcc gagacagaac ttaatgggcc    2640
agctaacagc gcgatttgct ggtggcccaa tgcgaccaga tgctccacgc ccagtcgcgt    2700
accgtcctca tgggagaaaa taatactgtt gatgggtgtc tggtcagaga catcaagaaa    2760
taacgccgga acattagtgc aggcagcttc cacagcaata gcatcctggt catccagcgg    2820
atagttaata atcagcccac tgacacgttg cgcgagaaga ttgtgcaccg ccgctttaca    2880
ggcttcgacg ccgcttcgtt ctaccatcga cacgaccacg ctggcaccca gttgatcggc    2940
gcgagattta atcgccgcga caatttgcga cggcgcgtgc agggccagac tggaggtggc    3000
aacgccaatc agcaacgact gtttgcccgc cagttgttgt gccacgcggt taggaatgta    3060
attcagctcc gccatcgccg cttccacttt ttcccgcgtt ttcgcagaaa cgtggctggc    3120
ctggttcacc acgcgggaaa cggtctgata agagacaccg gcatactctg cgacatcgta    3180
taacgttact ggtttcacat tcaccaccct gaattgactc tcttccgggc gctatcatgc    3240
cataccgcga aaggttttgc gccattcgat gctagccatg tgagcaaaag gccagcaaaa    3300
ggccaggaac cgtaaaaagg ccgcgttgct ggcgtttttc cataggctcc gcccccctga    3360
cgagcatcac aaaaatcgac gctcaagtca gaggtggcga acccgacag gactataaag    3420 ataccaggcg tttccccctg gaagctccct cgtgcgctct cctgttccga ccctgccgct    3480
taccggatac ctgtccgcct ttctcccttc gggaagcgtg gcgctttctc atagctcacg    3540
ctgtaggtat ctcagttcgg tgtaggtcgt tcgctccaag ctgggctgtg tgcacgaacc    3600
ccccgttcag cccgaccgct gcgccttatc cggtaactat cgtcttgagt ccaacccggt    3660
aagacacgac ttatcgccac tggcagcagc cactggtaac aggattagca gagcgaggta    3720
tgtaggcggt gctacagagt tcttgaagtg gtggcctaac tacggctaca ctagaagaac    3780
agtatttggt atctgcgctc tgctgtagcc agttaccttc ggaaaaagag ttggtagctc    3840
ttgatccggc aaacaaacca ccgctggtag cggtggtttt tttgtttgca agcagcagat    3900
tacgcgcaga aaaaaaggat ctcaagaaga tcctttgatc ttttctacgg ggtctgacgc    3960
tcagtggaac gaaaactcac gttaagggat tttggtcaga tctagcacca ggcgtttaag    4020
ggcaccaata actgccttaa aaaaattacg ccccgccctg ccactcatcg cagtactgtt    4080
gtaattcatt aagcattctg ccgacatgga agccatcaca aacggcatga tgaacctgaa    4140
tcgccagcgg catcagcacc ttgtcgcctt gcgtataata tttgcccata gtgaaaacgg    4200
gggcgaagaa gttgtccata ttggctacgt ttaaatcaaa actggtgaaa ctcacccagg    4260
gattggctga gacgaaaaac atattctcaa taaacccttt agggaaatag gccaggtttt    4320
caccgtaaca cgccacatct tgcgaatata tgtgtagaaa ctgccggaaa tcgtcgtggt    4380
attcactcca gagcgatgaa aacgtttcag tttgctcatg gaaaacggtg taacaagggt    4440
gaacactatc ccatatcacc agctcaccgt ctttcattgc catacggaac tccgggtgag    4500
cattcatcag gcgggcaaga atgtgaataa aggccggata aaacttgtgc ttatttttct    4560
ttacggtctt taaaaaggcc gtaatatcca gctgaacggt ctggttatag gtacattgag    4620
caactgactg aaatgcctca aaatgttctt tacgatgcca tttgggatata tcaacggtgg    4680
```

| | | | | |
|---|---|---|---|---|
| tatatccagt | gattttttc | tccatttag | cttccttagc | tcctgaaaat ctcgataact | 4740 |
| caaaaatac | gcccggtagt | gatcttattt | cattatggtg | aaagttggaa cctcacccga | 4800 |
| cgtctaatgt | gagttagctc | actcattagg | caccccaggc | tttacactt atgcttccgg | 4860 |
| ctcgtatgtt | gtgtggaatt | gtgagcggat | aacaatttca | cacaggaaac agctatgacc | 4920 |
| atgattacga | atttctagat | aacgagggca | aaaatgaaa | aagacagcta tcgcgattgc | 4980 |
| agtggcactg | gctggtttcg | ctaccgtagc | gcaggccgat | | 5020 |

```
<210> SEQ ID NO 53
<211> LENGTH: 4151
<212> TYPE: DNA
<213> ORGANISM: Artificial Sequence
<220> FEATURE:
<223> OTHER INFORMATION: polynucleotide sequence of cloning vector
<300> PUBLICATION INFORMATION:
<301> AUTHORS: knappik et al
<302> TITLE: Fully synthetic human combinatorial antibody libraries
      (HuCAL) based on modular consensus frameworks and CDRs randomized
      with trinucleotides.
<303> JOURNAL: j mol biol
<304> VOLUME: 296
<305> ISSUE: 1
<306> PAGES: 57-86
<307> DATE: 2000-02-11
<308> DATABASE ACCESSION NUMBER: pubmed/10656818
<309> DATABASE ENTRY DATE: 2000-02-11
<313> RELEVANT RESIDUES: (1)..(4151)

<400> SEQUENCE: 53
```

| | | | | |
|---|---|---|---|---|
| tctagataac | gagggcaaaa | atgaaaaag | acagctatcg | cgattgcagt ggcactggct | 60 |
| ggtttcgcta | ccgtagcgca | ggccgatatc | gtgctgaccc | agagcccggc gaccctgagc | 120 |
| ctgtctccgg | gcgaacgtgc | gaccctgagc | tgcagagcga | gccagagcgt gagcagcagc | 180 |
| tatctggcgt | ggtaccagca | gaaaccaggt | caagcaccgc | gtctattaat ttatggcgcg | 240 |
| agcagccgtg | caactggggt | cccggcgcgt | tttagcggct | ctggatccgg cacggatttt | 300 |
| accctgacca | ttagcagcct | ggaacctgaa | gactttgcgg | tgtattattg ccagcagcat | 360 |
| tataccaccc | cgccgacctt | tggccagggt | acgaaagttg | aaattaaacg tacggtggct | 420 |
| gctccgagcg | tgttatttt | tccgccagcg | atgaacaac | tgaaaagcgg cacggcgagc | 480 |
| gtggtgtgcc | tgctgaacaa | cttttatccg | cgtgaagcga | aagttcagtg gaaagtagac | 540 |
| aacgcgctgc | aaagcggcaa | cagccaggaa | agcgtgaccg | aacaggatag caaagatagc | 600 |
| acctattctc | tgagcagcac | cctgaccctg | agcaaagcgg | attatgaaaa acataaagtg | 660 |
| tatgcgtgcg | aagtgaccca | tcaaggtctg | agcagcccgg | tgactaaaatc ttttaatcgt | 720 |
| ggcgaggcct | gataagcatg | cgtaggagaa | aataaaatga | aacaaagcac tattgcactg | 780 |
| gcactcttac | cgttgctctt | caccctgtt | accaaagccg | aagtgcaatt ggtggaaagc | 840 |
| ggcggcggcc | tggtgcaacc | gggcggcagc | ctgcgtctga | gctgcgcggc ctccggattt | 900 |
| acctttagca | gctatgcgat | gagctgggtg | cgccaagccc | ctgggaaggg tctcgagtgg | 960 |
| gtgagcgcga | ttagcggtag | cggcggcagc | acctattatg | cggatagcgt gaaaggccgt | 1020 |
| tttaccattt | cacgtgataa | ttcgaaaaac | accctgtatc | tgcaaatgaa cagcctgcgt | 1080 |
| gcggaagata | cggccgtgta | ttattgcgcg | cgttgggggcg | gcgatggctt ttatgcgatg | 1140 |
| gattattggg | gccaaggcac | cctggtgacg | gttagctcag | cgtcgaccaa aggtccaagc | 1200 |
| gtgtttccgc | tggctccgag | cagcaaaagc | accagcggcg | gcacggctgc cctgggctgc | 1260 |
| ctggttaaag | attatttccc | ggaaccagtc | accgtgagct | ggaacagcgg ggcgctgacc | 1320 |

-continued

```
agcggcgtgc ataccttttcc ggcggtgctg caaagcagcg gcctgtatag cctgagcagc   1380
gttgtgaccg tgccgagcag cagcttaggc actcagacct atatttgcaa cgtgaaccat   1440
aaaccgagca acaccaaagt ggataaaaaa gtggaaccga aaagcgaatt cgggggaggg   1500
agcgggagcg gtgattttga ttatgaaaag atggcaaacg ctaataaggg ggctatgacc   1560
gaaaatgccg atgaaaacgc gctacagtct gacgctaaag gcaaacttga ttctgtcgct   1620
actgattacg gtgctgctat cgatggtttc attggtgacg tttccggcct tgctaatggt   1680
aatggtgcta ctggtgattt tgctggctct aattcccaaa tggctcaagt cggtgacggt   1740
gataattcac ctttaatgaa taatttccgt caatatttac cttccctccc tcaatcggtt   1800
gaatgtcgcc cttttgtctt tggcgctggt aaaccatatg aattttctat tgattgtgac   1860
aaaataaact tattccgtgg tgtctttgcg tttcttttat atgttgccac ctttatgtat   1920
gtattttcta cgtttgctaa catactgcgt aataaggagt cttgataagc ttgacctgtg   1980
aagtgaaaaa tggcgcagat tgtgcgacat tttttttgtc tgccgtttaa tgaaattgta   2040
aacgttaata ttttgttaaa attcgcgtta aattttttgtt aaatcagctc attttttaac   2100
caataggccg aaatcggcaa aatcccttat aaatcaaaag aatagaccga datagggttg   2160
agtgttgttc cagtttggaa caagagtcca ctattaaaga acgtggactc caacgtcaaa   2220
gggcgaaaaa ccgtctatca gggcgatggc ccactacgag aaccatcacc ctaatcaagt   2280
tttttggggt cgaggtgccg taaagcacta atcggaacc ctaaagggag ccccgattt     2340
agagcttgac ggggaaagcc ggcgaacgtg gcgagaaagg aagggaagaa agcgaaagga   2400
gcgggcgcta gggcgctggc aagtgtagcg gtcacgctgc gcgtaaccac cacacccgcc   2460
gcgcttaatg cgccgctaca gggcgcgtgc tagccatgtg agcaaaaggc cagcaaaagg   2520
ccaggaaccg taaaaaggcc gcgttgctgg cgttttttcca taggctccgc ccccctgacg   2580
agcatcacaa aaatcgacgc tcaagtcaga ggtggcgaaa cccgacagga ctataaagat   2640
accaggcgtt tccccctgga agctccctcg tgcgctctcc tgttccgacc ctgccgctta   2700
ccggatacct gtccgccttt ctcccttcgg gaagcgtggc gctttctcat agctcacgct   2760
gtaggtatct cagttcggtg taggtcgttc gctccaagct gggctgtgtg cacgaacccc   2820
ccgttcagtc cgaccgctgc gccttatccg gtaactatcg tcttgagtcc aacccggtaa   2880
gacacgactt atcgccactg gcagcagcca ctggtaacag gattagcaga gcgaggtatg   2940
taggcggtgc tacagagttc ttgaagtggt ggcctaacta cggctacact agaagaacag   3000
tatttggtat ctgcgctctg ctgtagccag ttaccttcgg aaaagagtt ggtagctctt   3060
gatccggcaa acaaaccacc gctggtagcg gtggtttttt tgtttgcaag cagcagatta   3120
cgcgcagaaa aaaggatctc aagaagatc ctttgatctt ttctacgggg tctgacgctc   3180
agtggaacga aaactcacgt taagggattt tggtcagatc tagcaccagg cgtttaaggg   3240
caccaataac tgccttaaaa aaattacgcc ccgccctgcc actcatcgca gtactgttgt   3300
aattcattaa gcattctgcc gacatggaag ccatcacaaa cggcatgatg aacctgaatc   3360
gccagcggca tcagcacctt gtcgccttgc gtataatatt tgcccatagt gaaaacgggg   3420
gcgaagaagt tgtccatatt ggctacgttt aaatcaaaac tggtgaaact cacccaggga   3480
ttggctgaga cgaaaaacat attctcaata aacccctttag ggaaataggc caggttttca   3540
ccgtaacacg ccacatcttg cgaatatatg tgtagaaact gccggaaatc gtcgtggtat   3600
tcactccaga gcgatgaaaa cgtttcagtt tgctcatgga aaacggtgta acaagggtga   3660
```

```
acactatccc atatcaccag ctcaccgtct ttcattgcca tacggaactc cgggtgagca    3720
ttcatcaggc gggcaagaat gtgaataaag gccggataaa acttgtgctt attttttttt    3780
acggtcttta aaaggccgt aatatccagc tgaacggtct ggttataggt acattgagca    3840
actgactgaa atgcctcaaa atgttcttta cgatgccatt gggatatatc aacggtggta    3900
tatccagtga ttttttctc cattttagct tccttagctc ctgaaaatct cgataactca    3960
aaaaatacgc ccggtagtga tcttatttca ttatggtgaa agttggaacc tcacccgacg    4020
tctaatgtga gttagctcac tcattaggca ccccaggctt tacactttat gcttccggct    4080
cgtatgttgt gtggaattgt gagcggataa caatttcaca caggaaacag ctatgaccat    4140
gattacgaat t                                                         4151
```

<210> SEQ ID NO 54
<211> LENGTH: 306
<212> TYPE: DNA
<213> ORGANISM: Artificial Sequence
<220> FEATURE:
<223> OTHER INFORMATION: polynucleotide sequence of a VL domain
<220> FEATURE:
<221> NAME/KEY: misc_feature
<222> LOCATION: (253)..(255)
<223> OTHER INFORMATION: NNN=ACT OR GTT

<400> SEQUENCE: 54

```
gatatccaga tgacccagag cccgtctagc ctgagcgcga gcgtgggtga tcgtgtgacc     60
attacctgca gagcgagcca gggcattagc agctatctgg cgtggtacca gcagaaacca    120
ggtaaagcac cgaaactatt aatttatgca gccagcagct tgcaaagcgg ggtcccgtcc    180
cgttttagcg gctctggatc cggcactgat tttaccctga ccattagcag cctgcaacct    240
gaagactttg cgnnntatta ttgccagacc tttggccagg gtacgaaagt tgaaattaaa    300
cgtacg                                                              306
```

<210> SEQ ID NO 55
<211> LENGTH: 327
<212> TYPE: DNA
<213> ORGANISM: Artificial Sequence
<220> FEATURE:
<223> OTHER INFORMATION: polynucleotide sequence of a VL domain

<400> SEQUENCE: 55

```
gatatccaga tgacccagag cccgtctagc ctgagcgcga gcgtgggtga tcgtgtgacc     60
attacctgca gagcgagcca gggcattagc agctatctgg cgtggtacca gcagaaacca    120
ggtaaagcac cgaaactatt aatttatgca gccagcagct tgcaaagcgg ggtcccgtcc    180
cgttttagcg gctctggatc cggcactgat tttaccctga ccattagcag cctgcaacct    240
gaagactttg cggtttatta ttgctttcag tatggttcta ttcctcctac ctttggccag    300
ggtacgaaag ttgaaattaa acgtacg                                       327
```

<210> SEQ ID NO 56
<211> LENGTH: 309
<212> TYPE: DNA
<213> ORGANISM: Artificial Sequence
<220> FEATURE:
<223> OTHER INFORMATION: polynucleotide sequence of a VL domain
<220> FEATURE:
<221> NAME/KEY: misc_feature
<222> LOCATION: (256)..(258)
<223> OTHER INFORMATION: NNN=ACT OR GTT

<400> SEQUENCE: 56

```
gatatcgtgc tgacccagag cccggcgacc ctgagcctgt ctccgggcga acgtgcgacc    60
ctgagctgca gagcgagcca gagcgtgagc agcagctatc tggcgtggta ccagcagaaa   120
ccaggtcaag caccgcgtct attaatttat ggcgcgagca gccgtgcaac tggggtcccg   180
gcgcgtttta gcggctctgg atccggcacg gatttaccc tgaccattag cagcctggaa   240
cctgaagact ttgcgnnnta ttattgccag acctttggcc agggtacgaa agttgaaatt   300
aaacgtacg                                                          309
```

<210> SEQ ID NO 57
<211> LENGTH: 330
<212> TYPE: DNA
<213> ORGANISM: Artificial Sequence
<220> FEATURE:
<223> OTHER INFORMATION: polynucleotide sequence of a VL domain

<400> SEQUENCE: 57

```
gatatcgtgc tgacccagag cccggcgacc ctgagcctgt ctccgggcga acgtgcgacc    60
ctgagctgca gagcgagcca gagcgtgagc agcagctatc tggcgtggta ccagcagaaa   120
ccaggtcaag caccgcgtct attaatttat ggcgcgagca gccgtgcaac tggggtcccg   180
gcgcgtttta gcggctctgg atccggcacg gatttaccc tgaccattag cagcctggaa   240
cctgaagact ttgcgactta ttattgccag cagatgtcta attatcctga tacctttggc   300
cagggtacga agttgaaat taaacgtacg                                    330
```

<210> SEQ ID NO 58
<211> LENGTH: 330
<212> TYPE: DNA
<213> ORGANISM: Artificial Sequence
<220> FEATURE:
<223> OTHER INFORMATION: polynucleotide sequence of a VL domain

<400> SEQUENCE: 58

```
gatatcgtgc tgacccagag cccggcgacc ctgagcctgt ctccgggcga acgtgcgacc    60
ctgagctgca gagcgagcca gagcgtgagc agcagctatc tggcgtggta ccagcagaaa   120
ccaggtcaag caccgcgtct attaatttat ggcgcgagca gccgtgcaac tggggtcccg   180
gcgcgtttta gcggctctgg atccggcacg gatttaccc tgaccattag cagcctggaa   240
cctgaagact ttgcgactta ttattgccag cagactaata atgctcctgt tacctttggc   300
cagggtacga agttgaaat taaacgtacg                                    330
```

<210> SEQ ID NO 59
<211> LENGTH: 324
<212> TYPE: DNA
<213> ORGANISM: Artificial Sequence
<220> FEATURE:
<223> OTHER INFORMATION: polynucleotide sequence of a VL domain

<400> SEQUENCE: 59

```
gatatcgtga tgacccagag cccggatagc ctggcggtga gcctgggcga acgtgcgacc    60
attaactgca gaagcagcca gagcgtgctg tatagcagca caacaaaaa ctatctggcg   120 tggtaccagc agaaaccagg tcagccgccg aaactattaa tttattgggc atccacccgt   180
gaaagcgggg tcccggatcg ttttagcggc tctggatccg gcactgattt tacccctgacc   240 atttcgtccc tgcaagctga agacgtggcg gtgtattatt gccagacctt tggccagggt   300
acgaaagttg aaattaaacg tacg                                         324
```

<210> SEQ ID NO 60
<211> LENGTH: 345
<212> TYPE: DNA
<213> ORGANISM: Artificial Sequence
<220> FEATURE:
<223> OTHER INFORMATION: polynucleotide sequence of a VL domain

<400> SEQUENCE: 60

```
gatatcgtga tgacccagag cccggatagc ctggcggtga gcctgggcga acgtgcgacc     60
attaactgca gaagcagcca gagcgtgctg tatagcagca acaacaaaaa ctatctggcg    120
tggtaccagc agaaaccagg tcagccgccg aaactattaa tttattgggc atccacccgt    180
gaaagcgggg tcccggatcg ttttagcggc tctggatccg gcactgattt taccctgacc    240
atttcgtccc tgcaagctga agacgtggcg gtgtattatt gccagcagta tgattctatt    300
ccttatacct ttggccaggg tacgaaagtt gaaattaaac gtacg                    345
```

<210> SEQ ID NO 61
<211> LENGTH: 315
<212> TYPE: DNA
<213> ORGANISM: Artificial Sequence
<220> FEATURE:
<223> OTHER INFORMATION: polynucleotide sequence of a VL domain

<400> SEQUENCE: 61

```
gatatcgcac tgacccagcc agcttcagtg agcggctcac aggtcagag cattaccatc      60 tcgtgtacgg gtactagcag cgatgtgggc ggctataact atgtgagctg gtaccagcag    120
catcccggga aggcgccgaa actgatgatt tatgatgtga gcaaccgtcc ctcaggcgtg    180
agcaaccgtt ttagcggatc caaaagcggc aacaccgcga gcctgaccat tagcggcctg    240
caagcggaag acgaagcgga ttattattgc caggacgtgt ttggcggcgg cacgaagtta    300
accgttcttg gccag                                                     315
```

<210> SEQ ID NO 62
<211> LENGTH: 336
<212> TYPE: DNA
<213> ORGANISM: Artificial Sequence
<220> FEATURE:
<223> OTHER INFORMATION: polynucleotide sequence of a VL domain

<400> SEQUENCE: 62

```
gatatcgcac tgacccagcc agcttcagtg agcggctcac aggtcagag cattaccatc      60 tcgtgtacgg gtactagcag cgatgtgggc ggctataact atgtgagctg gtaccagcag    120
catcccggga aggcgccgaa actgatgatt tatgatgtga gcaaccgtcc ctcaggcgtg    180
agcaaccgtt ttagcggatc caaaagcggc aacaccgcga gcctgaccat tagcggcctg    240
caagcggaag acgaagcgga ttattattgc cagagctatg acatgtataa ttatattgtg    300
tttggcggcg gcacgaagtt aaccgttctt ggccag                              336
```

<210> SEQ ID NO 63
<211> LENGTH: 330
<212> TYPE: DNA
<213> ORGANISM: Artificial Sequence
<220> FEATURE:
<223> OTHER INFORMATION: polynucleotide sequence of a VL domain

<400> SEQUENCE: 63

```
gatatcgcac tgacccagcc agcttcagtg agcggctcac aggtcagag cattaccatc      60 tcgtgtacgg gtactagcag cgatgtgggc ggctataact atgtgagctg gtaccagcag    120
```

```
catcccggga aggcgccgaa actgatgatt tatgatgtga gcaaccgtcc ctcaggcgtg      180
agcaaccgtt ttagcggatc caaaagcggc aacaccgcga gcctgaccat tagcggcctg      240
caagcggaag acgaagcgga ttattattgc cagtctcatc atttttatga ggtgtttggc      300
ggcggcacga agttaaccgt tcttggccag                                       330

<210> SEQ ID NO 64
<211> LENGTH: 336
<212> TYPE: DNA
<213> ORGANISM: Artificial Sequence
<220> FEATURE:
<223> OTHER INFORMATION: polynucleotide sequence of a VL domain

<400> SEQUENCE: 64
gatatcgcac tgacccagcc agcttcagtg agcggctcac caggtcagag cattaccatc      60
tcgtgtacgg gtactagcag cgatgtgggc ggctataact atgtgagctg gtaccagcag     120
catcccggga aggcgccgaa actgatgatt tatgatgtga gcaaccgtcc ctcaggcgtg     180
agcaaccgtt ttagcggatc caaaagcggc aacaccgcga gcctgaccat tagcggcctg     240
caagcggaag acgaagcgga ttattattgc cagagctatg acaataattc tgatgttgtg     300
tttggcggcg gcacgaagtt aaccgttctt ggccag                              336

<210> SEQ ID NO 65
<211> LENGTH: 306
<212> TYPE: DNA
<213> ORGANISM: Artificial Sequence
<220> FEATURE:
<223> OTHER INFORMATION: polynucleotide sequence of a VL domain

<400> SEQUENCE: 65
gatatcgaac tgacccagcc gccttcagtg agcgttgcac aggtcagacg cgcgcgtatc      60
tcgtgtagcg gcgatgcgct gggcgataaa tacgcgagct ggtaccagca gaaacccggg     120
caggcgccag ttctggtgat ttatgatgat tctgaccgtc cctcaggcat cccggaacgc     180
tttagcggat ccaacagcgg caacaccgcg accctgacca ttagcggcac tcaggcggaa     240
gacgaagcgg attattattg ccaggacgtg tttggcggcg gcacgaagtt aaccgttctt     300
ggccag                                                                306

<210> SEQ ID NO 66
<211> LENGTH: 324
<212> TYPE: DNA
<213> ORGANISM: Artificial Sequence
<220> FEATURE:
<223> OTHER INFORMATION: polynucleotide sequence of a VL domain

<400> SEQUENCE: 66
gatatcgaac tgacccagcc gccttcagtg agcgttgcac aggtcagacg cgcgcgtatc      60
tcgtgtagcg gcgatgcgct gggcgataaa tacgcgagct ggtaccagca gaaacccggg     120
caggcgccag ttctggtgat ttatgatgat tctgaccgtc cctcaggcat cccggaacgc     180
tttagcggat ccaacagcgg caacaccgcg accctgacca ttagcggcac tcaggcggaa     240
gacgaagcgg attattattg ccagagctat gactatttta gcttgtgtt tggcggcggc     300 acgaagttaa ccgttcttgg ccag                                            324

<210> SEQ ID NO 67
<211> LENGTH: 327
<212> TYPE: DNA
```

<213> ORGANISM: Artificial Sequence
<220> FEATURE:
<223> OTHER INFORMATION: polynucleotide sequence of a VL domain

<400> SEQUENCE: 67

```
gatatcgaac tgacccagcc gccttcagtg agcgttgcac caggtcagac cgcgcgtatc    60
tcgtgtagcg gcgatgcgct gggcgataaa tacgcgagct ggtaccagca gaaacccggg   120
caggcgccag ttctggtgat ttatgatgat tctgaccgtc cctcaggcat cccggaacgc   180
tttagcggat ccaacagcgg caacaccgcg accctgacca ttagcggcac tcaggcggaa   240
gacgaagcgg attattattg ccagagctat gactattctg ctgattatgt gtttggcggc   300
ggcacgaagt taaccgttct tggccag                                       327
```

<210> SEQ ID NO 68
<211> LENGTH: 324
<212> TYPE: DNA
<213> ORGANISM: Artificial Sequence
<220> FEATURE:
<223> OTHER INFORMATION: polynucleotide sequence of a VL domain

<400> SEQUENCE: 68

```
gatatcgaac tgacccagcc gccttcagtg agcgttgcac caggtcagac cgcgcgtatc    60
tcgtgtagcg gcgatgcgct gggcgataaa tacgcgagct ggtaccagca gaaacccggg   120
caggcgccag ttctggtgat ttatgatgat tctgaccgtc cctcaggcat cccggaacgc   180
tttagcggat ccaacagcgg caacaccgcg accctgacca ttagcggcac tcaggcggaa   240
gacgaagcgg attattattg ccagagctat gactttgatt ttgctgtgtt tggcggcggc   300
acgaagttaa ccgttcttgg ccag                                          324
```

<210> SEQ ID NO 69
<211> LENGTH: 327
<212> TYPE: DNA
<213> ORGANISM: Artificial Sequence
<220> FEATURE:
<223> OTHER INFORMATION: polynucleotide sequence of a VL domain

<400> SEQUENCE: 69

```
gatatcgaac tgacccagcc gccttcagtg agcgttgcac caggtcagac cgcgcgtatc    60
tcgtgtagcg gcgatgcgct gggcgataaa tacgcgagct ggtaccagca gaaacccggg   120
caggcgccag ttctggtgat ttatgatgat tctgaccgtc cctcaggcat cccggaacgc   180
tttagcggat ccaacagcgg caacaccgcg accctgacca ttagcggcac tcaggcggaa   240
gacgaagcgg attattattg ccagagctat gacggtcctg atctttgggt gtttggcggc   300
ggcacgaagt taaccgttct tggccag                                       327
```

<210> SEQ ID NO 70
<211> LENGTH: 332
<212> TYPE: DNA
<213> ORGANISM: Artificial Sequence
<220> FEATURE:
<223> OTHER INFORMATION: polynucleotide sequence of a VH domain
<220> FEATURE:
<221> NAME/KEY: misc_feature
<222> LOCATION: (1)..(3)
<223> OTHER INFORMATION: NNN=GAA OR CAG

<400> SEQUENCE: 70

```
nnngtgcaat tggttcagtc tggcgcggaa gtgaaaaaac cgggcagcag cgtgaaagtg    60
agctgcaaag cctccggagg cactttagc agctatgcga ttagctgggt gcgccaagcc   120
```

-continued

```
cctgggcagg gtctcgagtg gatgggcggc attattccga ttttggcac ggcgaactac      180 gcgcagaagt tcagggccg ggtgaccatt accgcggatg aaagcaccag caccgcgtat      240
atggaactga gcagcctgcg tagcgaagat acggccgtgt attattgcgc gcgtgattgg      300
ggccaaggca ccctggtgac ggttagctca gc                                   332
```

<210> SEQ ID NO 71
<211> LENGTH: 359
<212> TYPE: DNA
<213> ORGANISM: Artificial Sequence
<220> FEATURE:
<223> OTHER INFORMATION: polynucleotide sequence of a VH domain

<400> SEQUENCE: 71

```
caggtgcaat tggttcagtc tggcgcggaa gtgaaaaaac cgggcagcag cgtgaaagtg      60
agctgcaaag cctccggagg cactttttagc agctatgcga ttagctgggt gcgccaagcc    120
cctgggcagg gtctcgagtg gatgggcggc attattccga ttttggcac ggcgaactac     180 gcgcagaagt tcagggccg ggtgaccatt accgcggatg aaagcaccag caccgcgtat     240
atggaactga gcagcctgcg tagcgaagat acggccgtgt attattgcgc gcgtgataat    300
tggtttaagc ctttttctga tgttttgggc caaggcaccc tggtgacggt tagctcagc      359
```

<210> SEQ ID NO 72
<211> LENGTH: 359
<212> TYPE: DNA
<213> ORGANISM: Artificial Sequence
<220> FEATURE:
<223> OTHER INFORMATION: polynucleotide sequence of a VH domain

<400> SEQUENCE: 72

```
caggtgcaat tggttcagtc tggcgcggaa gtgaaaaaac cgggcagcag cgtgaaagtg      60
agctgcaaag cctccggagg cactttttagc agctatgcga ttagctgggt gcgccaagcc    120
cctgggcagg gtctcgagtg gatgggcggc attattccga ttttggcac ggcgaactac     180 gcgcagaagt tcagggccg ggtgaccatt accgcggatg aaagcaccag caccgcgtat     240
atggaactga gcagcctgcg tagcgaagat acggccgtgt attattgcgc gcgtgttaat    300
cattggactt atacttttga ttattgggc caaggcaccc tggtgacggt tagctcagc      359
```

<210> SEQ ID NO 73
<211> LENGTH: 374
<212> TYPE: DNA
<213> ORGANISM: Artificial Sequence
<220> FEATURE:
<223> OTHER INFORMATION: polynucleotide sequence of a VH domain

<400> SEQUENCE: 73

```
caggtgcaat tggttcagtc tggcgcggaa gtgaaaaaac cgggcagcag cgtgaaagtg      60
agctgcaaag cctccggagg cactttttagc agctatgcga ttagctgggt gcgccaagcc    120
cctgggcagg gtctcgagtg gatgggcggc attattccga ttttggcac ggcgaactac     180 gcgcagaagt tcagggccg ggtgaccatt accgcggatg aaagcaccag caccgcgtat     240
atggaactga gcagcctgcg tagcgaagat acggccgtgt attattgcgc gcgtggtggt    300
ggttgggttt ctcatggtta ttattatctt tttgatcttt ggggccaagg caccctggtg    360
acggttagct cagc                                                       374
```

<210> SEQ ID NO 74

```
<211> LENGTH: 332
<212> TYPE: DNA
<213> ORGANISM: Artificial Sequence
<220> FEATURE:
<223> OTHER INFORMATION: polynucleotide sequence of a VH domain
<220> FEATURE:
<221> NAME/KEY: misc_feature
<222> LOCATION: (1)..(3)
<223> OTHER INFORMATION: NNN=GAA OR CAG

<400> SEQUENCE: 74
nnngtgcaat tggttcagag cggcgcggaa gtgaaaaaac cgggcgcgag cgtgaaagtg      60
agctgcaaag cctccggata tacctttacc agctattata tgcactgggt ccgccaagcc     120
cctgggcagg gtctcgagtg gatgggctgg attaacccga atagcggcgg cacgaactac     180
gcgcagaagt ttcagggccg ggtgaccatg acccgtgata ccagcattag caccgcgtat     240
atggaactga gcagcctgcg tagcgaagat acggccgtgt attattgcgc gcgtgattgg     300
ggccaaggca ccctggtgac ggttagctca gc                                   332

<210> SEQ ID NO 75
<211> LENGTH: 380
<212> TYPE: DNA
<213> ORGANISM: Artificial Sequence
<220> FEATURE:
<223> OTHER INFORMATION: polynucleotide sequence of a VH domain

<400> SEQUENCE: 75
caggtgcaat tggttcagag cggcgcggaa gtgaaaaaac cgggcgcgag cgtgaaagtg      60
agctgcaaag cctccggata tacctttacc agctattata tgcactgggt ccgccaagcc     120
cctgggcagg gtctcgagtg gatgggctgg attaacccga atagcggcgg cacgaactac     180
gcgcagaagt ttcagggccg ggtgaccatg acccgtgata ccagcattag caccgcgtat     240
atggaactga gcagcctgcg tagcgaagat acggccgtgt attattgcgc gcgtaatatg     300
gcttatacta attatcagta tgttaatatg cctcattttg attattgggg ccaaggcacc     360
ctggtgacgg ttagctcagc                                                 380

<210> SEQ ID NO 76
<211> LENGTH: 380
<212> TYPE: DNA
<213> ORGANISM: Artificial Sequence
<220> FEATURE:
<223> OTHER INFORMATION: polynucleotide sequence of a VH domain

<400> SEQUENCE: 76
caggtgcaat tggttcagag cggcgcggaa gtgaaaaaac cgggcgcgag cgtgaaagtg      60
agctgcaaag cctccggata tacctttacc agctattata tgcactgggt ccgccaagcc     120
cctgggcagg gtctcgagtg gatgggctgg attaacccga atagcggcgg cacgaactac     180
gcgcagaagt ttcagggccg ggtgaccatg acccgtgata ccagcattag caccgcgtat     240
atggaactga gcagcctgcg tagcgaagat acggccgtgt attattgcgc gcgttctatg     300
aattctacta tgtattggta tcttcgtcgt gttcttttg atcattgggg ccaaggcacc      360
ctggtgacgg ttagctcagc                                                 380

<210> SEQ ID NO 77
<211> LENGTH: 356
<212> TYPE: DNA
<213> ORGANISM: Artificial Sequence
<220> FEATURE:
<223> OTHER INFORMATION: polynucleotide sequence of a VH domain
```

<400> SEQUENCE: 77

```
caggtgcaat tggttcagag cggcgcggaa gtgaaaaaac cgggcgcgag cgtgaaagtg      60
agctgcaaag cctccggata tacctttacc agctattata tgcactgggt ccgccaagcc     120
cctgggcagg gtctcgagtg gatgggctgg attaacccga atagcggcgg cacgaactac     180
gcgcagaagt tcagggccg ggtgaccatg acccgtgata ccagcattag caccgcgtat      240
atggaactga gcagcctgcg tagcgaagat acggccgtgt attattgcgc gcgtgatttt     300
cttggttatg agtttgatta ttggggccaa ggcaccctgg tgacggttag ctcagc         356
```

<210> SEQ ID NO 78
<211> LENGTH: 380
<212> TYPE: DNA
<213> ORGANISM: Artificial Sequence
<220> FEATURE:
<223> OTHER INFORMATION: polynucleotide sequence of a VH domain

<400> SEQUENCE: 78

```
caggtgcaat tggttcagag cggcgcggaa gtgaaaaaac cgggcgcgag cgtgaaagtg      60
agctgcaaag cctccggata tacctttacc agctattata tgcactgggt ccgccaagcc     120
cctgggcagg gtctcgagtg gatgggctgg attaacccga atagcggcgg cacgaactac     180
gcgcagaagt tcagggccg ggtgaccatg acccgtgata ccagcattag caccgcgtat      240
atggaactga gcagcctgcg tagcgaagat acggccgtgt attattgcgc gcgttattat     300
ggttcttctc tttatcatta tgttttggt ggttttattg attattgggg ccaaggcacc      360
ctggtgacgg ttagctcagc                                                 380
```

<210> SEQ ID NO 79
<211> LENGTH: 380
<212> TYPE: DNA
<213> ORGANISM: Artificial Sequence
<220> FEATURE:
<223> OTHER INFORMATION: polynucleotide sequence of a VH domain

<400> SEQUENCE: 79

```
caggtgcaat tggttcagag cggcgcggaa gtgaaaaaac cgggcgcgag cgtgaaagtg      60
agctgcaaag cctccggata tacctttacc agctattata tgcactgggt ccgccaagcc     120
cctgggcagg gtctcgagtg gatgggctgg attaacccga atagcggcgg cacgaactac     180
gcgcagaagt tcagggccg ggtgaccatg acccgtgata ccagcattag caccgcgtat      240
atggaactga gcagcctgcg tagcgaagat acggccgtgt attattgcgc gcgtggttat     300
tggtatgctt attttactta tattaattat ggttattttg ataattgggg ccaaggcacc     360
ctggtgacgg ttagctcagc                                                 380
```

<210> SEQ ID NO 80
<211> LENGTH: 383
<212> TYPE: DNA
<213> ORGANISM: Artificial Sequence
<220> FEATURE:
<223> OTHER INFORMATION: polynucleotide sequence of a VH domain

<400> SEQUENCE: 80

```
caggtgcaat tggttcagag cggcgcggaa gtgaaaaaac cgggcgcgag cgtgaaagtg      60
agctgcaaag cctccggata tacctttacc agctattata tgcactgggt ccgccaagcc     120
cctgggcagg gtctcgagtg gatgggctgg attaacccga atagcggcgg cacgaactac     180
```

```
gcgcagaagt tcagggccg ggtgaccatg acccgtgata ccagcattag caccgcgtat    240
atggaactga gcagcctgcg tagcgaagat acggccgtgt attattgcgc gcgtacttgg    300
cagtattctt attttatta tcttgatggt ggttattatt ttgatatttg gggccaaggc    360
accctggtga cggttagctc agc                                            383

<210> SEQ ID NO 81
<211> LENGTH: 335
<212> TYPE: DNA
<213> ORGANISM: Artificial Sequence
<220> FEATURE:
<223> OTHER INFORMATION: polynucleotide sequence of a VH domain
<220> FEATURE:
<221> NAME/KEY: misc_feature
<222> LOCATION: (1)..(3)
<223> OTHER INFORMATION: NNN=GAA OR CAG

<400> SEQUENCE: 81
nnngtgcaat tgaaagaaag cggcccggcc ctggtgaaac cgacccaaac cctgaccctg    60
acctgtacct tttccggatt tagcctgtcc acgtctggcg ttggcgtggg ctggattcgc   120
cagccgcctg ggaaagccct cgagtggctg gctctgattg attgggatga tgataagtat   180
tatagcacca gcctgaaaac gcgtctgacc attagcaaag atacttcgaa aaatcaggtg   240
gtgctgacta tgaccaacat ggaccgggtg gatacggcca ctattattg cgcgcgtgat   300 tggggccaag gcaccctggt gacggttagc tcagc                              335

<210> SEQ ID NO 82
<211> LENGTH: 392
<212> TYPE: DNA
<213> ORGANISM: Artificial Sequence
<220> FEATURE:
<223> OTHER INFORMATION: polynucleotide sequence of a VH domain

<400> SEQUENCE: 82
caggtgcaat tgaaagaaag cggcccggcc ctggtgaaac cgacccaaac cctgaccctg    60
acctgtacct tttccggatt tagcctgtcc acgtctggcg ttggcgtggg ctggattcgc   120
cagccgcctg ggaaagccct cgagtggctg gctctgattg attgggatga tgataagtat   180
tatagcacca gcctgaaaac gcgtctgacc attagcaaag atacttcgaa aaatcaggtg   240
gtgctgacta tgaccaacat ggaccgggtg gatacggcca ctattattg cgcgcgttat   300 cattcttggt atgagatggg ttattatggt tctactgttg gttatatgtt tgattattgg   360
ggccaaggca ccctggtgac ggttagctca gc                                 392

<210> SEQ ID NO 83
<211> LENGTH: 341
<212> TYPE: DNA
<213> ORGANISM: Artificial Sequence
<220> FEATURE:
<223> OTHER INFORMATION: polynucleotide sequence of a VH domain
<220> FEATURE:
<221> NAME/KEY: misc_feature
<222> LOCATION: (1)..(3)
<223> OTHER INFORMATION: NNN=GAA OR CAG

<400> SEQUENCE: 83
nnngtgcaat tgcaacagtc tggtccgggc ctggtgaaac cgagccaaac cctgagcctg    60
acctgtgcga tttccggaga tagcgtgagc agcaacagcg cggcgtggaa ctggattcgc   120
cagtctcctg ggcgtggcct cgagtggctg ggccgtacct attatcgtag caaatgtat   180 aacgattatg cggtgagcgt gaaaagccgg attaccatca cccggatac ttcgaaaaac   240
```
cagtttagcc tgcaactgaa cagcgtgacc ccggaagata cggccgtgta ttattgcgcg    300
cgtgattggg gccaaggcac cctggtgacg gttagctcag c    341

<210> SEQ ID NO 84
<211> LENGTH: 362
<212> TYPE: DNA
<213> ORGANISM: Artificial Sequence
<220> FEATURE:
<223> OTHER INFORMATION: polynucleotide sequence of a VH domain

<400> SEQUENCE: 84
caggtgcaat tgcaacagtc tggtccgggc ctggtgaaac cgagccaaac cctgagcctg    60
acctgtgcga tttccggaga tagcgtgagc agcaacagcg cggcgtggaa ctggattcgc    120
cagtctcctg gccgtggcct cgagtggctg ggccgtacct attatcgtag caaatggtat    180
aacgattatg cggtgagcgt gaaaagccgg attaccatca acccggatac ttcgaaaaac    240
cagtttagcc tgcaactgaa cagcgtgacc ccggaagata cggccgtgta ttattgcgcg    300
cgttcttatt atcctgattt tgattattgg ggccaaggca ccctggtgac ggttagctca    360
gc    362

<210> SEQ ID NO 85
<211> LENGTH: 109
<212> TYPE: PRT
<213> ORGANISM: Artificial Sequence
<220> FEATURE:
<223> OTHER INFORMATION: polypeptide sequence of a VL domain

<400> SEQUENCE: 85

Asp Ile Glu Leu Thr Gln Pro Pro Ser Val Ser Val Ala Pro Gly Gln
1               5                   10                  15

Thr Ala Arg Ile Ser Cys Ser Gly Asp Ala Leu Gly Asp Lys Tyr Ala
            20                  25                  30

Ser Trp Tyr Gln Gln Lys Pro Gly Gln Ala Pro Val Leu Val Ile Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Tyr Ser Ala Asp Tyr
                85                  90                  95

Val Phe Gly Gly Gly Thr Lys Leu Thr Val Leu Gly Gln
            100                 105

<210> SEQ ID NO 86
<211> LENGTH: 110
<212> TYPE: PRT
<213> ORGANISM: Artificial Sequence
<220> FEATURE:
<223> OTHER INFORMATION: polypeptide sequence of a VL domain

<400> SEQUENCE: 86

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

```
Met Ile Tyr Asp Val Ser Asn Arg Pro Ser Gly Val Ser Asn Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser His His Phe Tyr
                 85                  90                  95

Glu Val Phe Gly Gly Gly Thr Lys Leu Thr Val Leu Gly Gln
             100                 105                 110

<210> SEQ ID NO 87
<211> LENGTH: 108
<212> TYPE: PRT
<213> ORGANISM: Artificial Sequence
<220> FEATURE:
<223> OTHER INFORMATION: polypeptide sequence of a VL domain

<400> SEQUENCE: 87

Asp Ile Glu Leu Thr Gln Pro Pro Ser Val Ser Val Ala Pro Gly Gln
 1               5                  10                  15

Thr Ala Arg Ile Ser Cys Ser Gly Asp Ala Leu Gly Asp Lys Tyr Ala
                 20                  25                  30

Ser Trp Tyr Gln Gln Lys Pro Gly Gln Ala Pro Val Leu Val Ile Tyr
             35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Tyr Asp Phe Asp Phe Ala Val
                 85                  90                  95

Phe Gly Gly Gly Thr Lys Leu Thr Val Leu Gly Gln
             100                 105

<210> SEQ ID NO 88
<211> LENGTH: 115
<212> TYPE: PRT
<213> ORGANISM: Artificial Sequence
<220> FEATURE:
<223> OTHER INFORMATION: polypeptide sequence of a VL domain

<400> SEQUENCE: 88

Asp Ile Val Met Thr Gln Ser Pro Asp Ser Leu Ala Val Ser Leu Gly
 1               5                  10                  15

Glu Arg Ala Thr Ile Asn Cys Arg Ser Ser Gln Ser Val Leu Tyr Ser
                 20                  25                  30

Ser Asn Asn Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Asp Ser Ile Pro Tyr Thr Phe Gly Gln Gly Thr Lys Val Glu Ile
             100                 105                 110

Lys Arg Thr
     115

<210> SEQ ID NO 89
```

<211> LENGTH: 110
<212> TYPE: PRT
<213> ORGANISM: Artificial Sequence
<220> FEATURE:
<223> OTHER INFORMATION: polypeptide sequence of a VL domain

<400> SEQUENCE: 89

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Met Ser Asn Tyr Pro
                85                  90                  95

Asp Thr Phe Gly Gln Gly Thr Lys Val Glu Ile Lys Arg Thr
            100                 105                 110
```

<210> SEQ ID NO 90
<211> LENGTH: 112
<212> TYPE: PRT
<213> ORGANISM: Artificial Sequence
<220> FEATURE:
<223> OTHER INFORMATION: polypeptide sequence of a VL domain

<400> SEQUENCE: 90

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Asn Asn
                85                  90                  95

Ser Asp Val Val Phe Gly Gly Gly Thr Lys Leu Thr Val Leu Gly Gln
            100                 105                 110
```

<210> SEQ ID NO 91
<211> LENGTH: 109
<212> TYPE: PRT
<213> ORGANISM: Artificial Sequence
<220> FEATURE:
<223> OTHER INFORMATION: polypeptide sequence of a VL domain

<400> SEQUENCE: 91

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Val Tyr Tyr Cys Phe Gln Tyr Gly Ser Ile Pro Pro
                 85                  90                  95

Thr Phe Gly Gln Gly Thr Lys Val Glu Ile Lys Arg Thr
            100                 105

<210> SEQ ID NO 92
<211> LENGTH: 110
<212> TYPE: PRT
<213> ORGANISM: Artificial Sequence
<220> FEATURE:
<223> OTHER INFORMATION: polypeptide sequence of a VL domain

<400> SEQUENCE: 92

Asp Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Val Pro Ala Arg Phe Ser
         50                  55                  60

Gly Ser Gly Ser Gly Thr Asp Phe Thr Leu Thr Ile Ser Ser Leu Glu
 65                  70                  75                  80

Pro Glu Asp Phe Ala Thr Tyr Tyr Cys Gln Gln Thr Asn Asn Ala Pro
                 85                  90                  95

Val Thr Phe Gly Gln Gly Thr Lys Val Glu Ile Lys Arg Thr
            100                 105                 110

<210> SEQ ID NO 93
<211> LENGTH: 108
<212> TYPE: PRT
<213> ORGANISM: Artificial Sequence
<220> FEATURE:
<223> OTHER INFORMATION: polypeptide sequence of a VL domain

<400> SEQUENCE: 93

Asp Ile Glu Leu Thr Gln Pro Pro Ser Val Ser Val Ala Pro Gly Gln
  1               5                  10                  15

Thr Ala Arg Ile Ser Cys Ser Gly Asp Ala Leu Gly Asp Lys Tyr Ala
                 20                  25                  30

Ser Trp Tyr Gln Gln Lys Pro Gly Gln Ala Pro Val Leu Val Ile Tyr
             35                  40                  45

Asp Asp Ser Asp Arg Pro Ser Gly Ile Pro Glu Arg Phe Ser Gly Ser
         50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Tyr Asp Tyr Phe Lys Leu Val
                 85                  90                  95

Phe Gly Gly Gly Thr Lys Leu Thr Val Leu Gly Gln
            100                 105

<210> SEQ ID NO 94
<211> LENGTH: 112
<212> TYPE: PRT
<213> ORGANISM: Artificial Sequence
```

```
<220> FEATURE:
<223> OTHER INFORMATION: polypeptide sequence of a VL domain

<400> SEQUENCE: 94

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Met Tyr
                85                  90                  95

Asn Tyr Ile Val Phe Gly Gly Gly Thr Lys Leu Thr Val Leu Gly Gln
            100                 105                 110

<210> SEQ ID NO 95
<211> LENGTH: 109
<212> TYPE: PRT
<213> ORGANISM: Artificial Sequence
<220> FEATURE:
<223> OTHER INFORMATION: polypeptide sequence of a VL domain

<400> SEQUENCE: 95

Asp Ile Glu Leu Thr Gln Pro Pro Ser Val Ser Val Ala Pro Gly Gln
1               5                   10                  15

Thr Ala Arg Ile Ser Cys Ser Gly Asp Ala Leu Gly Asp Lys Tyr Ala
                20                  25                  30

Ser Trp Tyr Gln Gln Lys Pro Gly Gln Ala Pro Val Leu Val Ile Tyr
            35                  40                  45

Asp Asp Ser Asp Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Gly Pro Asp Leu Trp
                85                  90                  95

Val Phe Gly Gly Gly Thr Lys Leu Thr Val Leu Gly Gln
            100                 105

<210> SEQ ID NO 96
<211> LENGTH: 118
<212> TYPE: PRT
<213> ORGANISM: Artificial Sequence
<220> FEATURE:
<223> OTHER INFORMATION: polypeptide sequence of a VH domain

<400> SEQUENCE: 96

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
50                  55                  60
```

```
Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Phe Leu Gly Tyr Glu Phe Asp Tyr Trp Gly Gln Gly Thr
            100                 105                 110

Leu Val Thr Val Ser Ser
            115
```

<210> SEQ ID NO 97
<211> LENGTH: 126
<212> TYPE: PRT
<213> ORGANISM: Artificial Sequence
<220> FEATURE:
<223> OTHER INFORMATION: polypeptide sequence of a VH domain

<400> SEQUENCE: 97

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Tyr Gly Ser Ser Leu Tyr His Tyr Val Phe Gly Gly Phe
            100                 105                 110

Ile Asp Tyr Trp Gly Gln Gly Thr Leu Val Thr Val Ser Ser
            115                 120                 125
```

<210> SEQ ID NO 98
<211> LENGTH: 130
<212> TYPE: PRT
<213> ORGANISM: Artificial Sequence
<220> FEATURE:
<223> OTHER INFORMATION: polypeptide sequence of a VH domain

<400> SEQUENCE: 98

```
Gln Val Gln Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
             20                  25                  30

Gly Val Gly Val Gly Trp Ile Arg Gln Pro Pro Gly Lys Ala Leu Glu
         35                  40                  45

Trp Leu Ala Leu Ile Asp Trp Asp Asp Asp Lys Tyr Tyr Ser Thr Ser
     50                  55                  60

Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Tyr His Ser Trp Tyr Glu Met Gly Tyr Tyr Gly Ser Thr
            100                 105                 110

Val Gly Tyr Met Phe Asp Tyr Trp Gly Gln Gly Thr Leu Val Thr Val
            115                 120                 125
```

Ser Ser
    130

<210> SEQ ID NO 99
<211> LENGTH: 119
<212> TYPE: PRT
<213> ORGANISM: Artificial Sequence
<220> FEATURE:
<223> OTHER INFORMATION: polypeptide sequence of a VH domain

<400> SEQUENCE: 99

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asn Trp Phe Lys Pro Phe Ser Asp Val Trp Gly Gln Gly
            100                 105                 110

Thr Leu Val Thr Val Ser Ser
        115

<210> SEQ ID NO 100
<211> LENGTH: 119
<212> TYPE: PRT
<213> ORGANISM: Artificial Sequence
<220> FEATURE:
<223> OTHER INFORMATION: polypeptide sequence of a VH domain

<400> SEQUENCE: 100

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn His Trp Thr Tyr Thr Phe Asp Tyr Trp Gly Gln Gly
            100                 105                 110

Thr Leu Val Thr Val Ser Ser
        115

<210> SEQ ID NO 101
<211> LENGTH: 126
<212> TYPE: PRT
<213> ORGANISM: Artificial Sequence
<220> FEATURE:
<223> OTHER INFORMATION: polypeptide sequence of a VH domain

```
<400> SEQUENCE: 101

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Trp Tyr Ala Tyr Phe Thr Tyr Ile Asn Tyr Gly Tyr
                100                 105                 110

Phe Asp Asn Trp Gly Gln Gly Thr Leu Val Thr Val Ser Ser
            115                 120                 125

<210> SEQ ID NO 102
<211> LENGTH: 124
<212> TYPE: PRT
<213> ORGANISM: Artificial Sequence
<220> FEATURE:
<223> OTHER INFORMATION: polypeptide sequence of a VH domain

<400> SEQUENCE: 102

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Trp Val Ser His Gly Tyr Tyr Tyr Leu Phe Asp
                100                 105                 110

Leu Trp Gly Gln Gly Thr Leu Val Thr Val Ser Ser
            115                 120

<210> SEQ ID NO 103
<211> LENGTH: 127
<212> TYPE: PRT
<213> ORGANISM: Artificial Sequence
<220> FEATURE:
<223> OTHER INFORMATION: polypeptide sequence of a VH domain

<400> SEQUENCE: 103

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45
```

Gly Trp Ile Asn Pro Asn Ser Gly Gly Thr Asn Tyr Ala Gln Lys Phe
            50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Thr Trp Gln Tyr Ser Tyr Phe Tyr Leu Asp Gly Gly Tyr
            100                 105                 110

Tyr Phe Asp Ile Trp Gly Gln Gly Thr Leu Val Thr Val Ser Ser
            115                 120                 125

<210> SEQ ID NO 104
<211> LENGTH: 126
<212> TYPE: PRT
<213> ORGANISM: Artificial Sequence
<220> FEATURE:
<223> OTHER INFORMATION: polypeptide sequence of a VH domain

<400> SEQUENCE: 104

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
             35                  40                  45

Gly Trp Ile Asn Pro Asn Ser Gly Gly Thr Asn Tyr Ala Gln Lys Phe
            50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Met Ala Tyr Thr Asn Tyr Gln Tyr Val Asn Met Pro His
            100                 105                 110

Phe Asp Tyr Trp Gly Gln Gly Thr Leu Val Thr Val Ser Ser
            115                 120                 125

<210> SEQ ID NO 105
<211> LENGTH: 126
<212> TYPE: PRT
<213> ORGANISM: Artificial Sequence
<220> FEATURE:
<223> OTHER INFORMATION: polypeptide sequence of a VH domain

<400> SEQUENCE: 105

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
             35                  40                  45

Gly Trp Ile Asn Pro Asn Ser Gly Gly Thr Asn Tyr Ala Gln Lys Phe
            50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Met Asn Ser Thr Met Tyr Trp Tyr Leu Arg Arg Val Leu

-continued

```
                100             105             110
Phe Asp His Trp Gly Gln Gly Thr Leu Val Thr Val Ser Ser
            115             120             125

<210> SEQ ID NO 106
<211> LENGTH: 120
<212> TYPE: PRT
<213> ORGANISM: Artificial Sequence
<220> FEATURE:
<223> OTHER INFORMATION: polypeptide sequence of a VH domain

<400> SEQUENCE: 106

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Gly Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Ser Tyr Tyr Pro Asp Phe Asp Tyr Trp Gly Gln
            100                 105                 110

Gly Thr Leu Val Thr Val Ser Ser
            115                 120
```

ANTIBODIES THAT BLOCK RECEPTOR PROTEIN TYROSINE KINASE ACTIVATION, METHODS OF SCREENING FOR AND USES THEREOF

CROSS-REFERENCE TO RELATED APPLICATIONS

This application is a continuation of International Application No. PCT/IL02/00494 filed Jun. 20, 2002, the content of which is expressly incorporated herein by reference thereto, and which claims the benefit of U.S. Provisional Application No. 60/299,187 filed Jun. 20, 2001.

FIELD OF THE INVENTION

The present invention relates to immunoglobulins and functional fragments thereof useful for blocking activation of receptor protein tyrosine kinases, methods for screening for such immunoglobulins, compositions comprising said immunoglobulins and methods of using the same for treating or inhibiting disease, such as skeletal dysplasia, craniosynostosis disorders, cell proliferative diseases or disorders, or tumor progression.

BACKGROUND OF THE INVENTION

A wide variety of biological processes involves complex cellular communication mechanisms. One of the primary means of continual exchange of information between cells and their internal and external environments is via the secretion and specific binding of peptide growth factors. Growth factors exert pleiotropic effects and play important roles in oncogenesis and the development of multicellular organisms regulating cell growth, differentiation and migration. Many of these factors mediate their effects by binding to specific cell surface receptors. The ligand-activated receptors start an enzymatic signal transduction cascade from the cell membrane to the cell nucleus, resulting in specific gene regulation and diverse cellular responses.

Protein Kinases

One of the key biochemical mechanisms of signal transduction involves the reversible phosphorylation of proteins, which enables regulation of the activity of mature proteins by altering their structure and function.

Protein kinases ("PKs") are enzymes that catalyze the phosphorylation of hydroxy groups on tyrosine, serine and threonine residues of proteins. The consequences of this seemingly simple activity are staggering; cell growth, differentiation and proliferation; e.g., virtually all aspects of cell life in one way or another depend on PK activity. Furthermore, abnormal PK activity has been related to a host of disorders, ranging from relatively non-life threatening diseases such as psoriasis to extremely virulent diseases such as glioblastoma.

The kinases fall largely into two groups, those specific for phosphorylating serine and threonine, and those specific for phosphorylating tyrosine. Some kinases, referred to as "dual specificity" kinases, are able to phosphorylate tyrosine as well as serine/threonine residues.

Protein kinases can also be characterized by their location within the cell. Some kinases are transmembrane receptor proteins capable of binding ligands external to the cell membrane. Binding the ligands alters the receptor protein kinase's catalytic activity. Others are non-receptor proteins lacking a transmembrane domain and yet others are ecto-kinases that have a catalytic domain on the extracellular (ecto) portion of a transmembrane protein or which are secreted as soluble extracellular proteins.

Many kinases are involved in regulatory cascades where their substrates may include other kinases whose activities are regulated by their phosphorylation state. Thus, activity of a downstream effector is modulated by phosphorylation resulting from activation of the pathway.

Receptor protein tyrosine kinases (RPTKs) are a subclass of transmembrane-spanning receptors endowed with intrinsic, ligand-stimulatable tyrosine kinase activity. RPTK activity is tightly controlled. When mutated or altered structurally, RPTKs can become potent oncoproteins, causing cellular transformation. In principle, for all RPTKs involved in cancer, oncogenic deregulation results from relief or perturbation of one or several of the auto-control mechanisms that ensure the normal repression of catalytic domains. More than half of the known RPTKs have been repeatedly found in either mutated or overexpressed forms associated with human malignancies (including sporadic cases; Blume-Jensen et al., 2001). RPTK overexpression leads to constitutive kinase activation by increasing the concentration of dimers. Examples are Neu/ErbB2 and epidermal growth factor receptor (EGFR), which are often amplified in breast and lung carcinomas and the fibroblast growth factors (FGFR) associated with skeletal and proliferative disorders (Blume-Jensen et al., 2001).

Fibroblast Growth Factors

Normal growth, as well as tissue repair and remodeling, require specific and delicate control of activating growth factors and their receptors. Fibroblast Growth Factors (FGFs) constitute a family of over twenty structurally related polypeptides that are developmentally regulated and expressed in a wide variety of tissues. FGFs stimulate proliferation, cell migration and differentiation and play a major role in skeletal and limb development, wound healing, tissue repair, hematopoiesis, angiogenesis, and tumorigenesis (reviewed in Ornitz and Itoh, 2001).

The biological action of FGFs is mediated by specific cell surface receptors belonging to the RPTK family of protein kinases. These proteins consist of an extracellular ligand binding domain, a single transmembrane domain and an intracellular tyrosine kinase domain which undergoes phosphorylation upon binding of FGF. The FGF receptor (FGFR) extracellular region contains three immunoglobulin-like (Ig-like) loops or domains (D1, D2 and D3), an acidic box, and a heparin binding domain. Five FGFR genes that encode for multiple receptor protein variants have been identified to date.

Another major class of cell surface binding sites includes binding sites for heparan sulfate proteoglycans (HSPG) that are required for high affinity interaction and activation of all members of the FGF family. Tissue-specific expression of heparan sulfate structural variants confer ligand-receptor specificity and activity of FGFs.

FGFR-Related Disease

Recent discoveries show that a growing number of skeletal abnormalities, including achondroplasia, the most common form of human dwarfism, result from mutations in FGFRs. Specific point mutations in different domains of FGFR3 are associated with autosomal dominant human skeletal disorders including hypochondroplasia, severe achondroplasia with developmental delay and acanthosis nigricans (SADDAN) and thanatophoric dysplasia (TD) (Cappellen et al., 1999; Webster et al., 1997; Tavormina et al.,1999). FGFR3 mutations have also been described in two craniosynostosis phenotypes: Muenke coronal craniosynostosis (Bellus et al., 1996; Muenke et al., 1997) and Crouzon syndrome with acanthosis nigricans (Meyers et al., 1995). Crouzon syndrome is associated with specific point mutations in FGFR2 and both familial and sporadic forms of Pfeiffer syndrome are associated with mutations in FGFR1 and FGFR2 (Galvin et al., 1996; Schell et al., 1995). Mutations in FGFRs result in constitutive activation of the mutated receptors and increased receptor protein tyrosine kinase activity, rendering cells and tissue unable to differentiate. Specifically, the achondroplasia mutation results in enhanced stability of the mutated receptor, dissociating receptor activation from down-regulation, leading to restrained chondrocyte maturation and bone growth inhibition (reviewed in Vajo et al., 2000).

There is accumulating evidence for mutations activating FGFR3 in various types of cancer. Constitutively activated FGFR3 in a large proportion of two common epithelial cancers, bladder and cervix, as well as in multiple myeloma, is the first evidence of an oncogenic role for FGFR3 in carcinomas. FGFR3 currently appears to be the most frequently mutated oncogene in bladder cancer where it is mutated in almost 50% of the cases and in about 70% of cases having recurrent superficial bladder tumors (Cappellen, et al, 1999; van Rhijn, et al, 2001; Billerey, et al, 2001). FGFR3 mutations are seen in 15-20% of multiple myeloma cases where point mutations that cause constitutive activation directly contribute to tumor development and progression (Chesi, et al, 1997; Plowright, et al, 2000, Ronchetti, et al, 2001).

In this context, the consequences of FGFR3 signaling appear to be cell type-specific. In chondrocytes, FGFR3 hyperactivation results in growth inhibition (reviewed in Ornitz, 2001), whereas in the myeloma cell it contributes to tumor progression (Chesi et al., 2001).

In view of the link between RPTK-related cellular activities and a number of human disorders various strategies have been employed to target the receptors and/or their variants for therapy. Some of these have involved biomimetic approaches using large molecules patterned on those involved in the cellular processes, e.g., mutant ligands (U.S. Pat. No. 4,966,849); soluble receptors and antibodies (WO 94/10202, U.S. Pat. No. 6,342,219); RNA ligands (U.S. Pat. No. 5,459,015) and tyrosine kinase inhibitors (WO 94/14808; U.S. Pat. No. 5,330,992).

Antibody Therapy

The search for new therapies to treat cancer and other diseases associated with growth factors and their corresponding cell surface receptors has resulted in the development of humanized antibodies capable of inhibiting receptor function. For example, U.S. Pat. Nos. 5,942,602 and 6,365,157 disclose monoclonal antibodies specific for the HER2/neu and VEGF receptors, respectively. U.S. Pat. No. 5,840,301 discloses a chimeric, humanized monoclonal antibody that binds to the extracellular domain of VEGF and neutralizes ligand-dependent activation. U.S. Pat. No. 5,707,632 discloses a method for producing an antibody to a FGFR and a monoclonal antibody to FGFR that blocks binding of fibroblast growth factor to said fibroblast growth factor receptor sequences.

There remains an unmet need for highly selective molecules capable of blocking aberrant constitutive receptor protein tyrosine kinase activity, in particular FGFR activity, thereby addressing the clinical manifestations associated with the above-mentioned mutations, and modulating various biological functions.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

In one aspect the present invention provides molecules which are able to block receptor protein tyrosine kinase (RPTK) activity.

In another aspect the present invention provides molecules which are able to block fibroblast growth factor receptor (FGFR) activity, preferably fibroblast growth factor receptor 3 (FGFR3) activity.

In yet another aspect the present invention provides polypeptides encoding molecules which are able to block receptor protein tyrosine kinase (RPTK) activity, preferably FGFR activity, and more preferably FGFR3 activity.

In a further aspect the present invention provides a method to screen for molecules which are able to block receptor protein tyrosine kinase activity.

In one aspect the present invention provides a pharmaceutical composition comprising as an active ingredient a therapeutically effective amount of molecules of the invention useful in treating or preventing skeletal and proliferative diseases and disorders.

In another aspect the present invention provides a method for inhibiting growth of tumor cells associated with ligand-dependent or constitutive activation of a RPTK. According to one embodiment the RPTK is a fibroblast growth factor receptor. According to another embodiment the RPTK is FGFR3.

In yet a further aspect the present invention provides a method for treating skeletal disorders associated with ligand-dependent or constitutive activation of a RPTK. According to one embodiment the RPTK is a fibroblast growth factor receptor. According to another embodiment the RPTK is FGFR3.

In one aspect the present invention provides a method for blocking receptor protein tyrosine kinase activation in the cells of patients in need thereof by treatment with molecules capable of inhibiting receptor protein tyrosine kinase function.

In yet another aspect the present invention provides a method for inhibiting tumor growth, tumor progression or metastases.

In yet another aspect the present invention provides molecules useful for in vivo imaging of diseased states. In yet another aspect the present invention provides a kit comprising molecules of the invention. For example, a kit would comprise an antigen binding molecule of the invention and at least one reagent suitable for detecting the presence of said molecule when bound to said receptor protein tyrosine kinase and instructions for use.

These and other aspects are met by the invention disclosed herein.

The present invention provides a molecule comprising the antigen-binding portion of an antibody which has a specific affinity for a receptor protein tyrosine kinase (RPTK) and which blocks ligand-independent (constitutive activation) of a receptor protein tyrosine kinase. The present invention further provides a molecule that comprises the antigen-binding portion of an antibody which has a specific affinity for a receptor protein tyrosine kinase and which blocks ligand-dependent activation of a fibroblast growth factor receptor (FGFR), including FGFR1 and FGFR3.

Certain mutations in the genes of receptor protein tyrosine kinases result in activation of the receptor in a manner that is independent of the presence of a ligand. Such ligand-independent, or constitutive, receptor protein tyrosine kinase activation results in increased receptor activity. The clinical manifestations of certain mutations in fibroblast growth factor receptors (FGFR) are skeletal and proliferative disorders and diseases, including achondroplasia and various cancers.

Specific molecules of the present invention were found to inhibit or block constitutive activation of the FGFR3. Generation of inhibitory molecules would be useful for developing medicaments for use in treating or preventing skeletal and proliferative diseases and disorders associated with constitutive activation of receptor protein tyrosine kinases.

The present invention is directed to novel molecules comprising an antigen binding domain which binds to a receptor protein tyrosine kinase and blocks constitutive activation of said receptor protein tyrosine kinase. The molecules of the invention maybe antibodies or antigen binding fragments thereof.

One embodiment of the present invention provides a molecule which binds to the extracellular domain of a receptor protein tyrosine kinase and blocks constitutive and ligand-dependent activation of the receptor.

A currently more preferred embodiment of the present invention provides a molecule which binds to the extracellular domain of an FGF receptor and blocks constitutive and ligand-dependent activation of the receptor.

A currently most preferred embodiment of the present invention provides a molecule which binds FGFR3 and blocks constitutive and ligand-dependent activation of the receptor, comprising $V_L$-CDR3 and $V_H$-CDR3 regions having amino acid SEQ ID NO:25 and SEQ ID NO:24, respectively and the corresponding isolated nucleic acid molecules comprising polynucleotide sequence SEQ ID NO:51 and SEQ ID NO:50.

A currently most preferred embodiment of the present invention provides a molecule which binds FGFR3 and blocks constitutive and ligand-dependent activation of the receptor, comprising $V_L$-CDR3 and $V_H$-CDR3 regions having SEQ ID NO:13 and SEQ ID NO:12 or SEQ ID NO:9 and SEQ ID NO:8, respectively and the corresponding isolated nucleic acid molecules comprising polynucleotide sequence SEQ ID NO:35 and SEQ ID NO:34 or SEQ ID NO:31 and SEQ ID NO:30.

Another currently preferred embodiment of the present invention provides a molecule herein denoted MSPRO12 comprising a variable light chain ($V_L$) having SEQ ID NO:87 and a variable heavy chain ($V_H$) having amino acid SEQ ID NO:98 and the corresponding isolated nucleic acid molecules comprising polynucleotide sequences having SEQ ID NO:68 and SEQ ID NO:82, respectively.

Another currently preferred embodiment of the present invention provides a molecule herein denoted MSPRO2 comprising a variable light chain ($V_L$) having SEQ ID NO:85 and a variable heavy chain ($V_H$) having SEQ ID NO:96 and the corresponding isolated nucleic acid molecules comprising polynucleotide sequences having SEQ ID NO:67 and SEQ ID NO:77.

A currently most preferred embodiment of the present invention provides a molecule, herein denoted MSPRO59, comprising a variable light chain ($V_L$) having SEQ ID NO:95 and a variable heavy chain ($V_H$) having SEQ ID NO:106 having the corresponding isolated nucleic acid molecules comprising polynucleotide sequences having SEQ ID NO:69 and SEQ ID NO:84, respectively.

According to the principles of the present invention, molecules which bind FGFR and block ligand-dependent receptor activation are provided. These molecules are useful in treating disorders and diseases associated with an FGFR that is activated in a ligand-dependent manner including certain skeletal disorders, hyperproliferative diseases or disorders and non-neoplastic angiogenic pathologic conditions such as neovascular glaucoma, macular degeneration, hemangiomas, angiofibromas, psoriasis and proliferative retinopathy including proliferative diabetic retinopathy.

In one embodiment the present invention provides a molecule which binds FGFR3 and blocks ligand-dependent activation of the receptor, comprising $V_H$-CDR3 and $V_L$-CDR3 regions having SEQ ID NO:20 and SEQ ID NO:21, respectively and the corresponding polynucleotide sequence having SEQ ID NO:44 and SEQ ID NO:45, respectively. In another embodiment the present invention provides a molecule comprising a variable light chain ($V_L$) having SEQ ID NO:92 and a variable heavy chain ($V_H$) having SEQ ID NO:103, having the corresponding isolated nucleic acid molecules comprising polynucleotide sequences having SEQ ID NO:58 and SEQ ID NO:80, respectively.

Other embodiments of the present invention provide a molecule which binds FGFR3 and blocks ligand-dependent activation of the receptor, comprising $V_H$-CDR3 and $V_L$-CDR3 regions selected from SEQ ID NO:10 and SEQ ID NO:11; SEQ ID NO:14 and SEQ ID NO:15; SEQ ID NO:16 and SEQ ID NO:17; SEQ ID NO:18 and SEQ ID NO:19; SEQ ID NO:26 and SEQ ID NO:27 and SEQ ID NO:28 and SEQ ID NO:29 and the corresponding isolated nucleic acid molecules comprising polynucleotide sequences having SEQ ID NO according to Table 1B.

Additional embodiments of the present invention provide molecules having an antigen binding domain comprising a $V_L$ region and a $V_H$ region, respectively, selected from SEQ ID NO:86 and SEQ ID NO:97; SEQ ID NO:88 and SEQ ID NO:99; SEQ ID NO:89 and SEQ ID NO:100; SEQ ID NO:90 and SEQ ID NO:101; SEQ ID NO:91 and SEQ ID NO:102; SEQ ID NO:92 and SEQ ID NO:103; and SEQ ID NO:94 and SEQ ID NO:105 and the corresponding isolated nucleic acid molecules comprising polynucleotide sequences having SEQ ID NO:63 and SEQ ID NO:78; SEQ ID NO:60 and SEQ ID NO:71; SEQ ID NO:57 and SEQ ID NO:72; SEQ ID NO:64 and SEQ ID NO: 79 SEQ ID NO:55 and SEQ ID NO:73; SEQ ID NO:58 and SEQ ID NO:80; and SEQ ID NO:62 and SEQ ID NO:76.

One embodiment of the present invention provides a molecule comprising $V_H$-CDR3 and $V_L$-CDR3 domains of amino acid sequences having SEQ ID NO:22 and SEQ ID NO:23, which has specific affinity for FGFR1 and which blocks ligand-dependent activation of FGFR1, and the corresponding polynucleotide sequences having SEQ ID NO:46 and SEQ ID NO:47.

Another embodiment of the present invention provides a molecule comprising $V_H$ and $V_L$ domains of amino acid sequences having SEQ ID NO:104 and 93, which has specific affinity for FGFR1 and which blocks ligand-dependent activation of FGFR1, and the corresponding isolated nucleic acid molecules comprising polynucleotide sequences having SEQ ID NO:75 and SEQ ID NO:66.

The present invention also relates to methods for screening for the molecules according to the present invention by using a dimeric form of a receptor protein tyrosine kinase as a target for screening a library of antibody fragments.

According to one currently preferred embodiment the screening method comprises
    providing a library of of antigen binding fragments;

screening said library for binding to a dimeric form of a receptor protein tyrosine kinase;

identifying an antigen binding fragment which binds to the dimeric form of the receptor protein tyrosine kinase as a candidate molecule for blocking constitutive activation of the receptor protein tyrosine kinase; and determining whether the candidate molecule blocks constitutive and or ligand-dependent activation of the receptor protein tyrosine kinase in a cell.

According to another embodiment, the dimeric form of the RPTK is a soluble extracellular domain of a receptor protein tyrosine kinase. Non-limiting examples of receptor protein tyrosine kinases disclosed in Blume-Jensen et al. (2001) include EGFR/ErbB1, ErbB2/HER2/Neu, ErbB/HER3, ErbB4/HER4, IGF-1R, PDGFR-a, PDGFR-β, CSF-1R, kit/SCFR, Flk2/FH3, Flk1/VEGFR1, Flk1/VEGFR2, Flt4/VEGFR3, FGFR1, FGFR2/K-SAM, FGFR3, FGFR4, TrkA, TrkC, HGFR, RON, EphA2, EphB2, EphB4, Axl, TIE/TIE1, Tek/TIE2, Ret, ROS, Alk, Ryk, DDR, LTK and MUSK. Heterodimeric form of the receptors my be used as antigen.

By using a dimeric form of the RPTK as bait in the screen, a molecule which would bind to the dimeric form of the receptor has been identified. This presents a novel concept in screening for antibodies or fragments thereof with the capacity to bind to a constitutively activated RPTK such as those associated with various disorders and diseases. It also presents an opportunity to screen for molecules which bind to a heterodimer RPTK. A further aspect of the present invention provides a pharmaceutical composition comprising as an active ingredient a therapeutically effective amount of a molecule of the present invention in a pharmaceutically acceptable carrier or excipient useful for preventing or treating skeletal or cartilage diseases or disorders and craniosynostosis disorders associated with constitutive or ligand-dependent activation of a receptor protein tyrosine kinase.

In one embodiment the pharmaceutical compositions of the present invention may be used for treating or preventing skeletal disorders associated with aberrant FGFR signaling, including achondroplasia, thanatophoric dysplasia, Apert or Pfeiffer syndrome and related craniosynostosis disorders.

A further aspect of the present invention provides a pharmaceutical composition comprising as an active ingredient a therapeutically effective amount of a molecule of the present invention in a pharmaceutically acceptable carrier or excipient useful for preventing or treating cell proliferative diseases or disorders or tumor progression, associated with the constitutive or ligand-dependent activation of a receptor protein tyrosine kinase.

In one embodiment the pharmaceutical compositions of the present invention may be used for treating or preventing proliferative diseases associated with aberrant FGFR signaling, including multiple myeloma, transitional cell carcinoma of the bladder, mammary and cervical carcinoma, chronic myeloid leukemia and osteo- or chondrosarcoma.

A further aspect of the invention provides molecules comprising an antigen binding domain which can be conjugated to a cytotoxin useful for targeting cells expressing said antigen. Another aspect of the present invention provides molecules comprising an antigen binding domain which can be conjugated to appropriate detectable imaging moiety, useful for in vivo tumor imaging.

A still further aspect of the present invention provides methods for treating or inhibiting the aforementioned diseases and disorders by administering a therapeutically effective amount of a pharmaceutical composition comprising a molecule of the present invention to a subject in need thereof.

Other aspects of the invention will be apparent upon consideration of the following description, figures and embodiments.

BRIEF DESCRIPTION OF THE DRAWINGS

FIG. 5 shows the effect of MS-PRO Fabs on proliferation of FGFR-expressing cells.

FIG. 6 shows the effect of MSPRO Fabs on proliferation of FGFR3-expressing cells.

FIG. 7A) or the FDCP-FR1 cells (FIG. 7B).

FIG. 8 shows the receptor specificity of MSPRO Fabs on RCJ cells expressing R3, ach, R1 or R3 receptors by Western blot using an anti-P-JNK (phosphorylated/activated Jun kinase) antibody. FIG. 8A shows different MSPRO Fabs while

FIG. 9 demonstrates the specificity and potency of MS-PRO Fabs by Western blot with anti-P-ERK (phosphorylated/activated ERK) antibody.

FIGS. 13A and 13B show the results of a proliferation assay for FDCP-FR3IIIb or FDCP-FR3IIIc cells incubated with increasing doses of the indicated Fabs.

FIG. 15 shows results of a proliferation assay is a graph wherein iodinated MSPRO29 retained its activity against FGFR3.

FIG. 16 shows the selective binding of radiolabeled MSPRO29 to histological sections of growth plate. FIG. 16A shows Hematoxylin-eosin staining of growth plate treated with radiolabeled MSPRO29 at ×100 magnification. FIG. 16B shows radiomicroscopic sections of growth plate treated with radiolabeled MSPRO29 at ×100 magnification. FIG. 16C shows radiomicroscopic sections of growth plate treated with radiolabeled MSPRO29 at ×400 magnification. FIG. 16D shows Hematoxylin-eosin staining of growth plate treated with radiolabeled Ly6.3 at ×100 magnification. FIG. 16E shows radiomicroscopic sections of growth plate treated with radiolabeled Ly6.3 at ×100 magnification. FIG. 16F shows radiomicroscopic sections of growth plate treated with radiolabeled Ly6.3 at ×400 magnification.

FIG. 30 depicts the polynucleotide sequences of the $V_L$ and $V_H$ of MSPRO antibodies of the present invention SEQ ID NOS: 54-84.

DETAILED DESCRIPTION OF THE INVENTION

Figure 1:
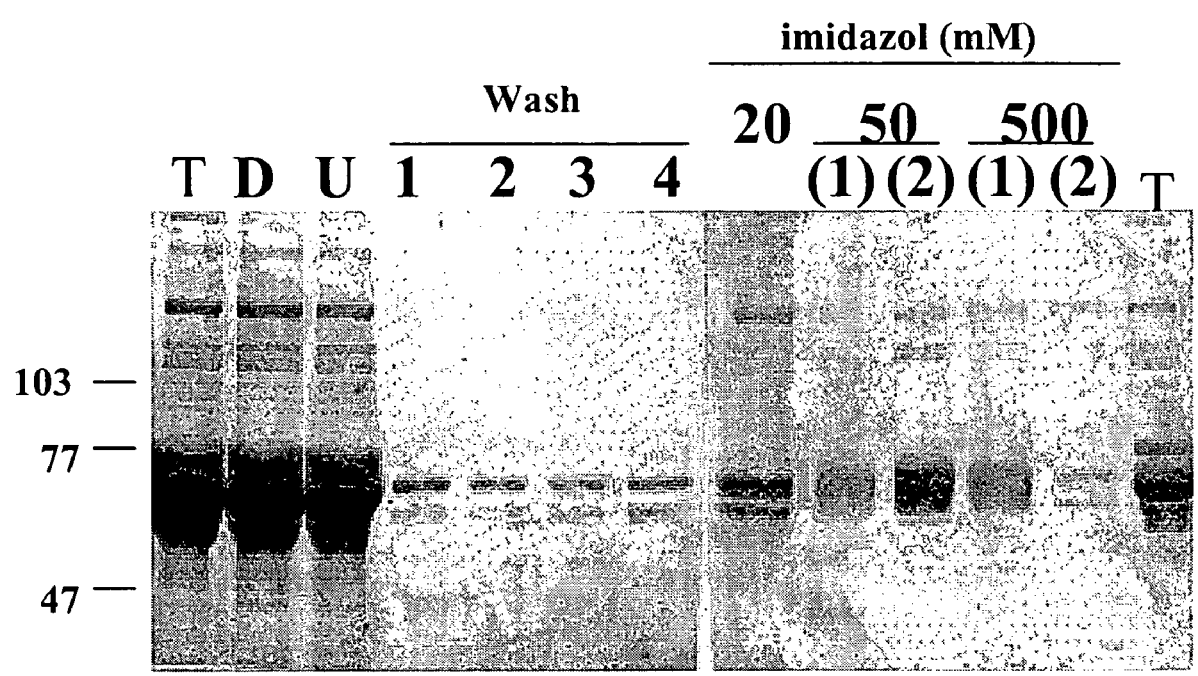
FIG. 1 shows hFR3$^{23-374}$TDhis purification by Coommassie stained SDS-PAGE.

The present invention is based on the discovery that neutralizing antibodies that block ligand-dependent and ligand-independent activation of fibroblast growth factor receptor 3 (FGFR3), a receptor protein tyrosine kinase (RPTK), can be obtained by screening an antibody library against a dimeric form of the extracellular portion of FGFR3. Until the present invention, the present inventors are unaware of any success in obtaining neutralizing antibodies that block constitutive activation of any RPTK including FGFR or ligand-dependent FGFR activation.

For convenience certain terms employed in the specification, examples and claims are described herein.

The term "receptor protein tyrosine kinase" or "RPTK" as used herein and in the claims refers to a subclass of transmembrane-spanning receptors endowed with intrinsic, ligand-stimulatable tyrosine kinase activity. RPTKs comprise a large family of spatially and temporally regulated proteins that control many different aspects of growth and development. When mutated or altered structurally, RPTKs can undergo deregulation and become activated in a ligand-independent, or constitutive, manner. In certain cases they become potent oncoproteins, causing cellular transformation.

As used herein and in the claims the term "fibroblast growth factor receptor" or "FGFR" denotes a receptor specific for FGF which is necessary for transducing the signal exerted by FGF to the cell interior, typically comprising an extracellular ligand-binding domain, a single transmembrane helix, and a cytoplasmic domain having tyrosine kinase activity. The FGFR extracellular domain consists of three immunoglobulin-like (Ig-like) domains (D1, D2 and D3), a heparin binding domain and an acidic box. Alternative splicing of the FGF receptor mRNAs generates different variants of the receptors. Certain abbreviations are employed herein including "FR3" for FGFR3 and "FR1" for FGFR1.

Molecules, including antibodies and fragments thereof, comprising an antigen binding domain to a receptor protein tyrosine kinase are highly necessary for the treatment of various pathological conditions.

In the past, the laboratory of the present inventors encountered difficulties in raising neutralizing antibodies against FGFR3. When mice were immunized with the soluble monomeric FGFR3 receptor, by the time the antibody titers began to increase, the mice died. The experiments performed in the laboratory of the present inventors that failed to obtain anti-FGFR3 neutralizing antibodies in mice are presented in the Examples.

By using a soluble dimeric form of the extracellular domain of the FGFR3 receptor to screen for antibodies, e.g., Fabs, that bind from a phage display antibody library, the present inventors were able to overcome a problem in the prior art for which there was yet no solution and to obtain numerous high affinity ($K_D$<10 nM) antibodies (Fabs) that bind FGFR3 and interfere with ligand binding, thereby blocking ligand-dependent activation of FGFR3 signaling. Very surprisingly, from among the group of Fabs that block ligand-dependent activation, Fab antibodies which also block ligand-independent (constitutive) activation of FGFR3 by blocking signaling caused by constitutive dimerization of FGFR3 were identified. To the best of the present inventors' knowledge, these Fab antibodies, which block constitutive activation of FGFR3, are the first antibodies against any receptor protein tyrosine kinase that block constitutive, ligand-independent activation/signaling.

Trastuzamab, an anti-human epidermal growth factor receptor 2 (HER2) antibody, was the first humanized monoclonal antibody approved for therapeutic use. Its mode of action appears to be manifold, including HER2 down regulation, prevention of heterodimer formation, prevention of HER2 cleavage and others (Baselga and Albanell, 2001). U.S. Pat. Nos. 5,677,171; 5,772,997; 6,165,464; and 6,399,063 disclose the anti-HER2 invention but neither teach nor suggest that the antibody blocks ligand-independent receptor activation.

Embodiments of the Invention

One aspect of the present invention is directed to neutralizing antibodies and more generally to a molecule that comprises the antigen-binding portion of an antibody which blocks ligand-dependent activation and constitutive, ligand-independent activation of a receptor protein tyrosine kinase. According to one embodiment the RPTK is a fibroblast growth factor receptor. According to another embodiment the RPTK is FGFR3.

Another aspect of the present invention is directed to molecules comprising an antigen binding domain which blocks ligand-dependent activation of an FGFR. In one aspect the FGFR is FGFR3.

The molecule having the antigen-binding portion of an antibody according to the present invention can be used in a method for blocking the ligand-dependent activation and/or ligand independent (constitutive) activation of FGFR3. Preferred embodiments of such antibodies/molecules, obtained from an antibody library designated as HUCAL® (Human Combinatorial Antibody Library) clone, is presented in Table 1A with the unique $V_H$-CDR3 and $V_L$-CDR3 sequences given.

In addition to sequencing of the clones, a series of biochemical assays were performed to determine affinity and specificity of the molecules to the respective receptors.

TABLE 1A

| HuCAL® Clone | VH-CDR3 Sequence | VL-CDR3 Sequence | Framework |
|---|---|---|---|
| MSPRO2 | DFLGYEFDY (SEQ ID NO: 8) | QSYDYSADY (SEQ ID NO: 9) | VH1B_L3 |
| MSPRO11 | YYGSSLYHYV FGGFIDY (SEQ ID NO: 10) | QSHHFYE (SEQ ID NO: 11) | VH1B_L2 |
| MSPRO12 | YHSWYEMGYY GSTVGYMFDY (SEQ ID NO: 12) | QSYDFDFA (SEQ ID NO: 13) | VH2_L3 |
| MSPRO21 | DNWFKPFSDV (SEQ ID NO: 14) | QQYDSIPY (SEQ ID NO: 15) | VH1A_k4 |
| MSPRO24 | VNHWTYTFDY (SEQ ID NO: 16) | QQMSNYPD (SEQ ID NO: 17) | VH1A_k3 |
| MSPRO26 | GYWYAYFTYI NYGYFDN (SEQ ID NO: 18) | QSYDNNSDV (SEQ ID NO: 19) | VH1B_L2 |
| MSPRO28 | GGGWVSHGYY YLFDL (SEQ ID NO: 26) | FQYGSIPP (SEQ ID NO: 27) | VH1A_k1 |
| MSPRO29 | TWQYSYFYYL DGGYYFDI (SEQ ID NO: 20) | QQTNNAPV (SEQ ID NO: 21) | VH1B_k3 |
| MSPRO54 | NMAYTNYQYV NMPHFDY (SEQ ID NO: 22) | QSYDYFKL (SEQ ID NO: 23) | VH1B_L3 |
| MSPRO55 | SMNSTMYWYL RRVLFDH (SEQ ID NO: 28) | QSYDMYMYI (SEQ ID NO: 29) | VH1B_L2 |
| MSPRO59 | SYYPDFDY (SEQ ID NO: 24) | QSYDGPDLW (SEQ ID NO: 25) | VH6_L3 |

VH refers to the variable heavy chain,
VL refers to the variable light chain;
L refers to the lambda light chain and
k refers to the kappa light chain.

Table 1B lists the corresponding polynucleotide sequences of the CDR domains.

TABLE 1B

| HuCAL® Clone | VH-CDR3 polynucleotide sequence | VL-CDR3 polynucleotide sequence |
|---|---|---|
| MSPRO2 | GATTTTCTTG GTTATGAGTT TGATTAT (SEQ ID NO: 30) | CAGAGCTATG ACTATTCTGC TGATTAT (SEQ ID NO: 31) |
| MSPRO11 | TATTATGGTT CTTCTCTTTA TCATTATGTT TTTGGTGGTT TTATTGATTA T (SEQ ID NO: 32) | CAGTCTCATC ATTTTTATGA G (SEQ ID NO: 33) |
| MSPRO12 | TATCATTCTT GGTATGAGAT GGGTTATTAT GGTTCTACTG TTGGTTATAT GTTTGATTAT (SEQ ID NO: 34) | CAGAGCTATG ACTTTGATTT TGCT (SEQ ID NO: 35) |
| MSPRO21 | GATAATTGGT TTAAGCCTTT TTCTGATGTT (SEQ ID NO: 36) | CAGCAGTATG TCTATTCCT TAT (SEQ ID NO: 37) |
| MSPRO24 | GTTAATCATT GGACTTATAC TTTTGATTAT (SEQ ID NO: 38) | CAGCAGATGT CTAATTATCC TGAT (SEQ ID NO: 39) |
| MSPRO26 | GGTTATTGGT ATGCTTATTT TACTTATATT AATTATGGTT ATTTTGATAA T (SEQ ID NO: 40) | CAGAGCTATG ACAATAATTC TGATGTT (SEQ ID NO: 41) |
| MSPRO28 | GGTGGTGGTT GGGTTTCTCA TGGTTATTAT TATCTTTTTG ATCTT (SEQ ID NO: 42) | TTTCAGTATG GTTCTATTCC TCCT (SEQ ID NO: 43) |
| MSPRO29 | ACTTGGCAGT ATTCTTATTT TTATTATCTT GATGGTGGTT ATTATTTTGA TATT (SEQ ID NO: 44) | CAGCAGACTA ATAATGCTCC TGTT (SEQ ID NO: 45) |
| MSPRO54 | AATATGGCTT ATACTAATTA TCAGTATGTT AATATGCCTC ATTTTGATTA T (SEQ ID NO: 46) | CAGAGCTATG ACTATTTTAA GCTT (SEQ ID NO: 47) |
| MSPRO55 | TCTATGAATT CTACTATGTA TTGGTAT CTTCGTCGTG TTCTTTTTGA TCAT (SEQ ID NO: 48) | CAGAGCTATG ACATGTATAATTAT ATT (SEQ ID NO: 49) |
| MSPRO59 | TCTTATTATC CTGATTTTGA TTAT (SEQ ID NO: 50) | CAGAGCTATG ACGGTCCTGATCTT TGG (SEQ ID NO: 51) |

Figure 30:
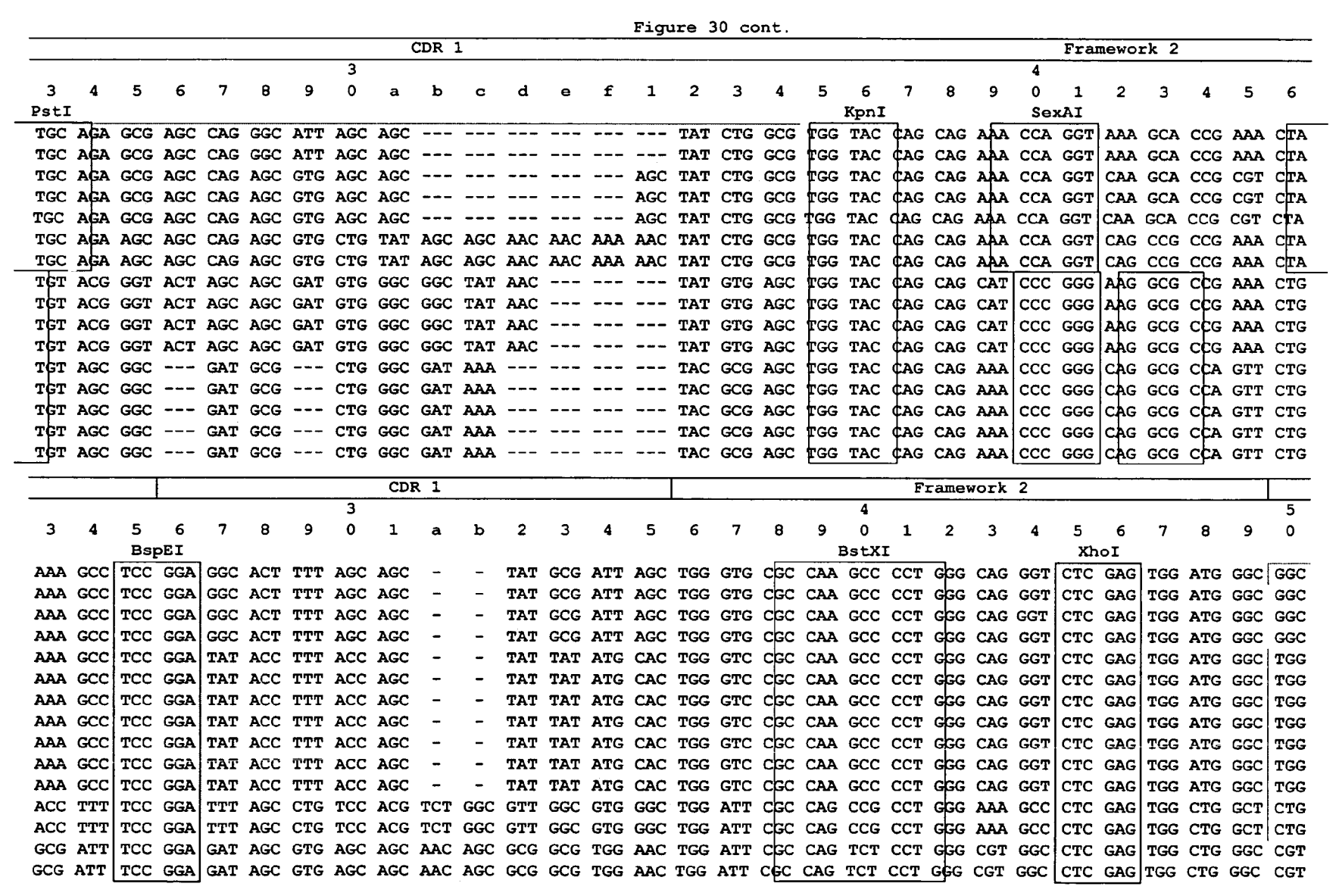
Figure 30:
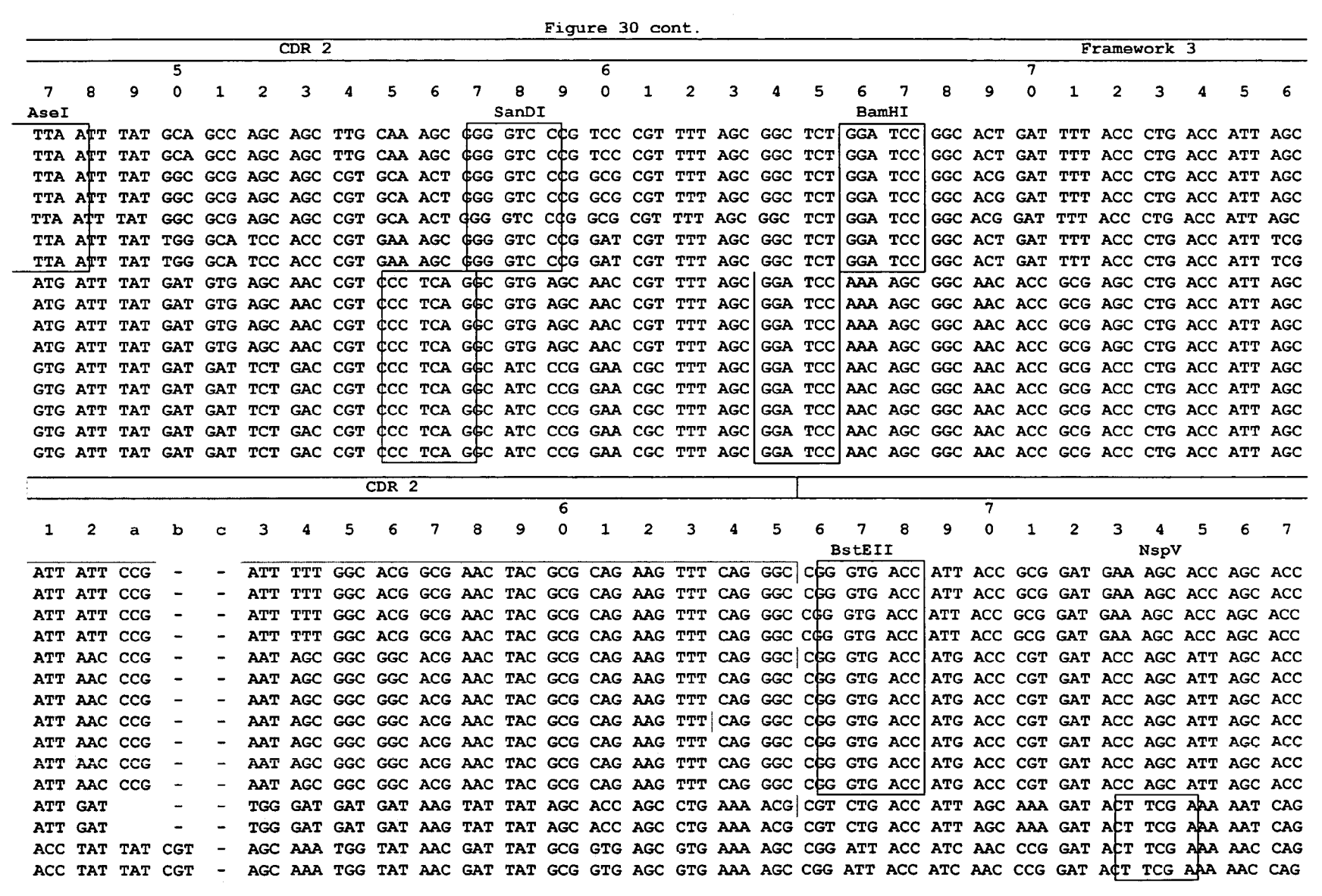
Figure 30:
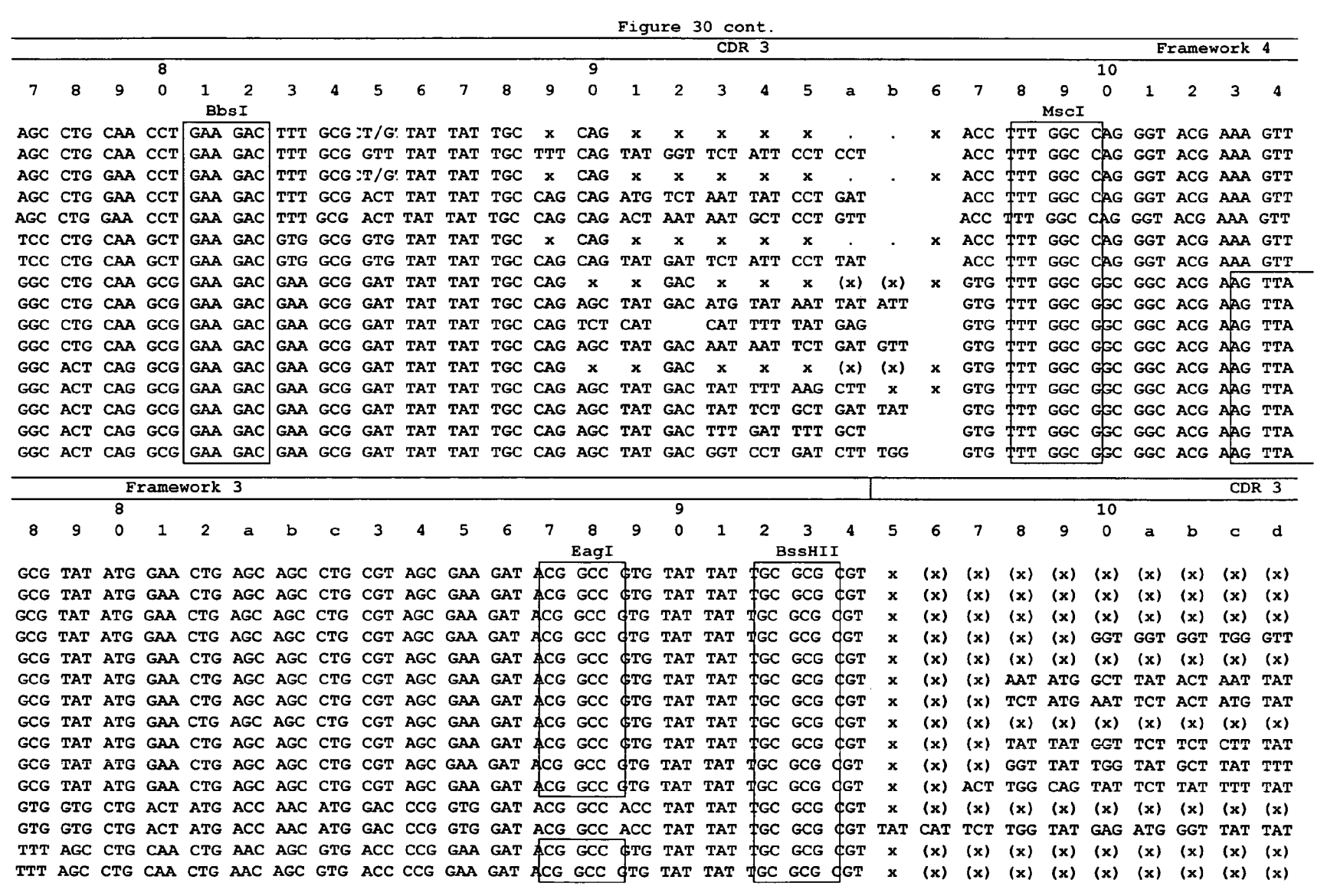
Figure 30:
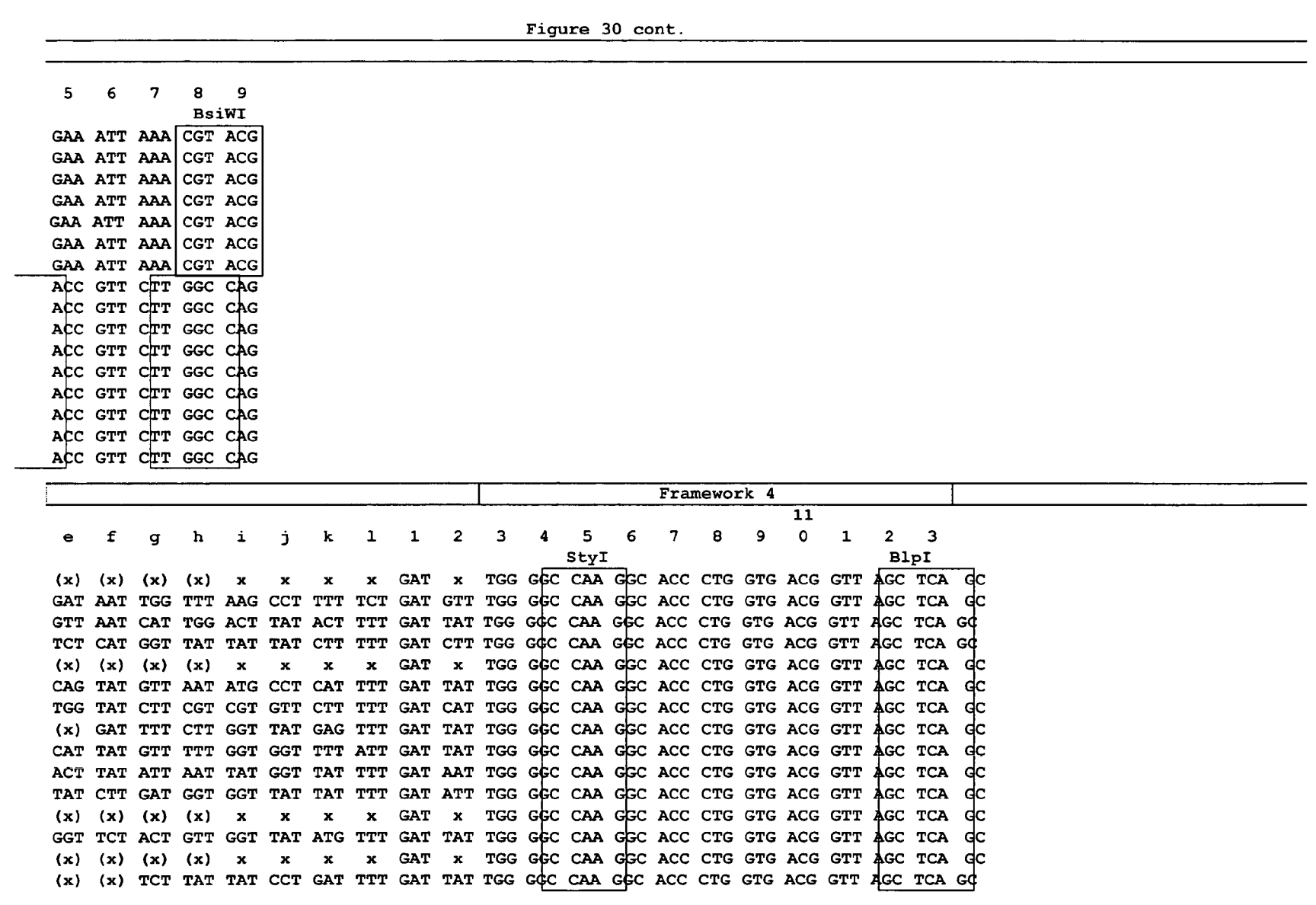

The polypeptide sequence of the VH and VL domains of the currently preferred embodiments of the present invention are presented below. FIG. 30 provides the polynucleotide sequences of the preferred embodiments of the invention.

MS-Pro-2-VL (SEQ ID NO: 85)

```
  1 DIELTQPPSV SVAPGQTARI SCSGDALGDK YASWYQQKPG
    QAPVLVIYDD

51 SDRPSGIPER FSGSNSGNTA TLTISGTQAE DEADYYCQSY
    DYSADYVFGG

101 GTKLTVLGQ
``` corresponding to polynucleotide sequence having SEQ ID NO:67

| MS-Pro-11-VL (SEQ ID NO: 86) |
| --- |
| 1 DIALTQPASV SGSPGQSITI SCTGTSSDVG GYNYVSWYQQ HPGKAPKLMI |
| 51 YDVSNRPSGV SNRFSGSKSG NTASLTISGL QAEDEADYYC QSHHFYEVFG |
| 101 GGTKLTVLGQ | corresponding to polynucleotide sequence having SEQ ID NO:63

| MS-PRO-12-VL (SEQ ID NO: 87) |
| --- |
| 1 DIELTQPPSV SVAPGQTARI SCSGDALGDK YASWYQQKPG QAPVLVIYDD |
| 51 SDRPSGIPER FSGSNSGNTA TLTISGTQAE DEADYYCQSY DFDFAVFGGG |
| 101 TKLTVLGQ | corresponding to polynucleotide sequence having SEQ ID NO:68

| MS-Pro-21-VL (SEQ ID NO: 88) |
| --- |
| 1 DIVMTQSPDS LAVSLGERAT INCRSSQSVL YSSNNKNYLA WYQQKPGQPP |
| 51 KLLIYWASTR ESGVPDRFSG SGSGTDFTLT ISSLQAEDVA VYYCQQYDSI |
| 101 PYTFGQGTKV EIKRT | corresponding to polynucleotide sequence having SEQ ID NO:60

| MS-Pro-24-VL (SEQ ID NO: 89) |
| --- |
| 1 DIVLTQSPAT LSLSPGERAT LSCRASQSVS SSYLAWYQQK PGQAPRLLIY |
| 51 GASSRATGVP ARFSGSGSGT DFTLTISSLE PEDFATYYCQ QMSNYPDTFG |
| 101 QGTKVEIKRT | corresponding to polynucleotide sequence having SEQ ID NO:57

| MS-Pro-26-VL (SEQ ID NO: 90) |
| --- |
| 1 DIALTQPASV SGSPGQSITI SCTGTSSDVG GYNYVSWYQQ HPGKAPKLMI |
| 51 YDVSNRPSGV SNRFSGSKSG NTASLTISGL QAEDEADYYC QSYDNNSDVV |
| 101 FGGGTKLTVL GQ | corresponding to polynucleotide sequence having SEQ ID NO:64

| MS-Pro-28-VL (SEQ ID NO: 91) |
| --- |
| 1 DIQMTQSPSS LSASVGDRVT ITCRASQGIS SYLAWYQQKP GKAPKLLIYA |
| 51 ASSLQSGVPS RFSGSGSGTD FTLTISSLQP EDFAVYYCFQ YGSIPPTFGQ |
| 101 GTKVEIKRT | corresponding to polynucleotide sequence having SEQ ID NO:55

| MS-Pro-29-VL (SEQ ID NO: 92) |
| --- |
| 1 DIVLTQSPAT LSLSPGERAT LSCRASQSVS SSYLAWYQQK PGQAPRLLIY |
| 51 GASSRATGVP ARFSGSGSGT DFTLTISSLE PEDFATYYCQ QTNNAPVTFG |
| 101 QGTKVEIKRT | corresponding to polynucleotide sequence having SEQ ID NO:58

| MS-Pro-54-VL (SEQ ID NO: 93) |
| --- |
| 1 DIELTQPPSV SVAPGQTARI SCSGDALGDK YASWYQQKPG QAPVLVIYDD |
| 51 SDRPSGIPER FSGSNSGNTA TLTISGTQAE DEADYYCQSY DYFKLVFGGG |
| 101 TKLTVLGQ | corresponding to polynucleotide sequence having SEQ ID NO:66

| MS-Pro-55-VL (SEQ ID NO: 94) |
| --- |
| 1 DIALTQPASV SGSPGQSITI SCTGTSSDVG GYNYVSWYQQ HPGKAPKLMI |
| 51 YDVSNRPSGV SNRFSGSKSG NTASLTISGL QAEDEADYYC QSYDMYNYIV |
| 101 FGGGTKLTVL GQ | corresponding to polynucleotide sequence having SEQ ID NO:62

| MS-Pro-59-VL (SEQ ID NO: 95) |
| --- |
| 1 DIELTQPPSV SVAPGQTARI SCSGDALGDK YASWYQQKPG QAPVLVIYDD |
| 51 SDRPSGIPER FSGSNSGNTA TLTISGTQAE DEADYYCQSY DGPDLWVFGG |
| 101 GTKLTVLGQ | corresponding to polynucleotide sequence having SEQ ID NO:69

| MS-Pro-2-VH (SEQ ID NO: 96) |
| --- |
| 1 QVQLVQSGAE VKKPGASVKV SCKASGYTFT SYYMHWVRQA PGQGLEWMGW |
| 51 INPNSGGTNY AQKFQGRVTM TRDTSISTAY MELSSLRSED TAVYYCARDF |
| 101 LGYEFDYWGQ GTLVTVSS | corresponding to polynucleotide sequence having SEQ ID NO:77

| MS-Pro-11-VH (SEQ ID NO: 97) |
| --- |
| 1 QVQLVQSGAE VKKPGASVKV SCKASGYTFT SYYMHWVRQA PGQGLEWMGW |
| 51 INPNSGGTNY AQKFQGRVTM TRDTSISTAY MELSSLRSED TAVYYCARYY |
| 101 GSSLYHYVFG GFIDYWGQGT LVTVSS | corresponding to polynucleotide sequence having SEQ ID NO:78

| MS-Pro-12-VH (SEQ ID NO: 98) |
| --- |
| 1 QVQLKESGPA LVKPTQTLTL TCTFSGFSLS TSGVGVGWIR QPPGKALEWL |
| 51 ALIDWDDDKY YSTSLKTRLT ISKDTSKNQV VLTMTNMDPV DTATYYCARY |
| 101 HSWYEMGYYG STVGYMFDYW GQGTLVTVSS | corresponding to polynucleotide sequence having SEQ ID NO:82

| MS-Pro-21-VH (SEQ ID NO: 99) |
| --- |
| 1 QVQLVQSGAE VKKPGSSVKV SCKASGGTFS SYAISWVRQA PGQGLEWMGG |
| 51 IIPIFGTANY AQKFQGRVTI TADESTSTAY MELSSLRSED TAVYYCARDN |
| 101 WFKPFSDVWG QGTLVTVSS | corresponding to polynucleotide sequence having SEQ ID NO:71

| MS-Pro-24-VH (SEQ ID NO: 100) |
| --- |
| 1 QVQLVQSGAE VKKPGSSVKV SCKASGGTFS SYAISWVRQA PGQGLEWMGG |
| 51 IIPIFGTANY AQKFQGRVTI TADESTSTAY MELSSLRSED TAVYYCARVN |
| 101 HWTYTFDYWG QGTLVTVSS | corresponding to polynucleotide sequence having SEQ ID NO:72

| MS-Pro-26-VH (SEQ ID NO: 101) |
| --- |
| 1 QVQLVQSGAE VKKPGASVKV SCKASGYTFT SYYMHWVRQA PGQGLEWMGW |
| 51 INPNSGGTNY AQKFQGRVTM TRDTSISTAY MELSSLRSED TAVYYCARGY |
| 101 WYAYFTYINY GYFDNWGQGT LVTVSS | corresponding to polynucleotide sequence having SEQ ID NO:79

| MS-Pro-28-VH (SEQ ID NO: 102) |
| --- |
| 1 QVQLVQSGAE VKKPGSSVKV SCKASGGTFS SYAISWVRQA PGQGLEWMGG |
| 51 IIPIFGTANY AQKFQGRVTI TADESTSTAY MELSSLRSED TAVYYCARGG |
| 101 GWVSHGYYYL FDLWGQGTLV TVSS | corresponding to polynucleotide sequence having SEQ ID NO:73

| MS-Pro-29-VH (SEQ ID NO: 103) |
| --- |
| 1 QVQLVQSGAE VKKPGASVKV SCKASGYTFT SYYMHWVRQA PGQGLEWMGW |
| 51 INPNSGGTNY AQKFQGRVTM TRDTSISTAY MELSSLRSED TAVYYCARTW |
| 101 QYSYFYYLDG GYYFDIWGQG TLVTVSS | corresponding to polynucleotide sequence having SEQ ID NO:80

| MS-Pro-54-VH (SEQ ID NO: 104) |
| --- |
| 1 QVQLVQSGAE VKKPGASVKV SCKASGYTFT SYYMHWVRQA PGQGLEWMGW |
| 51 INPNSGGTNY AQKFQGRVTM TRDTSISTAY MELSSLRSED TAVYYCARNM |
| 101 AYTNYQYVNM PHFDYWGQGT LVTVSS | corresponding to polynucleotide sequence having SEQ ID NO:75

| MS-Pro-55-VH (SEQ ID NO: 105) |
| --- |
| 1 QVQLVQSGAE VKKPGASVKV SCKASGYTFT SYYMHWVRQA PGQGLEWMGW |
| 51 INPNSGGTNY AQKFQGRVTM TRDTSISTAY MELSSLRSED TAVYYCARSM |
| 101 NSTMYWYLRR VLFDHWGQGT LVTVSS | corresponding to polynucleotide sequence having SEQ ID NO:76

```
    MS-Pro-59-VH (SEQ ID NO: 106)

1 QVQLQQSGPG LVKPSQTLSL TCAISGDSVS SNSAAWNWIR
    QSPGRGLEWL

51 GRTYYRSKWY NDYAVSVKSR ITINPDTSKN QFSLQLNSVT
    PEDTAVYYCA

101 RSYYPDFDYW GQGTLVTVSS
``` corresponding to polynucleotide sequence having SEQ ID NO:84

In addition to sequencing of the clones, a series of biochemical assays were performed to determine affinity and specificity of the molecules to the respective receptors. Table 1C lists the affinity of the respective molecules to FGFR3 and FGFR1 as measured by BIACORE®-and/or FACS. In a binding assay to FGFR3-expressing cells, the $IC_{50}$ of the molecules was calculated (Example 6). Domain specificity was determined as described in Example 8. The ligand-independent inhibition of FGFR3 (neutralizing activity) was determined as described in Example 10. Finally, the molecules were synthesized in a number of different formats including Fab, miniantibody (Fab-dHLX), IgG1, IgG4, IgG3 and as single chain Fv (scFv).

TABLE 1D-continued

| binder | $IC_{50}$ |
|---|---|
| MSPRO21 | 20 nM (50) |
| MSPRO26 | 8 nM (70) |

TABLE 1E $K_D$ determination for certain molecules

| Clone | BIAcore $K_D$ [nM] | Number of measurements |
|---|---|---|
| MS-Pro-2-dHLX-MH | 4.3 (37) | 1 |
| MS-Pro-11-dHLX-MH | 0.7 (4) | 1 |
| MS-Pro-12-dHLX-MH | 1.2 (14) | 1 |
| MS-Pro-21-dHLX-MH | 2.2 (4.1) | 1 |
| MS-Pro-24-dHLX-MH | 2 (10) | 1 |
| MS-Pro-26-dHLX-MH | 2 (4) | 1 |
| MS-Pro-28-dHLX-MH | 1.6 (9) | 1 |

Certain non-limiting embodiments of molecules according to the present invention that block constitutive (ligand-independent) activation of FGFR3 are referred to herein MSPRO2, MSPRO12 and MSPRO59 comprising $V_H$-CDR3 and $V_L$-CDR3 domains having SEQ ID NO:8 and SEQ ID NO:9; SEQ ID NO:12 and SEQ ID NO:13; and SEQ ID

TABLE 1C

| Clone | Affinity to FGFR3 BIAcore nM | Affinity to FGFR3 (FACS) nM | Affinity to FGFR1 nM | Koff (s$^{-1}$) | $IC_{50}$ FR3 (FGF9 nM) | Domain Specificity | Ligand independent inhibition of FGFR3 | Available formats |
|---|---|---|---|---|---|---|---|---|
| MSPRO59 | 1.5 | <1 | — | 7.1 × 10e-4 | 19 | 2 | + | Fab, Fab-dHLX IgG1, IgG4, mIgG3, scFv |
| MSPRO2 | 37 | 43 | — | 2 × 10e-2 | 360 | 2 | ~ | Fab, Fab-dHLX, IgG1, IgG4, |
| MSPRO12 | 14 | 6.5 | — | 2.3 × 10e-3 | 58 | 2 | + | Fab, Fab-dHLX, IgG1, IgG4, scFv |
| MSPRO11 | 4 | 4 | 108 | 4 × 10e-4 | 220 | 3 | | Fab, Fab-dHLX |
| MSPRO21 | 9 | 1.1 | — | 3.6 × 10e-3 | 50 | 3c | | Fab, Fab-dHLX |
| MSPRO24 | 10 | | — | 5.4 × 10e-3 | 70 | 3c | | Fab, IgG1 |
| MSPRO26 | 4 | 1.4 | 32 | 5 × 10e-4 | 70 | 3 | | Fab, Fab-dHLX |
| MSPRO28 | 9 | 0.3 | 160 | 4 × 10e-3 | 50 | 3 | | Fab |
| MSPRO29 | 6 | <1 | 29 | 1.4 × 10e-3 | 20 | 3c | − | Fab, IgG1, IgG4, Fab-dHLX, scFv |
| MSPRO54 | 3.7 | NA | 2.5 | 2 × 10e-3 | 45 | 3c | | Fab, IgG |
| MSPRO55 | 2.9 | NA | — | 7.4 × 10e-4 | 34 | 3c | | Fab |

Key: affinity (as measured in nM) of the respective molecules to FGFR3 and FGFR1 was measured by BIAcore ® and/or FACS. $IC_{50}$ were determined for the dimeric dHLX format of certain molecules having an antigen binding site in an FDCP-FGFR3 proliferation assay performed with FGF9. Fab-dHLX refers to a Fab mini-antibody format where a dimer of the Fab monomer is produced as a fusion protein after insertion into an expression vector.

BIACORE® results for certain molecules

The numbers in Table 1D represent the $IC_{50}$s of the dimeric dHLX format of certain binders (molecule with antigen binding site) in the FDCP-FGFR3 proliferation assay performed with FGF9. The numbers in parentheses are the $IC_{50}$ of the monomeric Fabs in the same assay. Table 1E presents the $K_D$ value for certain MSPRO molecules in miniantibody form, as determined in the BIACORE® assay.

TABLE 1D

| binder | $IC_{50}$ |
|---|---|
| MSPRO2 | 61 nM (360) |
| MSPRO12 | 26 nM (58) |

NO:24 and SEQ ID NO:25, respectively. The preferred, but non-limiting, embodiments of molecules according to the present invention that block ligand-dependent activation of FGFR3 are referred to herein MSPRO11, MSPRO21, MSPRO24, MSPRO26, MSPRO29, and MSPRO54 comprising VH-CDR3 and VL-CDR3 domains having SEQ ID NO:10 and SEQ ID NO:11; SEQ ID NO:14 and SEQ ID NO:15; SEQ ID NO:16 and SEQ ID NO:17, SEQ ID NO:18 and SEQ ID NO:19; SEQ ID NO:21 and SEQ ID NO:22; SEQ ID NO:23 and SEQ ID NO:24, respectively. An antibody or a molecule of the present invention is said to have increased affinity for a RPTK if it binds a soluble dimeric form of said RPTK with a $K_D$ of less than about 50 nM, preferably less than about 30 nM and more preferably less than about 10 nM, as determined by the BIACORE® chip assay for affinity, by a FACS-Scatchard analysis or other methods known in the art.

For convenience, Tables 1F and 1G outline the pairs of molecules according to their peptide SEQ ID NO and nucleotide SEQ ID NO, respectively.

TABLE 1F

Peptide pairs

Fragment

| antibody # | V heavy chain CDR3 | V light chain CDR3 | V heavy chain | V light chain |
|---|---|---|---|---|
| MSPRO2 | SEQ ID NO: 8 | SEQ ID NO: 9 | SEQ ID NO: 96 | SEQ ID NO: 85 |
| MSPRO12 | SEQ ID NO: 12 | SEQ ID NO: 13 | SEQ ID NO: 98 | SEQ ID NO: 87 |
| MSPRO59 | SEQ ID NO: 24 | SEQ ID NO: 25 | SEQ ID NO: 106 | SEQ ID NO: 95 |
| MSPRO11 | SEQ ID NO: 10 | SEQ ID NO: 11 | SEQ ID NO: 97 | SEQ ID NO: 86 |
| MSPRO21 | SEQ ID NO: 14 | SEQ ID NO: 15 | SEQ ID NO: 99 | SEQ ID NO: 88 |
| MSPRO24 | SEQ ID NO: 16 | SEQ ID NO: 17 | SEQ ID NO: 100 | SEQ ID NO: 89 |
| MSPRO26 | SEQ ID NO: 18 | SEQ ID NO: 19 | SEQ ID NO: 101 | SEQ ID NO: 90 |
| MSPRO28 | SEQ ID NO: 26 | SEQ ID NO: 27 | SEQ ID NO: 102 | SEQ ID NO: 91 |
| MSPRO29 | SEQ ID NO: 20 | SEQ ID NO: 21 | SEQ ID NO: 103 | SEQ ID NO: 92 |
| MSPRO54 | SEQ ID NO: 22 | SEQ ID NO: 23 | SEQ ID NO: 104 | SEQ ID NO: 93 |
| MSPRO55 | SEQ ID NO: 28 | SEQ ID NO: 29 | SEQ ID NO: 105 | SEQ ID NO: 94 |

TABLE 1G

Nucleotide pairs fragment

| antibody # | V heavy chain CDR3 | V light chain CDR3 | V heavy chain | V light chain |
|---|---|---|---|---|
| MSPRO2 | SEQ ID NO: 30 | SEQ ID NO: 31 | SEQ ID NO: 77 | SEQ ID NO: 67 |
| MSPRO12 | SEQ ID NO: 34 | SEQ ID NO: 35 | SEQ ID NO: 82 | SEQ ID NO: 68 |
| MSPRO59 | SEQ ID NO: 50 | SEQ ID NO: 51 | SEQ ID NO: 84 | SEQ ID NO: 69 |
| MSPRO11 | SEQ ID NO: 32 | SEQ ID NO: 33 | SEQ ID NO: 78 | SEQ ID NO: 63 |
| MSPRO21 | SEQ ID NO: 36 | SEQ ID NO: 37 | SEQ ID NO: 71 | SEQ ID NO: 60 |
| MSPRO24 | SEQ ID NO: 38 | SEQ ID NO: 39 | SEQ ID NO: 72 | SEQ ID NO: 57 |
| MSPRO26 | SEQ ID NO: 40 | SEQ ID NO: 41 | SEQ ID NO: 79 | SEQ ID NO: 64 |
| MSPRO28 | SEQ ID NO: 42 | SEQ ID NO: 43 | SEQ ID NO: 73 | SEQ ID NO: 55 |
| MSPRO29 | SEQ ID NO: 44 | SEQ ID NO: 45 | SEQ ID NO: 80 | SEQ ID NO: 58 |
| MSPRO54 | SEQ ID NO: 46 | SEQ ID NO: 47 | SEQ ID NO: 75 | SEQ ID NO: 66 |
| MSPRO55 | SEQ ID NO: 48 | SEQ ID NO: 49 | SEQ ID NO: 76 | SEQ ID NO: 62 |

While the specific discovery of an antibody/molecule that blocks constitutive activation was made with respect to FGFR3 using a soluble dimeric form of FGFR3 to screen a phage display antibody library, it is believed that for all, or almost all, receptor protein tyrosine kinases, antibodies/molecules that block constitutive activation can be similarly obtained using a soluble dimeric form of a corresponding extracellular domain of a receptor protein tyrosine kinase. Non-limiting examples of receptor protein tyrosine kinases disclosed in Blume-Jensen et al. (2001) include EGFR/ErbB1, ErbB2/HER2/Neu, ErbB/HER3, ErbB4/HER4, IGF-1R, PDGFR-a, PDGFR-β, CSF-1R, kit/SCFR, Flk2/FH3, Flk1/VEGFR1, Flk1/VEGFR2, Flt4/VEGFR3, FGFR1, FGFR2/K-SAM, FGFR3, FGFR4, TrkA, TrkC, HGFR, RON, EphA2, EphB2, EphB4, Axl, TIE/TIE1, Tek/TIE2, Ret, ROSAlk, Ryk, DDR, LTK and MUSK.

Furthermore, antibodies/molecules that block ligand-dependent or ligand-independent activation of heterodimer receptor protein tyrosine kinases are intended to be included in the scope of the invention. Heterodimerization is well documented for members of the EGFR subfamily of receptor protein tyrosine kinases and others. Non-limiting examples include EGFR/PDGFRβ, Flt1/KDR and EGFR/ErbB2 heterodimers. EGFR and PDGFRβ heterodimers have been identified as a mechanism for PDGF signal transduction in rat vascular smooth muscle cells (Saito et al., 2001) and Flt-1/KDR heterodimers are required for vinculin assembly in focal adhesions in response to VEGF signaling (Sato et al., 2000).

The present invention is also directed to a molecule having the antigen-binding portion of an antibody which binds to a dimeric form of an extracellular portion of a receptor protein tyrosine kinase (RPTK), such as a FGFR, and blocks the ligand-independent (constitutive) activation and/or ligand-dependent activation of the RPTK.

Further provided is a method for screening a molecule comprising the antigen-binding portion of an antibody which blocks ligand-independent or ligand-dependent activation of a receptor protein tyrosine kinase, comprising:
  providing a library of antigen binding fragments;
  screening a library of antigen binding fragments for binding to a dimeric form of a receptor protein tyrosine kinase;
  identifying an antigen binding fragment which binds to the dimeric form of the receptor protein tyrosine kinase as a candidate molecule for blocking constitutive activation of the receptor protein tyrosine kinase; and
  determining whether the candidate molecule blocks constitutive and or ligand-dependent activation of the receptor protein tyrosine kinase in a cell.

Antibodies

Antibodies, or immunoglobulins, comprise two heavy chains linked together by disulfide bonds and two light chains, each light chain being linked to a respective heavy chain by disulfide bonds in a "Y" shaped configuration. Proteolytic digestion of an antibody yields Fv (fragment variable comprising Fab domains) and Fc (fragment crystalline) domains. The antigen binding domains, Fab', include regions where the polypeptide sequence varies. The term F(ab')$_2$ represents two Fab' arms linked together by disulfide bonds. The central axis of the antibody is termed the Fc fragment. Each heavy chain has at one end a variable domain (V$_H$) followed by a number of constant domains (C$_H$). Each light chain has a variable domain (V$_L$) at one end and a constant domain (C$_L$) at its other end, the light chain variable domain being aligned with the variable domain of the heavy chain and the light chain constant domain being aligned with the first constant domain of the heavy chain (C$_{H1}$). The variable domains of each pair of light and heavy chains form the antigen binding site. The domains on the light and heavy chains have the same general structure and each domain comprises four framework regions, whose sequences are relatively conserved, joined by three hypervariable domains known as complementarity determining regions (CDR1-3). These domains contribute specificity and affinity of the antigen binding site. The isotype of the heavy chain (gamma, alpha, delta, epsilon or mu) determines immunoglobulin class (IgG, IgA, IgD, IgE or IgM, respectively). The light chain is either of two isotypes (kappa, ? or lambda, ?) found in all antibody classes.

It should be understood that when the terms "antibody" or "antibodies" are used, this is intended to include intact antibodies, such as polyclonal antibodies or monoclonal antibodies (mAbs), as well as proteolytic fragments thereof such as the Fab or F(ab')$_2$ fragments. Further included within the scope of the invention are chimeric antibodies; human and humanized antibodies; recombinant and engineered antibodies, and fragments thereof. Furthermore, the DNA encoding the variable region of the antibody can be inserted into the DNA encoding other antibodies to produce chimeric antibodies (see, for example, U.S. Pat. No. 4,816,567). Single chain antibodies fall within the scope of the present invention. Single chain antibodies can be single chain composite polypeptides having antigen binding capabilities and comprising amino acid sequences homologous or analogous to the variable regions of an immunoglobulin light and heavy chain (linked V$_H$-V$_L$ or single chain Fv (scFv)). Both V$_H$ and V$_L$ may copy natural monoclonal antibody sequences or one or both of the chains may comprise a CDR-FR construct of the type described in U.S. Pat. No. 5,091,513, the entire contents of which are incorporated herein by reference. The separate polypeptides analogous to the variable regions of the light and heavy chains are held together by a polypeptide linker. Methods of production of such single chain antibodies, particularly where the DNA encoding the polypeptide structures of the V$_H$ and V$_L$ chains are known, may be accomplished in accordance with the methods described, for example, in U.S. Pat. Nos. 4,946,778, 5,091,513 and 5,096,815, the entire contents of which are hereby incorporated by reference.

Additionally, CDR grafting may be performed to alter certain properties of the antibody molecule including affinity or specificity. A non-limiting example of CDR grafting is disclosed in U.S. Pat. No. 5,225,539.

A "molecule having the antigen-binding portion of an antibody" as used herein is intended to include not only intact immunoglobulin molecules of any isotype and generated by any animal cell line or microorganism, but also the antigen-binding reactive fraction thereof, including, but not limited to, the Fab fragment, the Fab' fragment, the F(ab')$_2$ fragment, the variable portion of the heavy and/or light chains thereof, Fab miniantibodies (see WO 93/15210, U.S. patent application Ser. No. 08/256,790, WO 96/13583, U.S. patent application Ser. No. 08/817,788, WO 96/37621, U.S. patent application Ser. No. 08/999,554, the entire contents of which are incorporated herein by reference) and chimeric or single-chain antibodies incorporating such reactive fraction, as well as any other type of molecule or cell in which such antibody reactive fraction has been physically inserted, such as a chimeric T-cell receptor or a T-cell having such a receptor, or molecules developed to deliver therapeutic moieties by means of a portion of the molecule containing such a reactive fraction. Such molecules may be provided by any known technique, including, but not limited to, enzymatic cleavage, peptide synthesis or recombinant techniques.

The term "Fc" as used herein is meant as that portion of an immunoglobulin molecule (Fragment crystallizable) that mediates phagocytosis, triggers inflammation and targets Ig to particular tissues; the Fc portion is also important in complement activation.

In one embodiment of the invention, a chimera comprising a fusion of the extracellular domain of the RPTK and an immunoglobulin constant domain can be constructed useful for assaying for ligands for the receptor and for screening for antibodies and fragments thereof.

The "extracellular domain" when used herein refers the polypeptide sequence of the RPTKs disclosed herein which are normally positioned to the outside of the cell. The extracellular domain encompasses polypeptide sequences in which part or all of the adjacent (C-terminal) hydrophobic transmembrane and intracellular sequences of the mature RPTK have been deleted. Thus, the extracellular domain-containing polypeptide can comprise the extracellular domain and a part of the transmembrane domain. Alternatively, in the preferred embodiment, the polypeptide comprises only the extracellular domain of the RPTK. The truncated extracellular domain is generally soluble. The skilled practitioner can readily determine the extracellular and transmembrane domains of a RPTK by aligning the RPTK of interest with known RPTK amino acid sequences for which these domains have been delineated. Alternatively, the hydrophobic transmembrane domain can be readily delineated based on a hydrophobicity plot of the polypeptide sequence. The extracellular domain is N-terminal to the transmembrane domain.

The term "epitope" is meant to refer to that portion of any molecule capable of being bound by an antibody or a fragment thereof which can also be recognized by that antibody. Epitopes or antigenic determinants usually consist of chemically active surface groupings of molecules such as amino acids or sugar side chains and have specific three-dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

A "neutralizing antibody" as used herein refers to a molecule having the antigen binding site to a specific receptor capable of reducing or inhibiting (blocking) activity or signaling through a receptor, as determined by in vivo or in vitro assays, as per the specification.

A monoclonal antibody (mAb) is a substantially homogeneous population of antibodies to a specific antigen. MAbs may be obtained by methods known to those skilled in the art. See, for example Kohler et al (1975); U.S. Pat. No. 4,376,110; Ausubel et al (1987-1999); Harlow et al (1988); and Colligan et al (1993), the contents of which references are incorporated entirely herein by reference. The mAbs of the present invention may be of any immunoglobulin class including IgG, IgM, IgE, IgA, and any subclass thereof. A hybridoma producing an mAb may be cultivated in vitro or in vivo. High titers of mAbs can be obtained in in vivo production where cells from the individual hybridomas are injected intraperitoneally into pristine-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules, the different portions of which are derived from different animal species, such as those having a variable region derived from a murine mAb and a human immunoglobulin constant region. Antibodies which have variable region framework residues substantially from human antibody (termed an acceptor antibody) and complementarity determining regions substantially from a mouse antibody (termed a donor antibody) are also referred to as humanized antibodies. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Better et al, 1988; Cabilly et al, 1984; Harlow et al, 1988; Liu et al, 1987; Morrison et al, 1984; Boulianne et al, 1984; Neuberger et al, 1985; Sahagan et al , 1986; Sun et al, 1987; Cabilly et al; European Patent Applications 125023, 171496, 173494, 184187, 173494, PCT patent applications WO 86/01533, WO 97/02671, WO 90/07861, WO 92/22653 and U.S. Pat. Nos. 5,693,762, 5,693, 761, 5,585,089, 5,530,101 and 5,225,539). These references are hereby incorporated by reference.

Besides the conventional method of raising antibodies in vivo, antibodies can be generated in vitro using phage display technology. Such a production of recombinant antibodies is much faster compared to conventional antibody production and they can be generated against an enormous number of antigens. In contrast, in the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant monoclonal antibodies one can use various methods all based on phage display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens. Protocols for bacteriophage library construction and selection of recombinant antibodies are provided in the well-known reference text, Current Protocols in Immunology, Colligan et al (Eds.), John Wiley & Sons, Inc. (1992-2000), Chapter 17, Section 17.1.

Another aspect of the present invention is directed to a method for screening for the antibody or molecule of the present invention by screening a library of antibody fragments displayed on the surface of bacteriophage, such as disclosed in the Examples herein and described in WO 97/08320, U.S. Pat. No. 6,300,064 and Knappik et al. (2000), for binding to a soluble dimeric form of a receptor protein tyrosine kinase. An antibody fragment which binds to the soluble dimeric form of the RPTK used for screening is identified as a candidate molecule for blocking ligand-dependent activation and/or constitutive activation of the RPTK in a cell. Preferably the RPTK of which a soluble dimeric form is used in the screening method is a fibroblast growth factor receptor (FGFR), and most preferably FGFR3.

As a first screening method, the soluble dimeric form of a receptor tyrosine kinase can be constructed and prepared in a number of different ways. For instance, the extracellular domain of a RPTK joined to Fc and expressed as a fusion polypeptide that dimerizes naturally by means of the Fc portion of the RPTK-Fc fusion. Other suitable types of constructs of FGFR3, serving as guidance for other RPTKs, are disclosed in the Examples presented herein.

The assays for determining binding of antibody fragments to FGFR3, binding affinities, inhibition of cell proliferation, etc., are also described in the Examples herein below.

The term "cell proliferation" refers to the rate at which a group of cells divides. The number of cells growing in a vessel can be quantified by a person skilled in the art when that person visually counts the number of cells in a defined volume using a common light microscope. Alternatively, cell proliferation rates can be quantified by laboratory apparati that optically or conductively measure the density of cells in an appropriate medium.

A second screen for antibody fragments as candidate molecules can be done using cells having very high overexpression of the RPTK, such as for instance RCJ-M15 cells overexpressing mutant (achondroplasia) FGFR3. In cells expressing very high levels of receptor some ligand-independent activation occurs even without the presence of a mutation, such as a constitutive activation mutation. It is believed that RPTK overexpression forces RPTKs to dimerize and signal even in the absence of ligand. These cells have monomeric receptors as well as dimeric receptors present on their cell surface. Using this type of cell, one of skill in the art would be able to identify all different kinds of antibodies, i.e., blocking ligand-dependent activation, blocking constitutive activation, blocking activation and binding only to monomeric form, etc.

Other screens can be carried out on cell lines expressing a RPTK carrying a mutation, such as the FDCP-FR3ach line expressing the FGFR3 achondroplasia mutation. The receptors of this line become constitutively active, e.g. are able to signal in the absence of a ligand as determined by ERK (MAPK) phosphorylation, a downstream effector.

A further aspect of the present invention relates to a method for treating or inhibiting a skeletal dysplasia or craniosynostosis disorder associated with constitutive activation of a RPTK which involves administering the molecule of the present invention to a subject need thereof. Non-limiting examples of skeletal dysplasias include achondroplasia, thanatophoric dysplasia (TDI or TDII), hypochondroplasia, and severe achondroplasia with developmental delay and acanthosis nigricans (SADDAN) dysplasia. Non-limiting examples of craniosynostosis disorder are Muenke coronal craniosynostosis and Crouzon syndrome with acanthosis nigricans. The symptoms and etiology of these diseases and disorders are reviewed in Vajo et al. (Vajo et al, 2000).

The present invention also provides for a method for treating or inhibiting a cell proliferative disease or disorder associated with the action of an abnormal constitutively activated RPTK, for example tumor formation, primary tumors, tumor progression or tumor metastasis. A molecule comprising at least one antigen binding portion of an antibody that blocks constitutive activation of a RPTK is administered to a subject in need thereof to treat or inhibit such a cell proliferative disease or disorder.

The terms "treating or inhibiting a proliferative disease or disorder" or "treating or inhibiting a tumor" are used herein and in the claims to encompass tumor formation, primary tumors, tumor progression or tumor metastasis.

Tumor formation or tumor growth are intended to encompass solid and non-solid tumors. Solid tumors include mammary, ovarian, prostate, colon, cervical, gastric, esophageal, papillary thyroid, pancreatic, bladder, colorectal, melanoma, small-cell lung and non-small-cell lung cancers, granulose cell carcinoma, transitional cell carcinoma, vascular tumors, all types of sarcomas, e.g. osteosarcoma, chondrosarcoma, Kaposi's sarcoma, myosarcoma, hemangiosarcoma, and glioblastomas.

Non-solid tumors include for example hematopoietic malignancies such as all types of leukemia, e.g. chronic myelogenous leukemia (CML), acute myelogenous leukemia (AML), mast cell leukemia, chronic lymphocytic leukemia (CLL) and acute lymphocytic leukemia (ALL), lymphomas, and multiple myeloma (MM). FGFR3 has been implicated in poor prognosis seen in some patients.

Tumor progression is the phenomenon whereby cancers become more aggressive with time. Progression can occur in the course of continuous growth, or when a tumor recurs after treatment and includes progression of transitional cell carcinoma, osteo or chondrosarcoma, multiple myeloma, and mammary carcinoma (one of the known RPTKs involved in mammary carcinoma is ErbB3).

The role of the FGFR3 in tumor progression associated with transitional cell carcinoma and multiple myeloma has recently been elucidated (Cappellen, et al, 1999; Chesi, et al, 2001)

In another aspect of the present invention, molecules which bind FGFR, more preferably FGFR3, and block ligand-dependent receptor activation are provided. These molecules are useful in treating hyperproliferative diseases or disorders and non-neoplastic angiogenic pathologic conditions such as neovascular glaucoma, proliferative retinopathy including proliferative diabetic retinopathy, macular degeneration, hemangiomas, angiofibromas, and psoriasis. The role of FGFs and their receptors in neo- and hypervascularization has been well documented (Frank, 1997; Gerwins et al, 2000)

In another aspect of the present invention, the pharmaceutical compositions according to the present invention is similar to those used for passive immunization of humans with other antibodies. Typically, the molecules of the present invention comprising the antigen binding portion of an antibody will be suspended in a sterile saline solution for therapeutic uses. The pharmaceutical compositions may alternatively be formulated to control release of active ingredient (molecule comprising the antigen binding portion of an antibody) or to prolong its presence in a patient's system. Numerous suitable drug delivery systems are known and include, e.g., implantable drug release systems, hydrogels, hydroxymethylcellulose, microcapsules, liposomes, microemulsions, microspheres, and the like. Controlled release preparations can be prepared through the use of polymers to complex or adsorb the molecule according to the present invention. For example, biocompatible polymers include matrices of poly (ethylene-co-vinyl acetate) and matrices of a polyanhydride copolymer of a stearic acid dimer and sebaric acid (Sherwood et al, 1992). The rate of release of the molecule according to the present invention, i.e., of an antibody or antibody fragment, from such a matrix depends upon the molecular weight of the molecule, the amount of the molecule within the matrix, and the size of dispersed particles (Saltzman et al., 1989 and Sherwood et al., 1992). Other solid dosage forms are described in (Ansel et al., 1990 and Gennaro, 1990).

The pharmaceutical composition of this invention may be administered by any suitable means, such as orally, intranasally, subcutaneously, intramuscularly, intravenously, intraarterially, intralesionally or parenterally. Ordinarily, intravenous (i.v.) or parenteral administration will be preferred.

It will be apparent to those of ordinary skill in the art that the therapeutically effective amount of the molecule according to the present invention will depend, inter alia, upon the administration schedule, the unit dose of molecule administered, whether the molecule is administered in combination with other therapeutic agents, the immune status and health of the patient, the therapeutic activity of the molecule administered and the judgment of the treating physician. As used herein, a "therapeutically effective amount" refers to the amount of a molecule required to alleviate one or more symptoms associated with a disorder being treated over a period of time.

Although an appropriate dosage of a molecule of the invention varies depending on the administration route, age, body weight, sex, or conditions of the patient and should be ultimately determined by the physician, in the case of oral administration, the daily dosage can generally be between about 0.01-200 mg, preferably about 0.01-10 mg, more preferably about 0.1-10 mg, per kg body weight. In the case of parenteral administration, the daily dosage can generally be between about 0.001-100 mg, preferably about 0.001-1 mg, more preferably about 0.01-1 mg, per kg body weight. The daily dosage can be administered, for example, in regimens typical of 1-4 individual administrations daily. Various considerations in arriving at an effective amount are described, e.g., in Goodman and Gilman's: The Pharmacological Basis of Therapeutics, 8th ed., Pergamon Press, 1990; and Remington's Pharmaceutical Sciences, 17th ed., Mack Publishing Co., Easton, Pa., 1990.

The molecule of the present invention as an active ingredient is dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well-known to those in the art. (See, for example, Ansel et al., 1990 and Gennaro, 1990). In addition, if desired, the composition can contain minor amounts of auxiliary substances such as wetting or emulsifying agents, or pH buffering agents.

Combination Therapy

The combined treatment of one or more of the molecules of the invention with an anti-neoplastic or anti-chemotherapeutic drug such as doxorubicin, cisplatin or TAXOL® provides a more efficient treatment for inhibiting the growth of tumor cells than the use of the molecule by itself. In one embodiment, the pharmaceutical composition comprises the antibody and carrier with an anti-chemotherapeutic drug.

The present invention also provides for an isolated acid molecule, which comprises a polynucleotide sequence encoding the molecule having at least one antigen binding portion of an antibody that blocks ligand-dependent activation and/or constitutive activation of a receptor protein tyrosine kinase such as FGFR3, and a host cell comprising this nucleic acid molecule. Furthermore, also within the scope of the present invention is a nucleic acid molecule containing a polynucleotide sequence having at least 90% sequence identity, preferably about 95%, and more preferably about 97% identity to the above encoding nucleotide sequence as would well understood by those of skill in the art.

The invention also provides isolated nucleic acid molecule that hybridizes under high stringency conditions to polynucleotides having SEQ ID NO:30 through SEQ ID NO:51 and SEQ ID NOS: 55, 57-58, 60, 62-64, 66-69, 71-73, 75-80, 82, 84 or the complement thereof. As used herein, highly stringent conditions are those which are tolerant of up to about 5-20% sequence divergence, preferably about 5-10%. Without limitation, examples of highly stringent (−10° C. below the calculated Tm of the hybrid) conditions use a wash solution of 0.1.times.SSC (standard saline citrate) and 0.5% SDS at the appropriate Ti below the calculated Tm of the hybrid. The ultimate stringency of the conditions is primarily due to the washing conditions, particularly if the hybridization conditions used are those which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6×SSPE), 5× Denhardt's reagent, 0.5% SDS, 100 µg/ml denatured, fragmented salmon sperm DNA at an appropriate incubation temperature Ti. See generally Sambrook et al. (Molecular Cloning: A Laboratory Manual, 2d edition, Cold Spring Harbor Press (1989)) for suitable high stringency conditions.

Stringency conditions are a function of the temperature used in the hybridization experiment and washes, the molarity of the monovalent cations in the hybridization solution and in the wash solution(s) and the percentage of formamide in the hybridization solution. In general, sensitivity by hybridization with a probe is affected by the amount and specific activity of the probe, the amount of the target nucleic acid, the detectability of the label, the rate of hybridization, and the duration of the hybridization. The hybridization rate is maximized at a Ti (incubation temperature) of 20-25° C. below Tm for DNA:DNA hybrids and 10-15° C. below Tm for DNA:RNA hybrids. It is also maximized by an ionic strength of about 1.5M Na+. The rate is directly proportional to duplex length and inversely proportional to the degree of mismatching.

Specificity in hybridization, however, is a function of the difference in stability between the desired hybrid and "background" hybrids. Hybrid stability is a function of duplex length, base composition, ionic strength, mismatching, and destabilizing agents (if any).

The Tm of a perfect hybrid may be estimated for DNA:DNA hybrids using the equation of Meinkoth et al (1984), as $$Tm=81.5° C.+16.6(\log M)+0.41(\% GC)−0.61(\% form)−500/L$$

and for DNA:RNA hybrids, as $$Tm=79.8° C.+18.5(\log M)+0.58(\% GC)−11.8(\% GC)^2−0.56(\% form)−820/L$$

where

M, molarity of monovalent cations, 0.01-0.4 M NaCl,
% GC, percentage of G and C nucleotides in DNA, 30%-75%,
% form, percentage formamide in hybridization solution, and
L, length hybrid in base pairs.

Tm is reduced by 0.5-1.5° C. (an average of 1° C. can be used for ease of calculation) for each 1% mismatching.

The Tm may also be determined experimentally. As increasing length of the hybrid (L) in the above equations increases the Tm and enhances stability, the full-length rat gene sequence can be used as the probe.

Filter hybridization is typically carried out at 68° C., and at high ionic strength (e.g., 5-6×SSC), which is non-stringent, and followed by one or more washes of increasing stringency, the last one being of the ultimately desired high stringency. The equations for Tm can be used to estimate the appropriate Ti for the final wash, or the Tm of the perfect duplex can be determined experimentally and Ti then adjusted accordingly.

The present invention also relates to a vector comprising the nucleic acid molecule of the present invention. The vector of the present invention may be, for example, a plasmid, cosmid, virus, bacteriophage or another vector used conventionally in genetic engineering, and may comprise further genes such as marker genes which allow for the selection of said vector in a suitable host cell and under suitable conditions.

Furthermore, the vector of the present invention may, in addition to the nucleic acid sequences of the invention, comprise expression control elements, allowing proper expression of the coding regions in suitable hosts. Such control elements are known to the artisan and may include a promoter, a splice cassette, translation initiation codon, translation and insertion site for introducing an insert into the vector.

Preferably, the nucleic acid molecule of the invention is operatively linked to said expression control sequences allowing expression in eukaryotic or prokaryotic cells.

Control elements ensuring expression in eukaryotic or prokaryotic cells are well known to those skilled in the art. As mentioned herein above, they usually comprise regulatory sequences ensuring initiation of transcription and optionally poly-A signals ensuring termination of transcription and stabilization of the transcript.

Methods for construction of nucleic acid molecules according to the present invention, for construction of vectors comprising said nucleic acid molecules, for introduction of said vectors into appropriately chosen host cells, for causing or achieving the expression are well-known in the art (see, e.g., Sambrook et al., 1989; Ausubel et al., 1994).

The invention also provides for conservative amino acid variants of the molecules of the invention. Variants according to the invention also may be made that conserve the overall molecular structure of the encoded proteins. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved.

For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d)

negatively charged (acidic) amino acids include aspartic acid and glutamic acid. Substitutions typically may be made within groups (a)-(d). In addition, glycine and proline may be substituted for one another based on their ability to disrupt a-helices. Similarly, certain amino acids, such as alanine, cysteine, leucine, methionine, glutamic acid, glutamine, histidine and lysine are more commonly found in a-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and 1. Given the known genetic code, and recombinant and synthetic DNA techniques, the skilled scientist readily can construct DNAs encoding the conservative amino acid variants.

As used herein, "sequence identity" between two polypeptide sequences indicates the percentage of amino acids that are identical between the sequences. "Sequence similarity" indicates the percentage of amino acids that either are identical or that represent conservative amino acid substitutions.

Conjugates

One embodiment of the present invention provides molecules of the present invention conjugated to cytotoxins. The cytotoxic moiety of the antibody may be a cytotoxic drug or an enzymatically active toxin or bacterial or plant origin, or an enzymatically active fragment of such a toxin including, but not limited to, diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, curcin, crotin, saponin, gelonin, mitogellin, restrictocin, phenomycin, and enomycin. In another embodiment, the molecules of the present invention are conjugated to small molecule anti-cancer drugs. Conjugates of the antibody and such cytotoxic moieties are made using a variety of bifunctional protein coupling agents. Examples of such reagents include SPDP, IT, bifunctional derivatives of imidoesters such a dimethyl adipimidate HCl, active esters such as disuccinimidyl suberate, aldehydes such as glutaraldehyde, bis-azido compounds such as bis-(p-azidobenzoyl) hexanediamine, bis-diazonium derivatives, dissocyanates and bis-active fluorine compounds. The lysing portion of a toxin may be joined to the Fab fragment of the antibodies.

Additionally, the molecules of the present invention can also be detected in vivo by imaging, for example imaging of cells which have undergone tumor progression or have metastasized. Antibody labels or markers for in vivo imaging of RPTKs include those detectable by X-radiography, NMR, PET, or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody.

A specific antibody or antibody portion which has been labeled with an appropriate detectable imaging moiety, such as a radioisotope (for example, $^{131}$I, $^{111}$In, $^{99}$Tc), a radio-opaque substance, or a material detectable by nuclear magnetic resonance, is introduced (for example, parenterally, subcutaneously or intraperitoneally) into the mammal to be examined for a disorder. It will be understood in the art that the size of the subject and the imaging system used will determine the quantity of imaging moieties needed to produce diagnostic images. In the case of a radioisotope moiety, for a human subject, the quantity of radioactivity injected will normally range from about 5 to 20 millicuries. The labeled antibody or antibody portion will then preferentially accumulate at the location of cells which contain a specific RPTK. In vivo tumor imaging is described in Burchiel et al., (1982).

The methods and compositions described herein may be performed, for example, by utilizing pre-packaged diagnostic test kits comprising in one or more containers (i) at least one immunoglobulin of the invention and (ii) a reagent suitable for detecting the presence of said immunoglobulin when bound to its target. A kit may be conveniently used, e.g., in clinical settings or in home settings, to diagnose patients exhibiting a disease (e.g., skeletal dysplasia, craniosynostosis disorders, cell proliferative diseases or disorders, or tumor progression), and to screen and identify those individuals exhibiting a predisposition to such disorders. A composition of the invention also may be used in conjunction with a reagent suitable for detecting the presence of said immunoglobulin when bound to its target, as well as instructions for use, to carry out one or more methods of the invention.

Having now generally described the invention, the same will be more readily understood through reference to the following examples, which are provided by way of illustration and are not intended to be limiting of the present invention.

EXAMPLES

An important approach to controlling cellular FGFR3 activity is the generation of reagents that block receptor signaling. Without wishing to be bound by theory, molecules which bind the extracellular domain of the receptor may inhibit the receptor by competing with FGF or heparin binding or, alternatively, by preventing receptor dimerization. Additionally, binding to the extracellular domain may accelerate receptor internalization and turnover. Humanized antibodies are expected to have inhibitory/neutralizing action and are of particular interest since they are considered to be valuable for therapeutic applications, especially by avoiding the human anti-mouse antibody response frequently observed with rodent antibodies. The experiments in which the neutralizing antibodies are screened, identified and obtained using fully synthetic human antibody libraries (for discovering highly specific binders against a wide variety of antigens) and FGFR3 extracellular domain are described below.

Example 1

Attempt to Generate Anti-FGFR3 Antibodies

One hundred micrograms of soluble FGFR3 in complete Freund's Adjuvant were injected into Balb/c 3T3 naive mice (9 animals). Two repeated injections of 20 micrograms were performed at week intervals. 10 days after the second booster injection, blood was drawn from animals and serum was tested for the presence of polyclonal antibodies both by monitoring for binding to the receptor as well as for neutralizing activity at a dilution of 1:50. No significant neutralizing activity was observed in the tested serum (20% at most in some animals). A perfusion injection of 20 micrograms of soluble receptor was administered 1-2 days later but all the mice harboring some activity of neutralizing Ab died. The experiment was repeated twice with the same results.

Example 2

Generation of the FGFR3 Antigens

Two dimeric forms of the extracellular domain of the human FGFR3 were prepared for use as antigen. One was a histidine-tagged domain with a Serine 371 to Cysteine (S371C) substitution (thanatophoric dysplasia (TD) mutation) to facilitate dimerization and the second one an Fc fusion. The S371C variant was shown to bind heparin and FGF9 coated plates and to inhibit FGF9-dependent FDCP-FR3 proliferation. The Fc fusion was similarly effective in binding assays, demonstrating its potential as an inhibitor of FGFR function and as a target for selecting FGFR3 inhibitory molecules. Both soluble receptors were employed to select neutralizing human recombinant antibodies.

The two variants of the FGFR3 extracellular domain were prepared as follows:

1. A construct containing the extracellular portion of FGFR3 with a thanatophoric dysplasia (TD) mutation to facilitate dimer formation conjugated to a His-tag (histidine tag) was generated. A bluescript plasmid comprising the human FGFR3 gene (pBS-hFGFR3) was used as template for PCR with the following primers:

```
5'-ACGTGCTAGC TGAGTCCTTG GGGACGGAGC   (SEQ ID NO: 2)
AG.

5'-ACGTCTCGAG TTAATGGTGA TGGTGATGGT   (SEQ ID NO: 3)
GTGCATACAC ACAGCCCGCC TCGTC,
``` wherein the Ser 371 Cys (S371C) substitution is bold and underlined.

The nucleotide sequence encoding the extracellular domain of FGFR3 with the TD substitution is denoted herein SEQ ID NO:7.

The PCR fragment was digested with XhoI and ligated into pBlueScript digested with EcoRV and XhoI. The resulting plasmid, pBsFR3$^{23-374}$TDhis, was cleaved with NheI and XhoI and the DNA fragment encoding the extracellular domain of FGFR3 was ligated into the same restriction sites in pCEP-Pu/Ac7 (Yamaguchi et al., 1999; Kohfeldt et al., 1997), generating the pCEP-hFR3$^{23-374}$TDhis plasmid construct.

To express this FGFR3 variant, 293E cells (EBNA virus transfected 293 cells) were transfected with the aforementioned plasmid, pCLP-hFR3$^{23-374}$TDhis, clones were identified and grown. Cell supernatants analyzed by Western blot with anti-His antibody demonstrated high expression of the soluble receptor. Supernatants from large scale preparations were then subjected to batch affinity purification with Ni-NTA beads and the tagged soluble receptor was eluted by a step gradient ranging from 20 mM to 500 mM imidazol. A sample from each elute was loaded onto a 7.5% SDS-PAGE and stained with GELCODE® (Pierce). In parallel, Western blot analysis was performed and analyzed with anti-His antibodies. SDS-PAGE (FIG. 1) and immunoblot (not shown) analyses demonstrated peak amounts of purified extracellular FGFR3 in the 2nd (2) 50 mM imidazol fraction. About 0.5 mg of pure protein was obtained following this single step purification. In FIG. 1, T=total protein, D=dialysed protein, U=unbound fraction.

Figure 2:
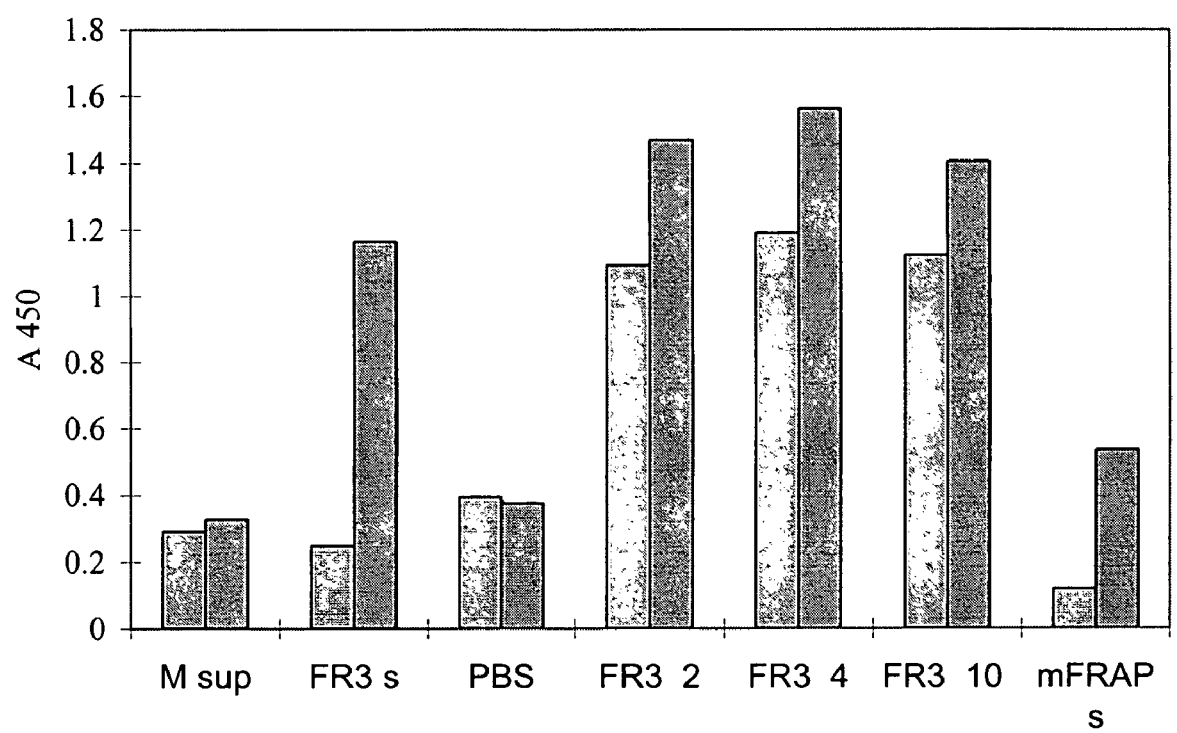
FIG. 2 shows hFR3$^{23-374}$TDhis binding to heparin and FGF9.

To assess whether hFR3$^{23-374}$TDhis (hFR3-TDhis) retained the ability to associate with heparin and heparin-FGF complex, heparin coated wells were incubated with 2, 4 or 10 µg purified (labeled as FR3 2, FR3 4 or FR3 10, respectively in FIG. 2) or unpurified (FR3 s) hFR3$^{23-374}$TDhis with (checkered bar) or without FGF9 (200 ng/well, hatched bar). The binding of hFR3$^{23-374}$TDhis to each well was determined with anti-His antibody. Mock supernatant (M sup), PBS and unpurified mouse FR3AP (FGFR3-alkaline phosphatase, labeled as mFRAP sup) were included as controls. The results, as presented in FIG. 2, demonstrated that, similar to what was reported for the wild-type receptor, hFR3$^{23-374}$TDhis binds to heparin and that this interaction is augmented by the presence of FGF9. Finally, it was demonstrated that hFR3$^{23-374}$TDhis inhibits FDCP-FR3 FGF-dependent proliferation in a dose dependent manner. hFR3$^{23-374}$TDhis had no inhibitory effect on proliferation when FDCP-FR3 cells were grown in the presence of IL-3. Taken together, hFR3$^{23-374}$TDhis proved to be a good candidate as a target antigen for screening for FGFR3 neutralizing antibodies.

2. The extracellular domain of FGFR3 and FGFR1 were prepared as Fc fusions (FR3exFc and FR1exFc). The amino acid sequence of FGFR3 (NCBI access no: NP_000133) is denoted herein SEQ ID NO:1.

To construct the FR3exFc fusion, a polynucleotide sequence (denoted herein SEQ ID NO:4) encoding the extracellular domain of FGFR3 was PCR amplified to contain terminal KpnI and BamHI restriction sites for insertion into the KpnI and BamHI sites of pCXFc (denoted herein SEQ ID NO:5). This insertion positions the extracellular domain of FGFR3 to be expressed as a fusion with the Fc amino acid sequence (denoted herein SEQ ID NO:6).

Figure 3:
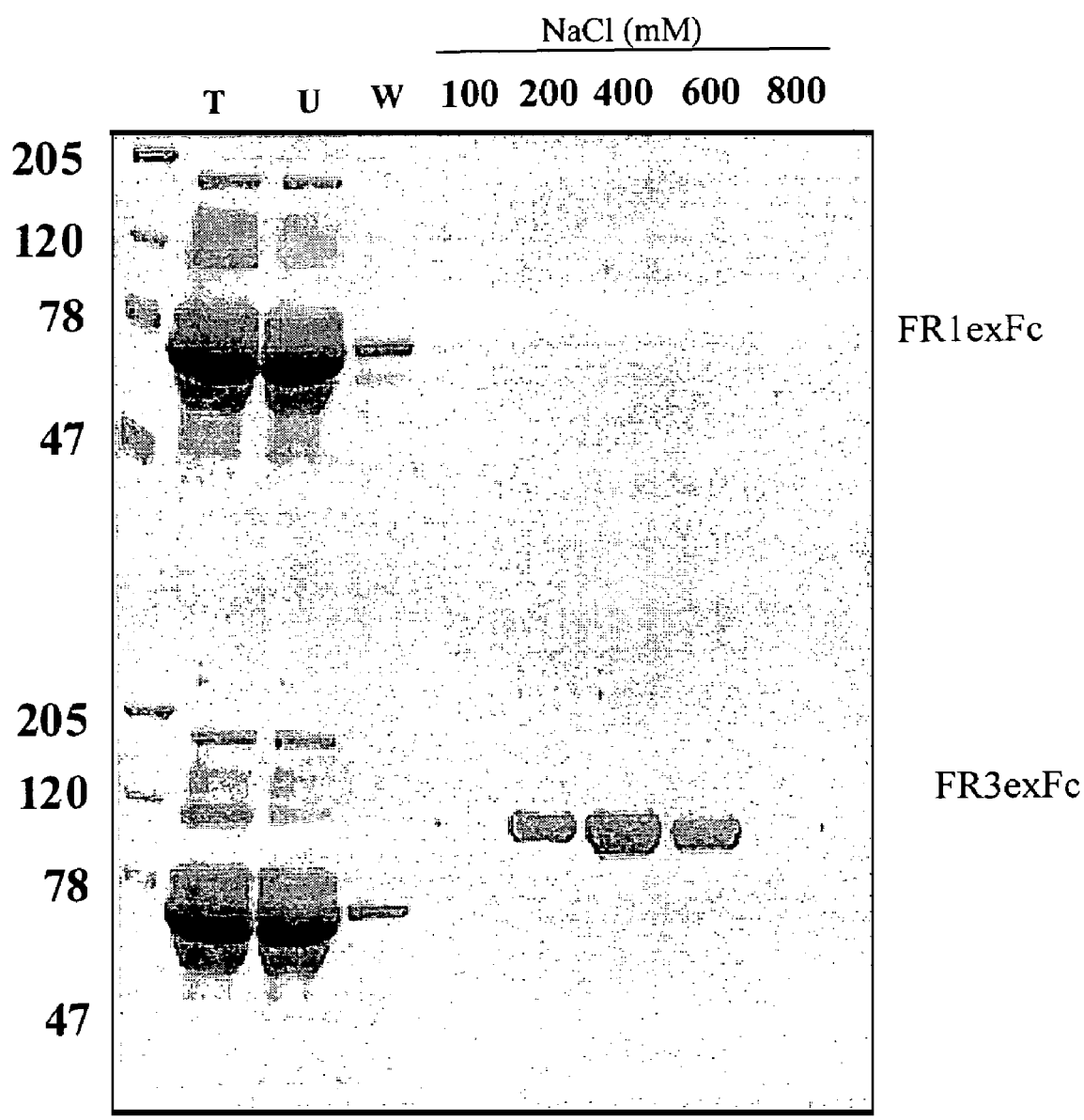
FIG. 3 shows the purification of FR3exFc and FR1exFc on SDS-PAGE.

Both FR3exFc and FR1exFc soluble receptors were demonstrated to be expressed to a high level in transiently transfected 293T cells (T-cell antigen infected human embryonic kidney 293 cells). The observation that both soluble receptors remain bound to heparin-coated wells even following extensive washes led the laboratory of the present inventors to try to purify the proteins with the commercial HEPARIN-SEPHAROSE® resin (Pharmacia). One hundred ml volume supernatants, harvested 48 hours post-transfection with either FR3exFc or FR1exFc coding plasmids, were incubated overnight at 4° C. with 1 ml HEPARIN-SEPHAROSE® resin. The resin was washed and then subjected to PBS supplemented with increasing concentration of NaCl. Aliquots of each fraction were analyzed by 7.5% SDS-PAGE stained with GELCODE® (Pierce) demonstrating a purification profile of more than 90% homogeneity and a peak elution at 400 mM NaCl for FR3exFc (FIG. 3; T=total protein, U=unbound fraction, W=wash). In contrast, FR1exFc was hardly retained on the resin. This result was confirmed by Western analysis of the same fractions with anti-FGFR1ex antibodies demonstrating that most of FR1exFc is in the unbound fraction (not shown).

Functional analysis of FR3exFc and FR1exFc showed that both compete efficiently for FGF9 binding and stimulating FGFR3, thus, demonstrating their potential as inhibitors of FGFRs function and as a target (FR3exFc) for selecting FGFR3 inhibitory molecules.

Neutralizing Effect of Soluble Receptors

Figure 4:
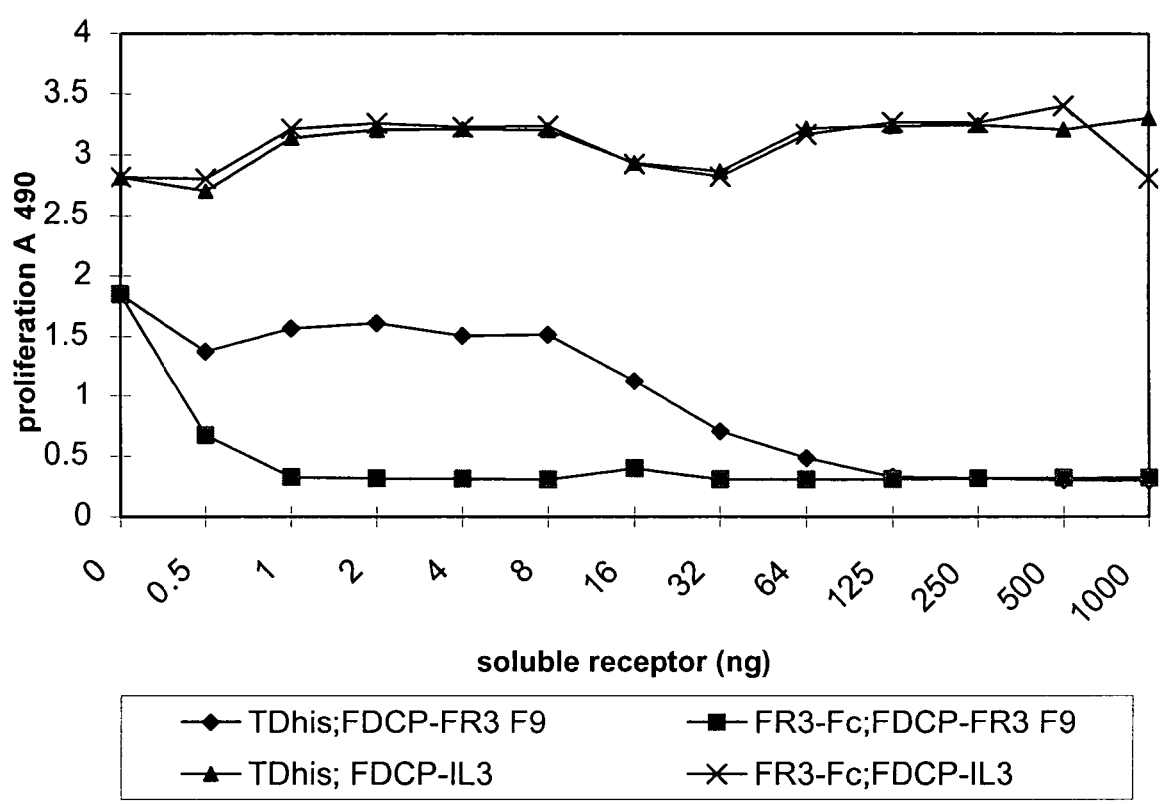
FIG. 4 shows the neutralization effect of the hFR3$^{23-374}$TDhis and FR3exFc soluble receptors in a ligand-dependent proliferation assay.

The ability of hFR3-TDhis and FR3exFc to inhibit FGF-dependent FDCP-R3 cell proliferation was compared. Both soluble receptors inhibited FDCP-R3 cell proliferation, however, FR3exFc was about 60 times more potent than hFR3TDhis. Neither had an effect on FDCP cells stimulated with IL-3. (FIG. 4; legend: ?-FR3$^{23-374}$TDhis on FDCP-FR3 cells+FGF9, |-FR3exFc on FDCP-FR3 cells+FGF9, ?-FR3$^{23-374}$TDhis on FDCP-FR3 cells+IL-3, X-FR3exFc on FDCP-FR3 cells+IL-3). The fact that FR3exFc is entirely in dimeric form whereas only a small proportion (⅒) of hFR3$^{23-374}$TDhis is in dimeric form might explain, at least in part, this difference.

Example 3

Screening for Antibodies

Panning and First Screening of Ab Binding Characterization

The screening strategies to identify Fabs from the Human Combinatorial Antibody Library (HUCAL®, developed at MorphoSys, Munich, Germany and disclosed in WO 97/08320, U.S. Pat. No. 6,300,064, and Knappik et al., (2000), the entire contents of which are incorporated herein by reference, using soluble dimeric forms of the extracellular domain of the FGFR3 receptor are shown in Table 2.

TABLE 2

Panning Strategies

|  | Panning Round 1 | Panning Round 2 | Panning Round 3 |
|---|---|---|---|
| Screen 1 | FR3-TDhis | HEK293 | FR3-TDhis |
| Screen 2 | FR3exFc captured with mouse anti-human IgG | RCJ-FR3ach | FR3exFc captured with mouse anti-human IgG |
| Screen 3 | FR3-TDhis (Round 1 of panning 1) | RCJ-FR3ach & RCJ-FR3wt | FR3exFc Captured with mouse anti-human IgG |

The screening was carried out, for example in Screen 1, by coating the wells of a 96 well plate with hFR3$^{23-374}$TDhis (FR3-TDhis), panning with the bacteriophage library and selecting the positive clones. The positive clones were then tested on HEK293 (293, human embryonic kidney) cells, expressing endogenous FGFR3. The positive clones were selected and rescreened on FR3-TDhis. Two additional similar screenings were carried out as shown in Table 2. In screen 2 the first and third pannings were carried out with the FR3exFc antigen and the second panning carried out with RCJ cells expressing a mutant (achondroplasia) form of FGFR3. An overview of the number of initial hits and of the candidate clones is shown in Table 3.

TABLE 3

Overview of Screenings 1, 2 and 3 on FGFR3

|  | screened clones | primary hits | sequenced clones | consolidated candidate clones (ELISA & FACS) |
|---|---|---|---|---|
| Screen 1 | 1076 | 208 | 69 | 15 (MSPRO 1-15) |
| Screen 2 | 864 | 300 | 32 | 22 (MSPRO 20-33 and 52-59) |
| Screen 3 | 768 | 487 | 52 | 11 (MSPRO 40-50) |

Sequence and Vector Data

Figure 28:
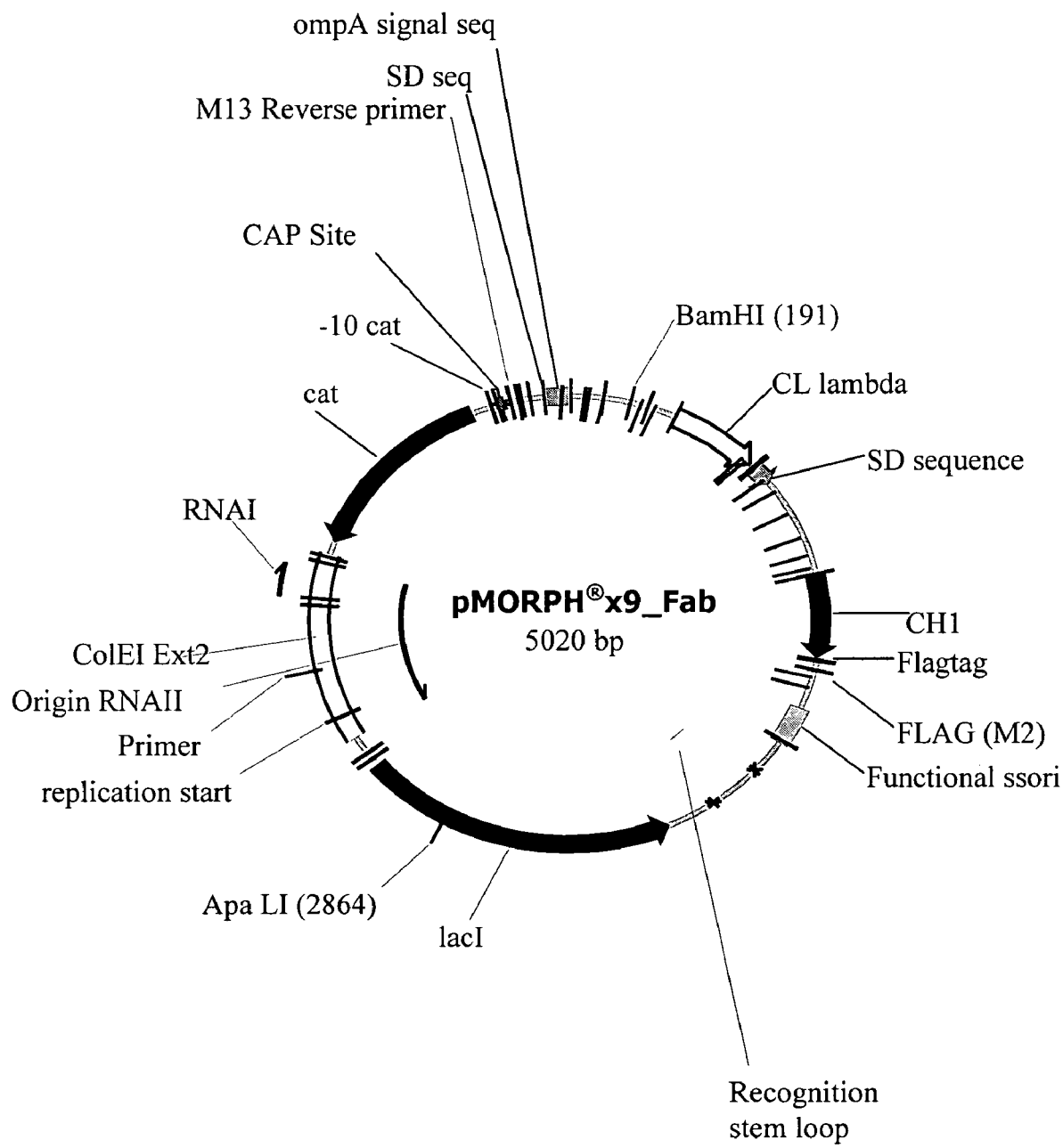
FIG. 28 is an example of a Fab expression vector, having SEQ ID NO:52, for use in accordance with the present invention.
Figure 29:
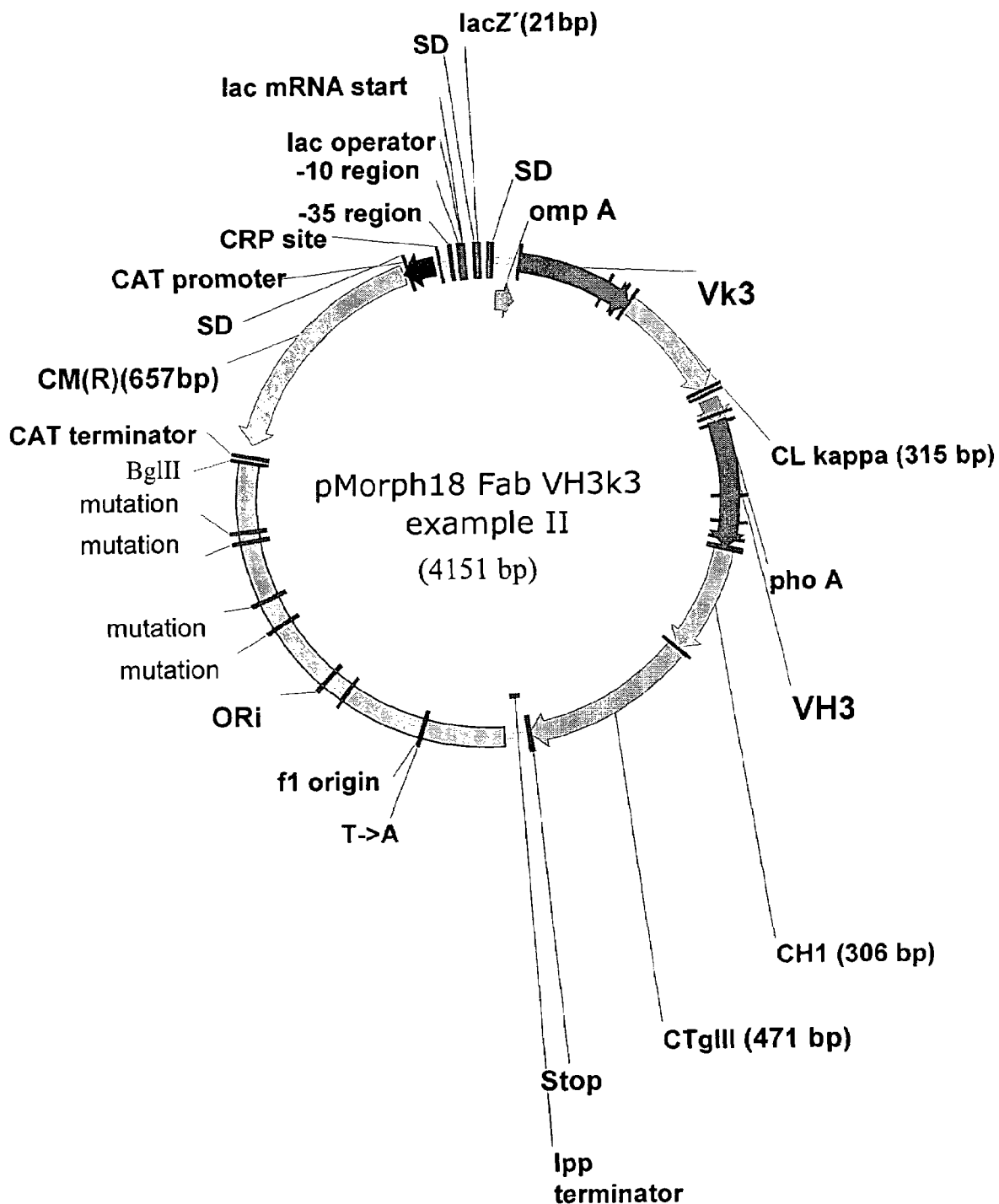
FIG. 29 is an example of a phage display vector, having SEQ ID NO:53, for use in accordance with the present invention.

A plasmid map of the dHLX-MH vector having SEQ ID NO:52 is presented in FIG. 28. FIG. 29 shows the plasmid map of the phage display vector, having SEQ ID NO:53, used in accordance with the present invention.

FIG. 30 displays the polynucleotide sequences of the specific V$_L$ and V$_H$ domains of MSPRO2 (SEQ ID NO:67 and 77); MSPRO11 (SEQ ID NO:63 and 78); MSPRO12 (SEQ ID NO:68 and 82); MSPRO21 (SEQ ID NO:60 and 71); MSPRO24 (SEQ ID NO:57 AND 72); MSPRO26 (SEQ ID NO:64 AND 79); MSPRO28 (SEQ ID NO:55 AND 73); MSPRO29 (SEQ ID NO:58 AND 80); MSPRO54 (SEQ ID NO:66 AND 75); MSPRO55 (SEQ ID NO:62 AND 76); and MSPRO59 (SEQ ID NO:69 AND 84). The sequences include the framework domains 1-4 and the CDR domains 1-3. SEQ ID NO:54, SEQ ID NO:56, SEQ ID NO:59, SEQ ID NO:61, and SEQ ID NO:65 denote herein the polynucleotide sequences of the parent V$_L$ (kappa or lambda) strands. SEQ ID NO:70, SEQ ID NO:74, SEQ ID NO:81 and SEQ ID NO:83 denote herein the polynucleotide sequences of the V$_H$ parent strands.

Example 4

Analysis of Fabs Identified in First Screening

Specificity of Antibody Recognition

The first screening yielded 15 different Fabs that specifically recognize FGFR3 in vitro and on the cell surface. Fourteen of these were further analysed. LY6.3, an anti-lysosyme antibody, was isolated from the same library and serves as a control. ELISA analysis, according to the following protocol was carried out to determine the specificity of the isolated Fabs for FGFR3 or FGFR1.

Fab-FR3/Fc Binding Assay

Figure 27:
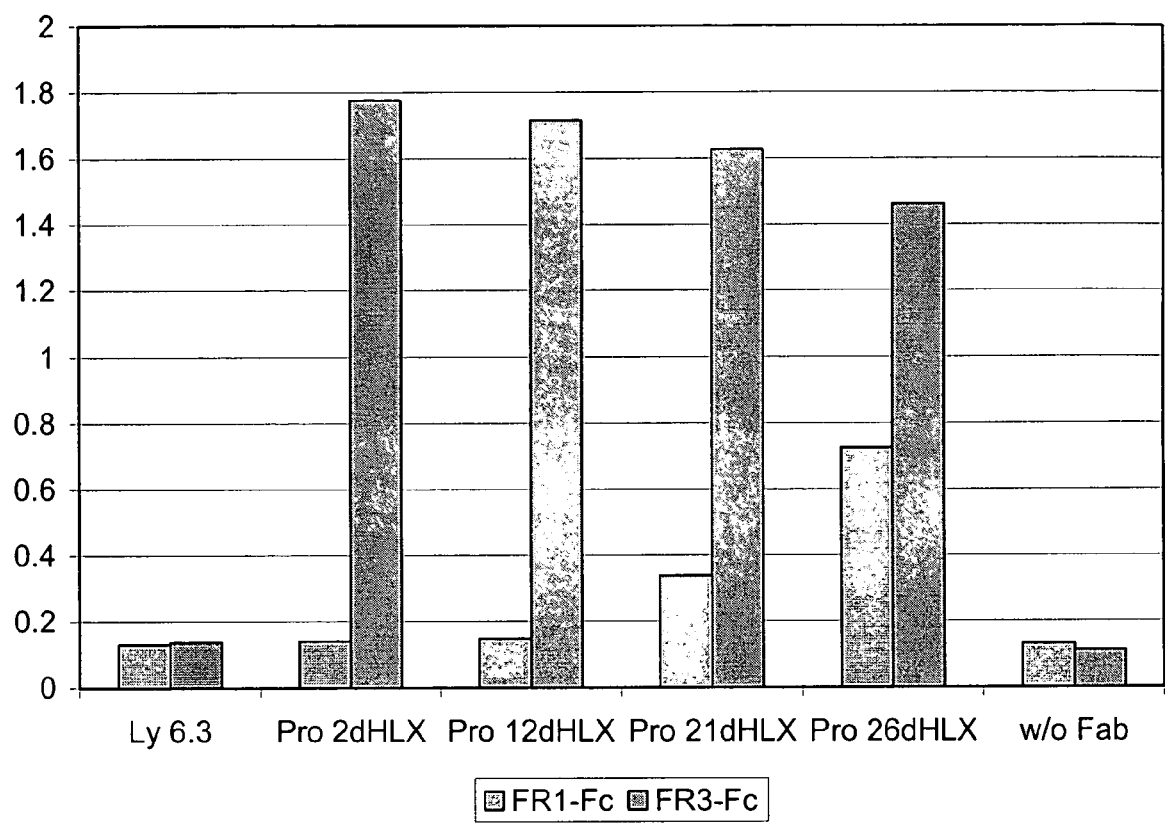
FIG. 27 shows binding of Fab Miniantibodies to FGFR3-Fc and FGFR1-Fc (ELISA).

MAXISORP® ELISA plates were coated with 100 μl anti-human Fc (10 μg/ml) in bicarbonate overnight at 40° C. Wells were washed five consecutive times with a PBS solution containing 0.1% Tween 20 (PBST). The well surface was blocked with 250 μl PBST+3% BSA (blocking solution) for 1 hour at 37° C. This was followed by capturing 1 μg of FGFR/Fc for 1 hour at room temperature. To assess the antibody binding to the captured FGFR/Fc, 1 μg each of the tested Fabs was incubated in 100 μl blocking solution per well 1 hour at room temperature. Wells were washed 5 times with PBST. Reaction was initiated with the addition of 100 μl of 0.8 μg/ml goat anti-human Fab-HRP (horseradish peroxidase) diluted in blocking solution, subsequently washed and detected with TMB substrate (Pierce). The absorbance was measured at 450 nm. A comparison of ELISA analyses done in both laboratories, Prochon and MorphoSys, is presented in FIG. 27 and in Table 4.

TABLE 4

|  | ProChon | | MorphoSys | |
|---|---|---|---|---|
|  | FR1/Fc | FR3/Fc | FR1/Fc | FR3/Fc |
| MS-PRO1 | ++ | ++ | +/− | + |
| MS-PRO2 | − | ++ | − | ++ |
| MS-PRO3 | + | ++ | − | ++ |
| MS-PRO4 | − | + | − | ++ |
| MS-PRO5 | − | ++ | +/− | + |
| MS-PRO6 | − | ++ | − | + |
| MS-PRO7 | − | ++ | − | + |
| MS-PRO8 | + | ++ | − | + |
| MS-PRO9 | − | +/− | +/− | + |
| MS-PRO10 | + | ++ | − | ++ |
| MS-PRO11 | − | +/− | + | ++ |
| MS-PRO12 | − | +/− | − | ++ |
| MS-PRO13 | − | +/− | +/− | + |
| MS-PRO14 | − | − | − | + |
| LY6.3 (control) | − | − | | |

In most cases, the data generated in both laboratories are in agreement. However, some Fabs behave differently. For example, MS-PRO3 and MS-PRO-10 were found to be completely FGFR3-specific under certain conditions while under other conditions both show considerable cross-reaction with FGFR1. Subsequent FACS analysis supported the cross reactivity for MS-PRO3, but not for MS-PRO10. Taking into account the potency and specificity of the Fabs, MS-PRO2 had the highest score according to these preliminary data.

Example 5

Affinity of Fab to FGFR3

The affinity measurements were performed by BIA-CORE® analysis according to the standard procedure recommended by the supplier (Pharmacia). The anti-Fc antibody was coupled via the EDC/NHS chemistry to the chip and subsequently FGFR3 was captured. The Fabs of the invention were then bound to this surface.

Table 5 shows a comparison of affinities of Fabs candidates to FGFR3 as determined by BIACORE® and by FACS-scatchard.

TABLE 5

Comparison of Antibody Affinities to FGFR3 determined by BIAcore ® and FACS-Scatchard

| Fab clone | BIAcore ® [nM] | Indirect FACS-Scatchard [nM] |
| --- | --- | --- |
| MSPRO2 | 37 ± 10 | 43 |
| MSPRO11 | 4 ± 2 | 4 |
| MSPRO12 | 14 ± 2 | 6.5 |
| MSPRO21 | 9 ± 2 | 0.6 |
| MSPRO24 | 10 ± 2 | 0.3 |
| MSPRO26 | 4 ± 1 | 1.4 |
| MSPRO28 | 9 ± 0.4 | 0.3 |
| MSPRO29 | 6 ± 4 | 0.4 |

Table 1E (in the Detailed Description, vide supra) shows the affinity as determined by BIACORE® for the Fab candidates shown in Table 5 converted into the Fab mini-antibody format, Fab-dHLX-MH, where a dimer of the Fab monomer is produced after insertion into an expression vector as a fusion protein.

Table 6 shows the results of a competition assay wherein each MSPRO Fab was bound to FGFR3 at a concentration of 500 nM or 1,000 nM and coinjected in pairs with the other MSPRO Fabs. The (−) indicates binding to the same or nearby epitope while (+) indicates binding to different epitope. The results show that MSPRO2 and 12 bind to the same or nearby epitope while MSPRO 11, 21, 24, 26, 28 and 29 bind to an epitope different from that of MSPRO 2 or 12.

TABLE 6

| | 2 | 11 | 12 | 21 | 24 | 26 | 28 | 29 |
| --- | --- | --- | --- | --- | --- | --- | --- | --- |
| 2 | | + | − | + | + | + | + | + |
| 11 | + | | + | − | − | − | − | − |
| 12 | − | + | | + | + | + | + | + |
| 21 | + | − | + | | − | − | − | − |
| 24 | + | − | + | − | | − | − | − |
| 26 | + | − | + | − | − | | − | − |
| 28 | + | − | + | − | − | − | | − |
| 29 | + | − | + | − | − | − | − | |

Example 6

Specific Neutralizing Activity of the Antibodies

A: FDCP Cell Proliferation Assay

The FDCP cell line is a murine immortalized, interleukin 3 (IL-3) dependent cell line of myelocytic bone marrow origin, which does not express endogenous FGF Receptors (FGFR). Upon transfection with FGFR cDNA, the FDCP cell line exhibits an FGF dose-dependent proliferative response that can replace the dependence on IL-3. FDCP cell lines, transfected with FGFR cDNAs can therefore be used to screen for specific inhibitors or activators of FGFR, as well as for analyzing FGFR signaling. The FDCP cell response to various ligands was quantitated by a cell proliferation assay with XTT reagent (Cell Proliferation Kit, Biological Industries Co.). The method is based on the capability of mitochondrial enzymes to reduce tetrazolium salts into soluble colored formazan compounds which can be quanititated and is indicative of cell viability. Specifically, FDCP cells expressing FGFR3IIIb, FGFR3IIIc or FGFR1 were grown in "full medium" (Iscove's Medium containing 2 ml glutamine, 10% FCS, 100 ug/ml penicillin, 100 ug/ml streptomycin) supplemented with 5 ug/ml heparin and 10 ng/ml FGF9. Cells were split every 3 days and kept in culture no more than one month. One day prior to the experiment, the cells were split. Before the experiment, the cells were washed 3 times (1000 rpm, 6 min) with full medium. Later, the cells were resuspended and counted with Trypan Blue. Twenty thousand (20,000) cells per well were added to wells in a 96-well plate in 50 ul in full medium containing 5 ug/ml heparin. Conditioned medium was added in an additional volume of 50 ul full medium containing FGF9 at varying concentrations to a final volume of 100 ul. A primary stock solution (usually 2× the higher concentration) of the antibody (or Fabs) was prepared in Iscove's+++ containing 5 µg/ml heparin and 2.5 ng/ml FGF9 or IL-3 (final concentration 1.25 ng/ml). Dilutions were filtered in a 0.2 µm syringe nitrocellulose filter blocked first with 1 mg/ml BSA and washed then with Iscove's+++. Aliquots of requested serial dilutions were prepared. Dilutions were kept on ice until use. 50 µl of the corresponding 2× final concentration was added to each well and the plate was incubated at 37° C. for either 40 hours or 64 hours. After incubation, the reaction was developed as follows: 100 µl of activator solution was added to 5 ml XTT reagent and mixed gently. 50 µl of mixture was added to each well. Optical density (OD) at 490 nm at this point gave the zero time reading.

Cells were then incubated at 37° C. for 4 hours (in the case of a 40-hour incubation) or 2 hours (in the case of a 64-hour incubation) and proliferation was measured by O.D. at 490 nm (A490).

It is noted that the assay is successful when the O.D. of untreated control growing with saturated amounts of FGF (10 and 20 ng/ml) is at least 1.3 O.D. units. Furthermore, it is noted that the background of wells with no cells should be 0.2-0.35 O.D. units and that the O.D. absorbance of 1.25 ng/ml FGF9 should not be less than 40% of the O.D. absorbance achieved with saturated FGF 9 concentration (10 and 20 ng/ml). Specific inhibition of FGF and FGF receptor mediated proliferation should always be accompanied with lack of any inhibition of the same antibody concentration on IL-3 dependent cell proliferation.

The following FDCP cell lines were used:
  *FDCP-C10 (C10): FDCP cells transfected with the human wild-type FGFR3IIIc.
  *FDCP-R3: FDCP cells transfected with the human wild-type FGFR3IIIb.
  *FDCP-R1: FDCP cells transfected with the human wild-type FGFR1.
  *FDCP-F3Ach: FDCP cells infected with human FGFR3 mutated at amino acid Glycine 380 to Arginine (G380R), analogous to the most common human achondroplasia mutation.

B: Neutralizing Activity

The neutralizing activity of the antibodies was measured by the aforementioned cell proliferation analysis in FDCP-FR3 and FDCP-FR1 cell lines and is presented in FIG. 5. Increasing amounts of the indicated Fabs (MSPRO 2, 3 and 4)

were added to FDCP-FR3 (closed triangle ? (2), star * (3), and circle ? (4)) or FDCP-FR1 (open triangle ? (2), open square ? (3) and open circle ? (4)) grown in the presence of FGF9. Two days later, an XTT proliferation assay was performed. While none of the Fabs inhibited FDCP-FR1 cell proliferation, MSPRO2 (?) and MSPRO3 (*) inhibited FDCP-FR3 proliferation with a similar IC50 of about 1.0 µg/ml. In contrast, MSPRO4 (?) had no inhibitory effect on FDCP-FR3 proliferation. The rest of the Fabs, MSPRO 1, 3, 5, 6, 7, 9, 11, 12, 13, 14, were similarly analyzed on FDCP-FR3 expressing cells. Increasing amounts of the indicated Fabs were added to FDCP-FR3 grown in the presence of FGF9 (FIG. 6). Inhibitors of FGFR3 signaling were antibodies MSPRO 1, 3, 5, 7, 9, 11, 12. The results of the proliferation assay done at two sites are compared in Table 7 (NA=data not available).

TABLE 7

|  | Prochon | | MorphoSys | |
| --- | --- | --- | --- | --- |
|  | FDCP-FR1 | FDCP-FR3 | FDCP-FR1 | FDCP-FR3 |
| MSPRO1 | − | ++ | NA | NA |
| MSPRO2 | − | ++ | NA | ++ |
| MSPRO3 | − | ++ | NA | ++ |
| MSPRO4 | − | − | NA | − |
| MSPRO5 | − | + | NA | + |
| MSPRO6 | − | − | NA | +/− |
| MSPRO7 | − | ++ | NA | + |
| MSPRO8 | − | +/− | NA | +/− |
| MSPRO9 | − | + | NA | + |
| MSPRO10 | − | + | NA | NA |
| MSPRO11 | − | +++ | NA | ++ |
| MSPRO12 | − | +++ | NA | +++ |
| MSPRO13 | − | − | NA | NA |
| MSPRO14 | − | − | NA | NA |
| LY6.3 | − | − | NA | NA |

As shown in Table 7, there is an excellent agreement between the data. About half of the Fabs show considerable neutralizing activity, MSPRO12 being the most potent. Most of the inhibitory Fabs performed well in the binding assay (Table 4), with MSPRO11 and MSPRO12 being the exception to the rule, however, clearly remain good candidates to pursue. None of the Fabs (including those that crossreact with FGFR1) inhibited FGF-dependent FDCP-FR1 proliferation. In addition, FDCP-FR3 cells grown in the presence of IL-3 were not affected by any of the Fabs.

Figure 7A:
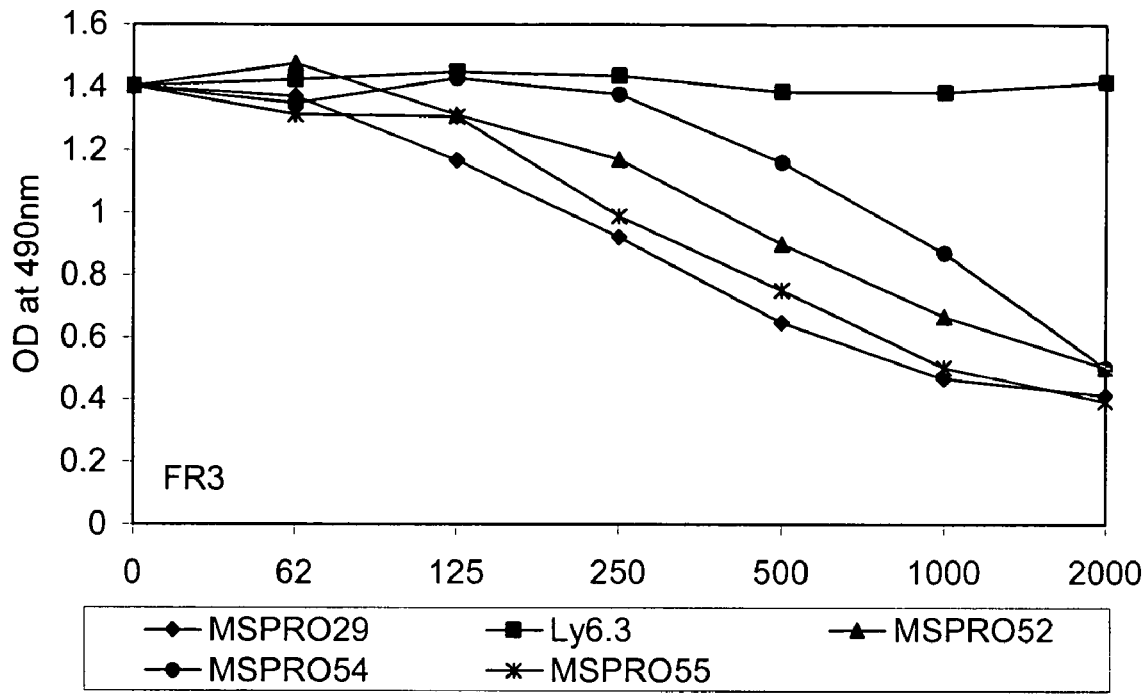
FIGS. 7A and 7B show the neutralizing activity of several MSPRO Fabs in a proliferation assay using the FDCP-FR3 (C10.
Figure 7B:
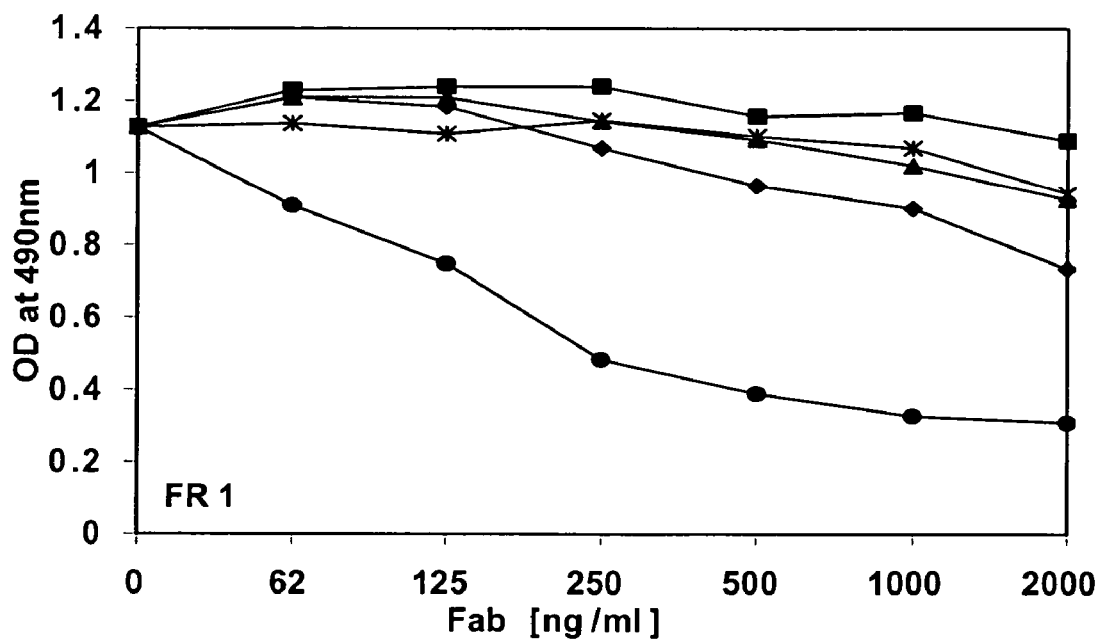

An additional 20 new Fabs were selected from the second panning. Three of these new Fabs were subjected to the FDCP cell proliferation test and all were found to neutralize the receptor (MSPRO52 (?), MSPRO54 (?) and MSPRO55 (*) in FIG. 7A). Interestingly and in accord with MorphoSys affinity data, one Fab (MSPRO54) showed strong neutralizing activity against FGFR1 (FIG. 7B). MSPRO29 (?) and a control antibody Ly6.3 (|) were also tested in this assay.

Example 7

Receptor Expression and Activation in RCJ Cells

RCJ Cell Assay

Figure 21:
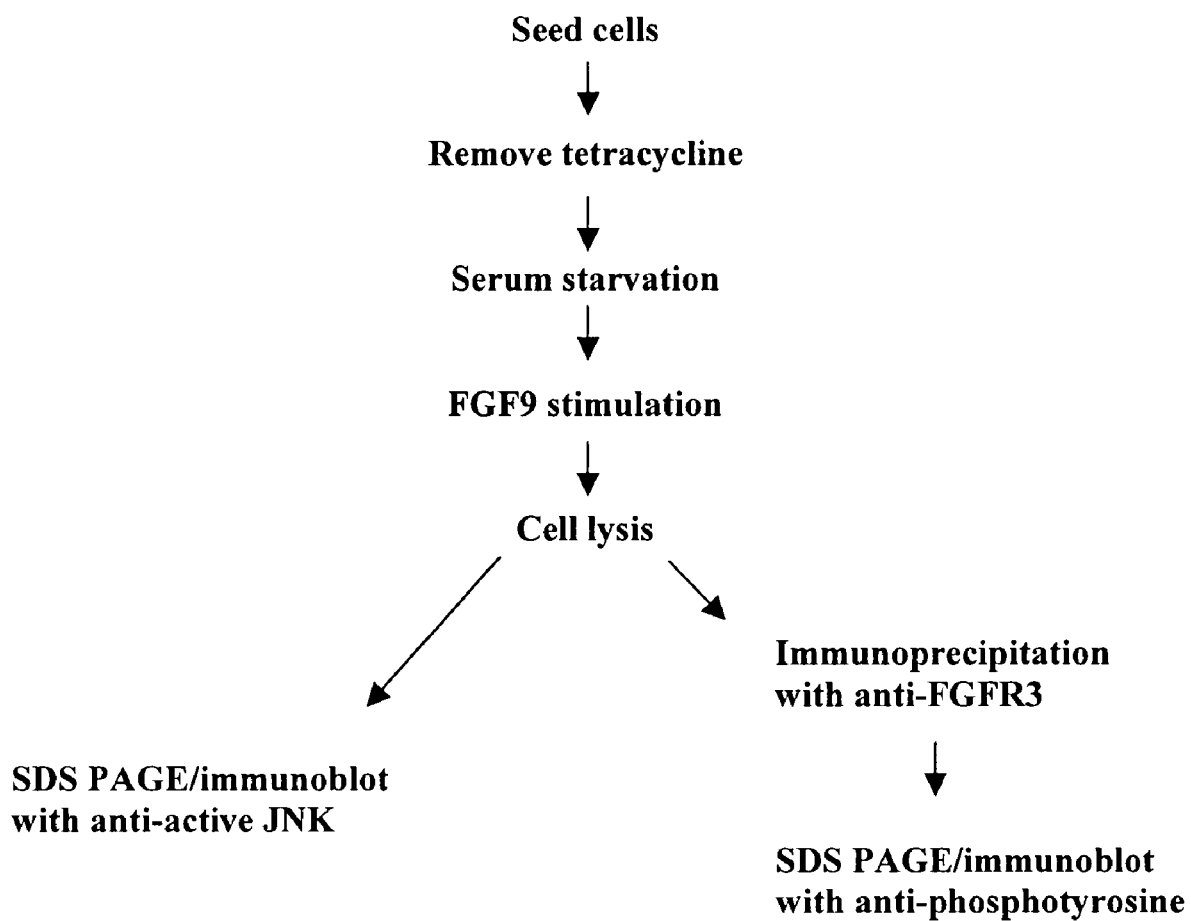
FIG. 21 is a flow chart of the experimental protocol for assessing receptor activation and signaling.

RCJ cells (fetal rat calvaria-derived mesenchymal cells, RCJ 3.1C5.18; Grigoriadis, 1988) were generated to express various FGF Receptors in an inducible manner, in the absence of tetracycline. The M14 line (RCJ-FR3ach) expresses FGFR3-ach380 mutant upon induction by the removal of tetracycline. The cells were incubated in low serum after which FGF was added to stimulate receptor function and signaling. The cells were lysed and the receptor level, receptor activation and signaling are assessed by Western with anti-active ERK (or JNK) (Promega). The lysates is immunoprecipitated with anti-FGFR3 (Santa Cruz), and a Western immunoblots is prerformed using anti-phospho-tyrosine (Promega) antibodies. W11 refers to the RCJ cells expressing wild type FGFR3. RCJ-FR1 and RCJ-FR2 refer to RCJ cells expressing the FGFR1 and FGFR2 receptors, respectively. FIG. 21 provides a flow chart of the experimental procedure.

The transfected RCJ cells were grown in a-MEM supplemented with 15% fetal calf serum, 1× penicillin/streptomycin/nystatin, 1× glutamine, 600 µg/ml neomycin, 2 µg/ml tetracycline, 50 µg/ml hygromycin B to subconfluence. The medium was aspirated off and the cells washed with trypsin, 1 ml/10 cm dish, then trypsinized with 0.5 ml/10 cm dish. The cells were resuspended in 10 ml a-MEM supplemented with 15% fetal calf serum, 1× penicillin/streptomycin/nystatin, 1× glutamine, 600 µg/ml neomycin, and 2 µg/ml tetracycline.

Six hundred thousand ($6\times10^6$) cells/well were seeded in a 6-well dish. The cells were washed thrice 24 hours later (or 8 hours later if twice the amount of cells are seeded) with 1 ml a-MEM, and then incubated with a-MEM supplemented with 15% fetal calf serum, 1× penicillin/streptomycin/nystatin, and 1× glutamine (induction medium) for 16 hours. Cells were washed thrice with 1 ml a-MEM and allowed to grow for 4 additional hours in 1 ml of 0.5% exhausted serum (prepared by diluting the induction medium X30 with a-MEM).

FGF9 (1 ng/ml) was added for 5 minutes and the cells placed on ice. The cells were washed twice with ice-cold PBS and lysed with 0.5 ml lysis buffer. The cells were scraped into an Eppendorf tube, vortexed once and placed on ice for 10 minutes. The lysate was microcentrifuged for 10 minutes at 4° C., and the cleared lysate was transferred into a fresh Eppendorf tube.

The protein content was determined by Bradford or DC protein assay (Bio-Rad, cat# 500-0116) following manufacture instructions. Total protein aliquots, supplemented with 1/5 volume of 5× sample buffer, were boiled for 5 minutes and stored at −20° C. until ready to load on gel. In parallel an immunoprecipitation (IP) assay was performed, 10 µl anti-FGFR3 antibodies were added to the rest of the lysates and incubated for 4 hours at 40° C. Twenty (20) ul protein A-SEPHAROSE® was added and incubated for 1 hour at 4° C. with continuous shaking. Afterwards, the mixture was microcentrifuged 15 seconds, and the fluid was aspirated, carefully leaving a volume of ~30 µl above the beads. The beads were washed 3 times with 1 ml lysis buffer. At this step, the protease inhibitor mix was omitted from the buffer.

After the final wash, 15 µl of 5× sample buffer was added, samples were boiled 5 minutes and stored at −20° C. until ready to load onto gel. Samples were loaded onto a 7.5% SDS-PAGE, cast on a Mini-PROTEAN II electrophoresis cell, and run at 100 V through the upper gel and at 150 V through the lower gel. Proteins were transferred onto a nitrocellulose sheet using the Mini trans-blot electrophoretic transfer cell at 100 V for 75 minutes or at 15 V overnight. The lower part of the total lysate Western blots was probed with anti-active JNK (anti-phosphorylated Jun Kinase) and the upper part was probed with anti-FGFR3, both at $5\times10^3$ dilutions.

Figure 8A:
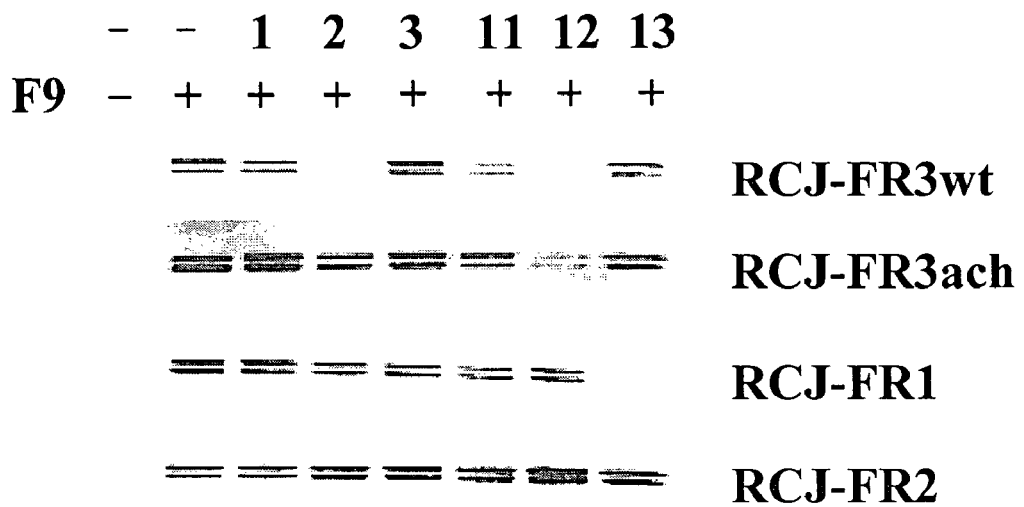
Figure 8B:
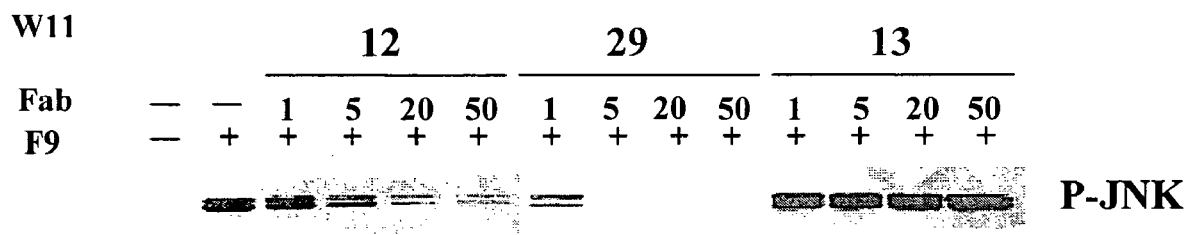
FIG. 8B shows a dose response of MSPRO 12, 29 and 13 on RCJ-FR3 cells.

FIG. 8A shows that MSPRO2 blocks FGFR3 activation in W11 cells and weakly blocks signaling in M14 cells, and MSPRO12 blocks FGFR3 receptor activation in W11 and M14 expressing cells. Furthermore MSPRO13 appeared to be able to block FGFR1 activation while none of the Fabs blocked FGFR2 activation. FIG. 8B shows the inhibitory capacity of MSPRO12 and MSPRO59 on wild type FGFR3 expressing cells, as seen as reduction in JNK signaling.

MSPRO29 strongly inhibits FGFR3 activation (<5 ug), MSPRO12 has an inhibitory effect but at a higher concentration (5-20 ug).

The IP lysate Western blots were probed with anti-phosphotyrosine (R&D Systems). Hybridization was detected by ECL following the manufacturer's instructions.

Figure 9A:
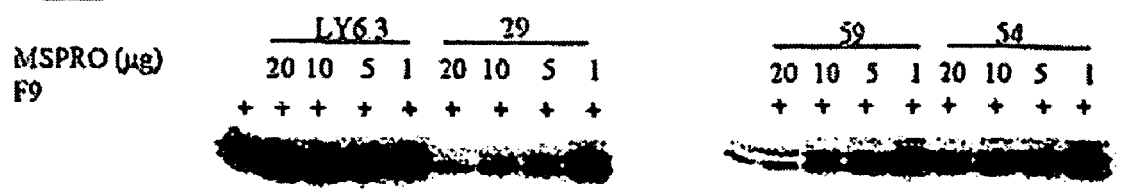
FIG. 9A shows a dose response of MSPRO 29, 59 and 54 on RCJ-M14 cells.
Figure 9B:
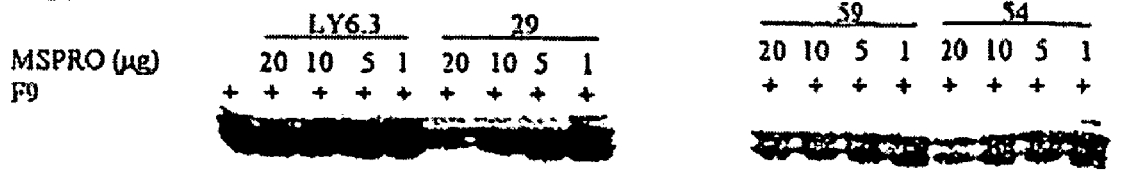
FIG. 9B shows a dose response of MSPRO 29, 59 and 54 on RCJ-W11 cells.
Figure 9C:
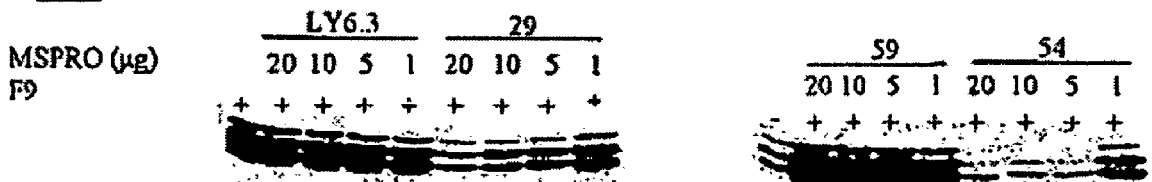
FIG. 9C shows a dose response of MSPRO 29, 59 and 54 on RCJ-R1-1 cells.
Figure 9D:
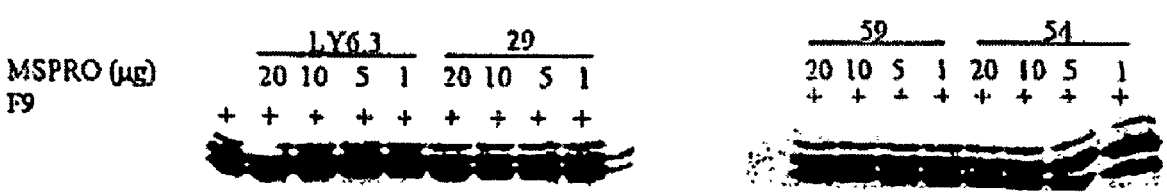
FIG. 9D shows a dose response of MSPRO 29, 59 and 54 on RCJ-R2-2 cells.

BIACORE® and proliferation analyses showed that among the new Fabs, MSPRO54 is highly cross reactive with FGFR1. To further test the cross reactivity of the new Fabs, RCJ cells expressing either FGFR3ach (RCJ-M14; M14 on FIG. 9A) FGFR3 wild type (W 11 on FIG. 9B), FGFR1 (R1-1 on FIG. 9C) or FGFR2 (R2-2 on FIG. 9D) were incubated with increasing amount of a control antibody LY6.3, MSPRO29, 54 and 59 for one hour. FGF9 was added for 5 minutes and cell lysates were analyzed by Western blot for ERK activation (phosphorylated ERK; pERK) (FIGS. 9A, 9B, 9C and 9D). Furthermore, MSPRO13 was able to block FGFR1 activation while none of the Fabs blocked FGFR2 activation. FIGS. 9A. 9B, 9C and 9D show the results of several Fabs, at different mg concentrations, on RCJ expressing wildtype FGFR3 or the different FGFR types. MSPRO29 appeared as the best FGFR3 blocker and was also effective in blocking FGFR1 (FIG. 9c); however, MSPRO54 was the most effective Fab against FGFR1. None of the Fabs significantly inhibited FGFR2 activity. There are only a few amino acid residues within the third Ig domain that are shared by FGFR3 and FGFR1 but not by FGFR2. Making mutants at these sites should clarify their role in Fab-receptor binding.

Example 8

Epitope Mapping of Selected Fabs

Figure 10:
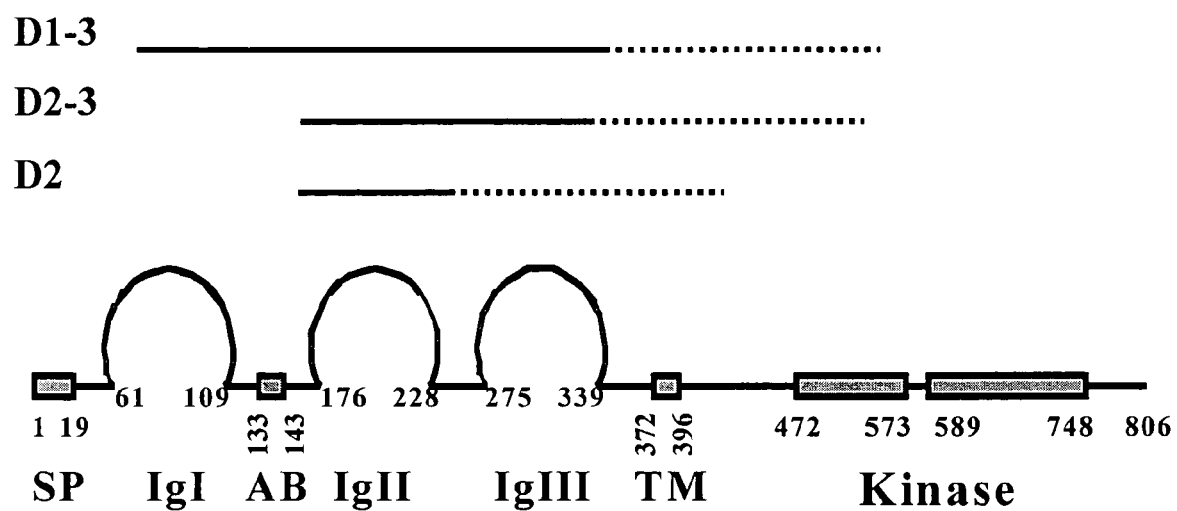
FIG. 10 shows a diagrammatic representation of FGFR3 and of FGFR3 truncations (D2-3, D2) and isoforms (IIIb, IIIc). The isoform IIIb differs from IIIc at the carboxy terminus of the IgIII domain as indicated with a dotted line.
Figure 11:
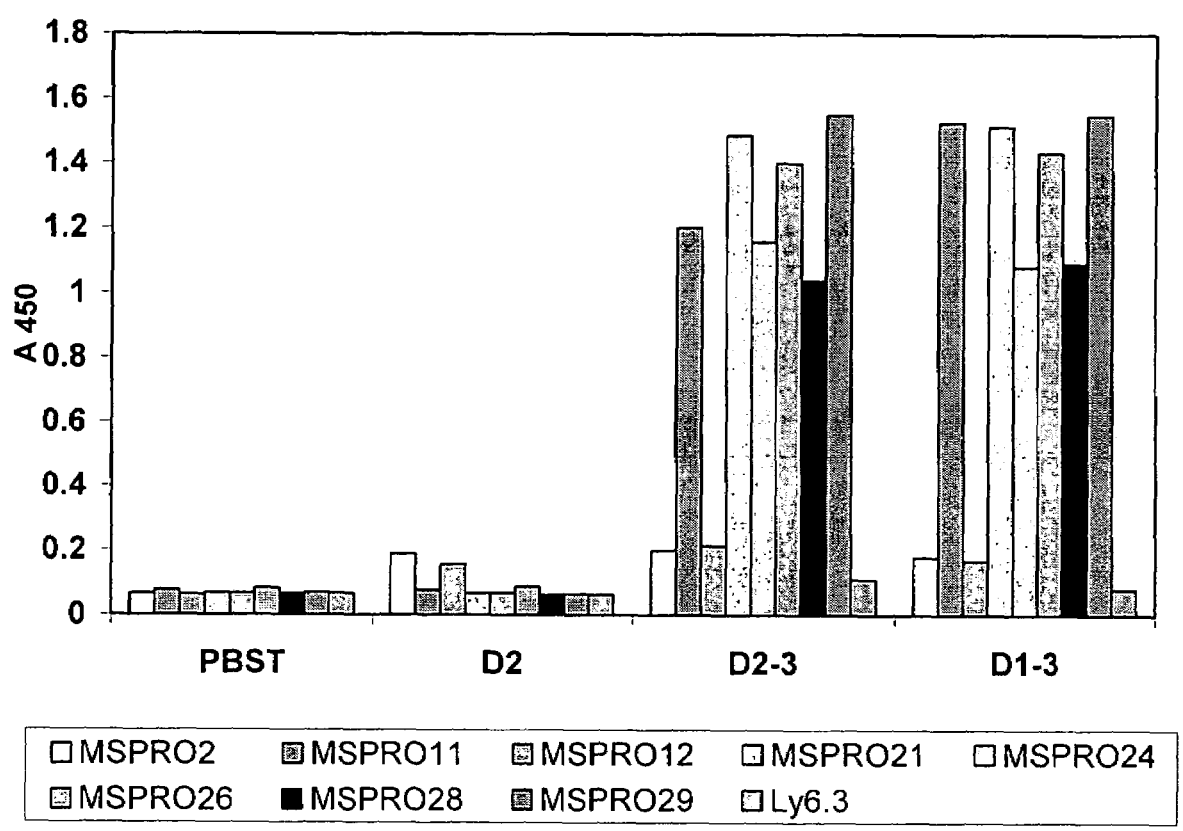
FIG. 11 shows that the FGFR3 neutralizing Fabs recognize IgII or IgII and III in the extracellular region of FGFR3.
Figure 12:
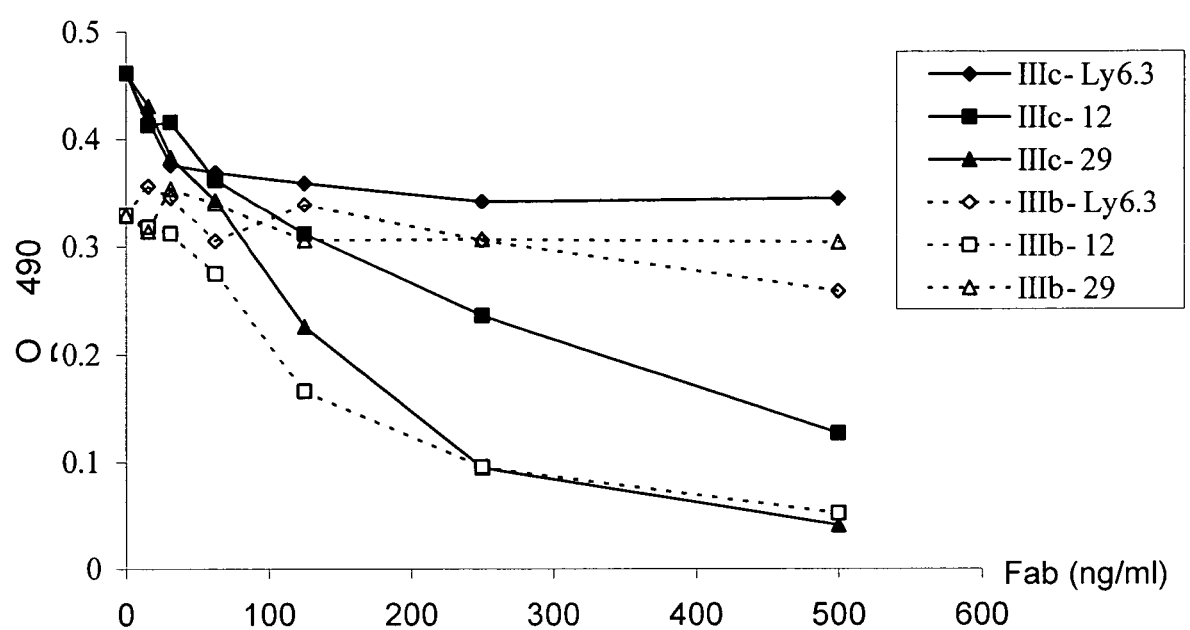
FIG. 12 shows the proliferation level of FGFR3IIIb and FGFR3IIIc expressing cells in the presence of MSPRO29. MSPRO 29 specifically recognizes the IIIc isoform of FGFR3.

Constructs comprising cDNAs that code for segments of the extracellular domain of FGFR3 were generated (FIG. 10). D2 comprises Ig domain 2, D2-3 comprises Ig domains 2 and 3, and D1-3 comprises Ig domains 1, 2 and 3. These constructs include pChFR3$^{D2}$Fc that codes for Ig-like domain 2 of FGFR3 and pChFR3$^{D2,3}$Fc that codes for domain 2 and 3, both as human Fc fusions. The corresponding chimeric proteins, as well as the control hFR3exFc (containing domains 1, 2 and 3) were anchored to an ELISA plate coated with a human Fc antibody. A panel of 8 best Fabs, MSPRO2, 11, 12, 21, 24, 26, 28 and 29, were added, and bound Fab was determined with HRP-a human Fab (FIG. 11). The results in FIG. 11 demonstrate that MSPRO2 (speckled bar) and MSPRO12 (diagonally hatched bar) differ from the other tested Fabs. Both bind to the Ig like domain 2 while the others require domain 3 for binding. It was then tested whether or not Fabs that belong to the second group would distinguish the FGFR3IIIc isoform from the FGFRIIIb from. FDCP-FR3IIIb or FDCP-FR3IIIc cells were incubated in the presence of 1.25 ng/ml FGF9 with increasing doses of either MSPRO12 or MSPRO29. Ly6.3 was included as control. After 2 days in culture, cell proliferation was measured with the XTT reagent. Clearly, MSPRO29 (open triangle) was completely ineffective against the IIIb isoform (FIG. 12). In contrast, MSPRO12 (square on hatched or solid lines) was equally effective against both isoforms. These data suggest that residues that differ between the two isoform are critical for MSPRO29 (and probably also for the other Fabs in the same group) FGFR3 binding.

Domains in FGFR3 Recognized by the New Fabs

From the data presented, MSPRO antibodies can be divided into 2 groups, one that includes Fabs that bind the FGFR3 Ig II domain (MSPRO2 and 12) and a second with members that require the Ig III domain for binding (MSPRO11, 21, 24, 26, 28, and 29). To classify the new Fabs obtained from the last screen, as well as some previously obtained Fabs, a proliferation assay of FDCP cells expressing either FR3IIIb or FR3IIIc was performed. The cells were incubated in the presence of 10 (IIIb) or 5 (IIIc) ng/ml FGF9 with increasing doses of the indicated Fabs. After 2 days in culture, cell proliferation was measured with the XTT reagent.

The data shows that MSPRO59 (*) efficiently inhibited both FDCP-FR3IIIb (FIG. 13A) and FDCP-FR3IIIc cells (FIG. 13B), while MSPRO21, 24, 26, 28, 29 and 54 inhibited FDCP-FR3IIIc proliferation only.

Example 9

Bone Culture

Radiolabeled MSPRO29 was used to determine whether MSPRO Fabs are able to penetrate the bone growth plate.

Figure 14:
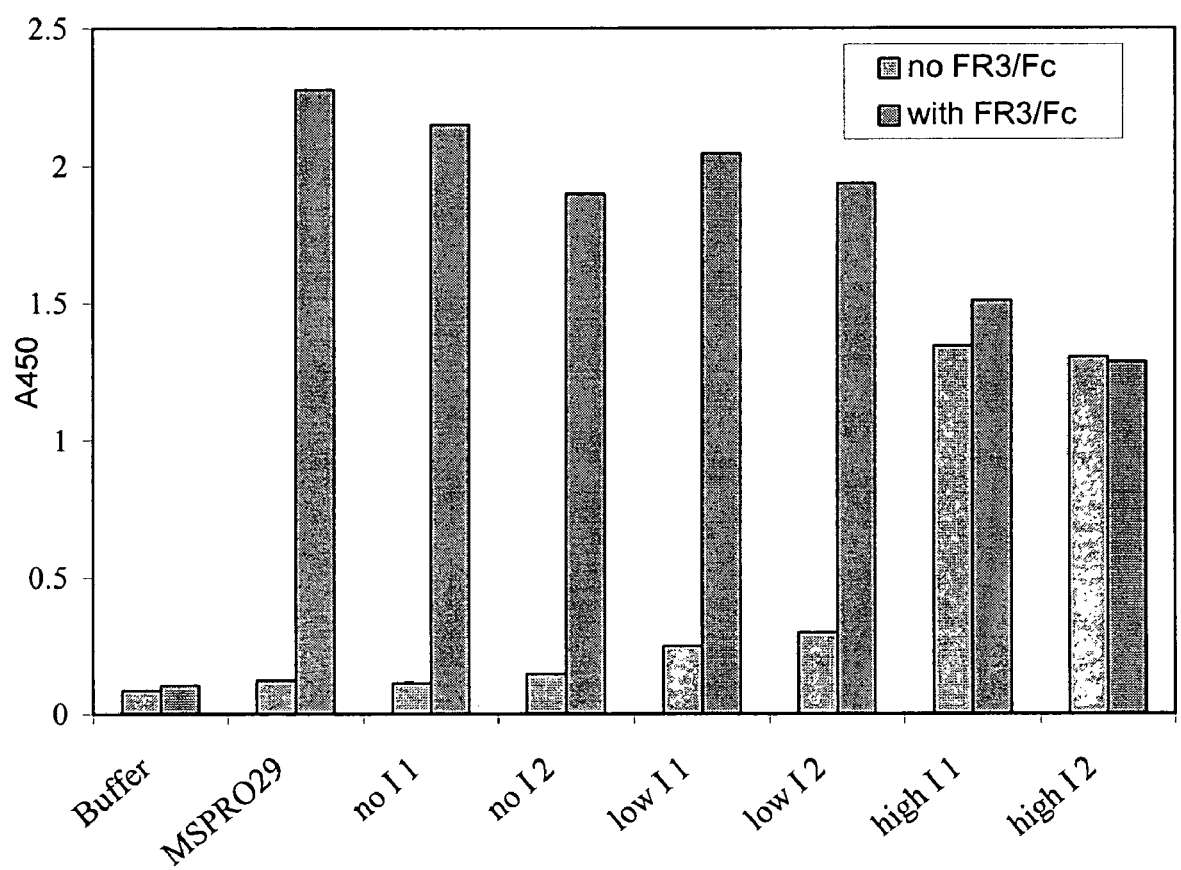
FIG. 14 shows iodinated MSPRO29 binding to FGFR3.

To determine the effect of iodination on Fab activity, 50 μg of MSPRO29 was first labeled with cold iodine using Pierce IodoGen coated tubes. The process was carried out either without iodine, with 0.04 mM NaI (low I) or with 1 mM NaI (high I). MSPRO29 was then purified through a SEPHADEX® G-50 column. The ability of the modified Fab to bind FGFR3 was determined by ELISA. MAXISORP® wells were coated with anti-human Fc. FGFR3/Fc was then anchored to the wells. In parallel, a similar set of wells was left in blocking buffer only (no FR3/Fc, hatched bars). The unmodified (no I) or the modified MSPRO29 (low or high, 2 G-50 fractions each, 1 and 2) were added at approximately 5 μg/well and binding was measured with anti-human Fab. Fresh MSPRO29 and buffer alone were included as controls (FIG. 14: FGFR3/Fc, checkered bars; no FGFR3/Fc, hatched bars). MS-PRO29 was labeled with 1 mCi $^{125}$I. The specific activity of the Fab was 17 μCi/μg.

MSPRO29 labeled in the presence of 0.04 mM NaI showed equal binding to the receptor as compared to the control unmodified Fab. MSPRO29 labeled in the presence of 1 mM NaI (high I, 1 and 2) also bound the receptor, however, the noise level of this sample was as high as the signal itself suggesting that at the high iodide concentration the Fab was inactivated.

The neutralizing activity of the modified Fab was tested in a proliferation assay using FDCP-FR3 (C10) (FIG. 15). FDCP-FR3 (C10) cells were treated with the indicated amount of labeled or unlabeled (without I) MSPRO29. The proliferation rate of the cells was determined by XTT analysis. The Fab was labeled at either 0.04 mM (Low) or 1 mM NaI (High). Two G-50 fractions (1 and 2) were analyzed. Fresh MSPRO29 and buffer alone (mock) were included as controls.

This experiment showed that MSPRO29, labeled at 0.04 mM NaI, maintained its inhibiting activity almost entirely while MSPRO29 labeled at 1 mM NaI had indeed lost its activity completely.

Ex Vivo Distribution of $^{125}$I MSPRO29 in Bone Culture

Femora prepared from newborn mice were incubated with 2 μg $^{125}$I-MSPRO29 (17 μCi/μg) or $^{125}$I-Ly6.3 (20 μCi/μg) for 1, 3 or 5 days in culture. Then, sections were processed for radiomicroscopy. After 3 days in culture, MSPRO29 was predominantly visualized at the higher hypertrophic zone and to a lesser extent at the secondary ossification region FIGS. 16A, 16B 16C, 16D, 16E and 16F). Hematoxylin-eosin staining of growth plate treated with radiolabeled MSPRO29 or Ly6.3 (FIGS. 16A and 16D, respectively) ×100 magnification. Radiomicroscopic sections of growth plate treated with radiolabeled MSPRO29 or Ly6.3 (FIGS. 16B and 16E) at ×100 magnification. FIGS. 16C and 16F are the same as FIGS. 16B and 16E but at ×400 magnification. The arrows in FIGS. 16B and 16C indicate the location of the specific binding of the radiolabelled MSPRO29 to the higher hypertrophic zone of the growth plate.

As compared to MSPRO29, the control Ly6.3 Fab was weakly and evenly distributed throughout the whole growth plate. At day 1 in culture, the signal was weaker but with similar distribution pattern. This distribution also holds at 5 days in culture with a less favorable signal to noise ratio (data not shown). This clearly demonstrates that MSPRO29 binds FGFR3 in our target organ.

Example 10

Neutralization of Constitutively Active Receptors

The inhibitory activity of MSPRO antibodies on ligand-dependent and ligand-independent FDCP proliferation expressing FGFR3 Achondroplasia mutation was tested.

Figure 17A:
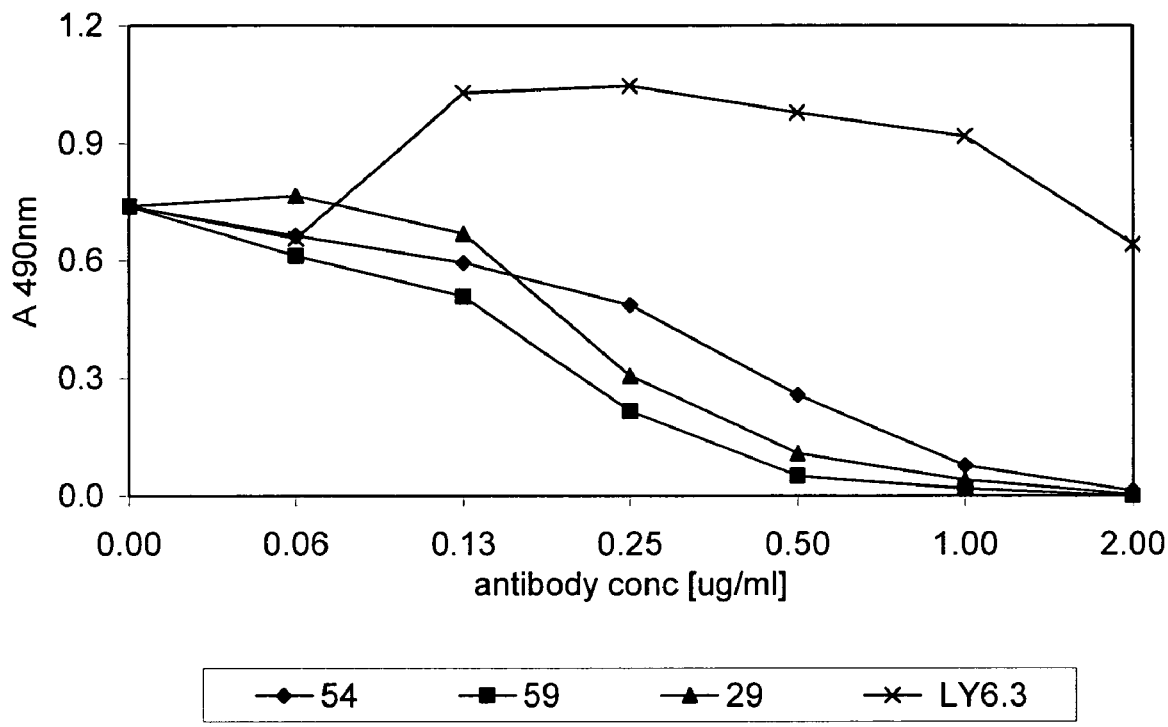
FIGS. 17A and 17B show a proliferation assay of FDCP-FR3 (17A) and FDCP-FR3ach cells (17B) incubated with FGF9 and with increasing doses of indicated Fabs.
Figure 17B:
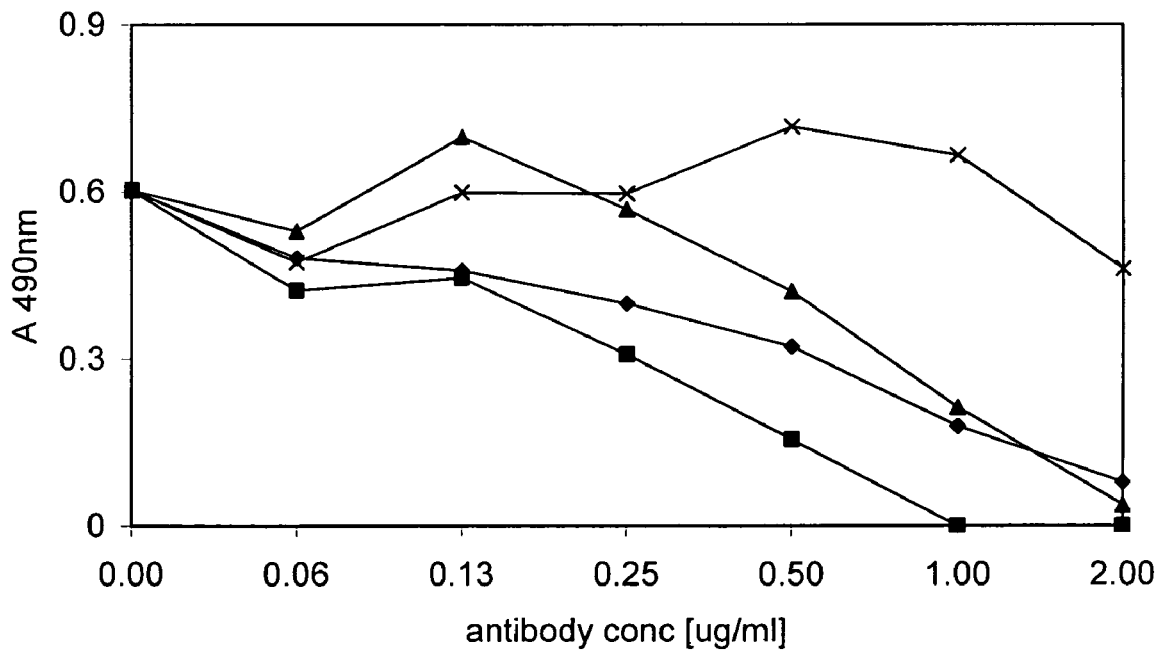

A proliferation assay was carried out using FDCP-FR3wt (C10, FIG. 17A) or FDCP-FR3ach cells (FIG. 17B) incubated with 1.25 or 5 ng/ml FGF9 respectively and with increasing amounts of MSPRO54 or MSPRO59. As shown in FIG. 17, both MSPRO54 (diamond ?) and 59 (square ¦) antibodies neutralize the mutant receptor. FDCP-FR3ach acquired ligand independent cell proliferation due to the high expression of the FGFR3ach mutation. MSPRO29 (?) inhibits the FDCP-FR3wt activity at a level similar to MSPRO54 and 59 but is less effective in inhibiting the FGFR3ach receptor in this assay system.

Figure 18A:
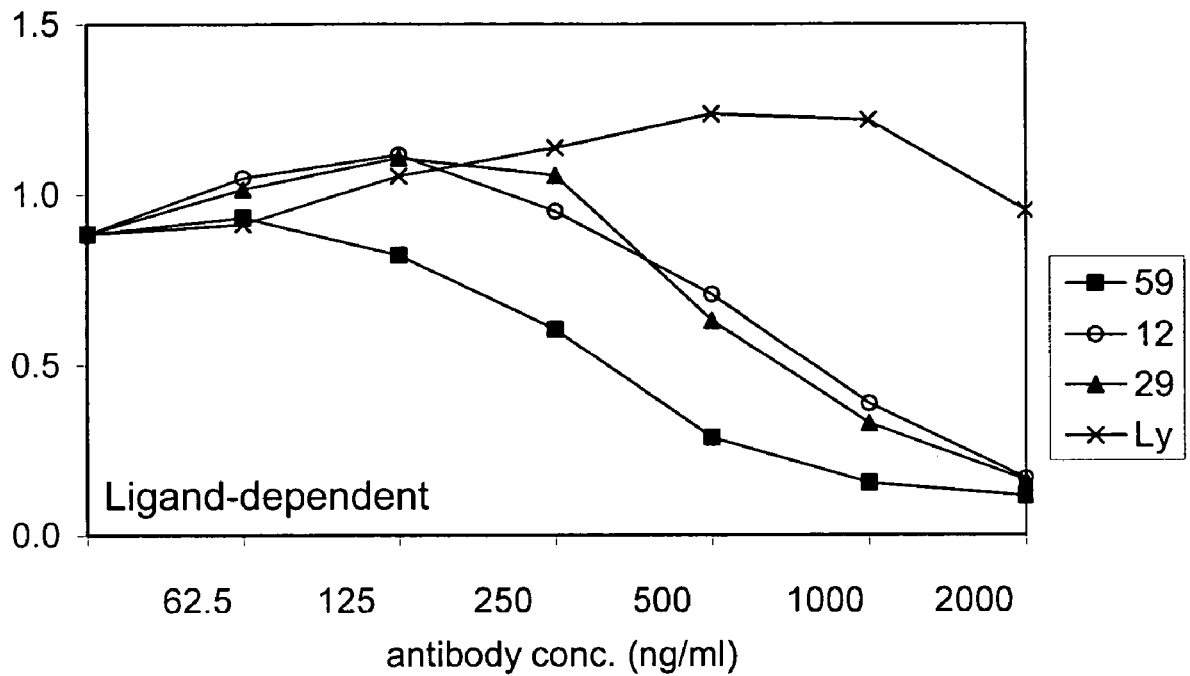
FIG. 18A shows analysis of the ligand-dependent FDCP-FR3 wt cells.
Figure 18B:
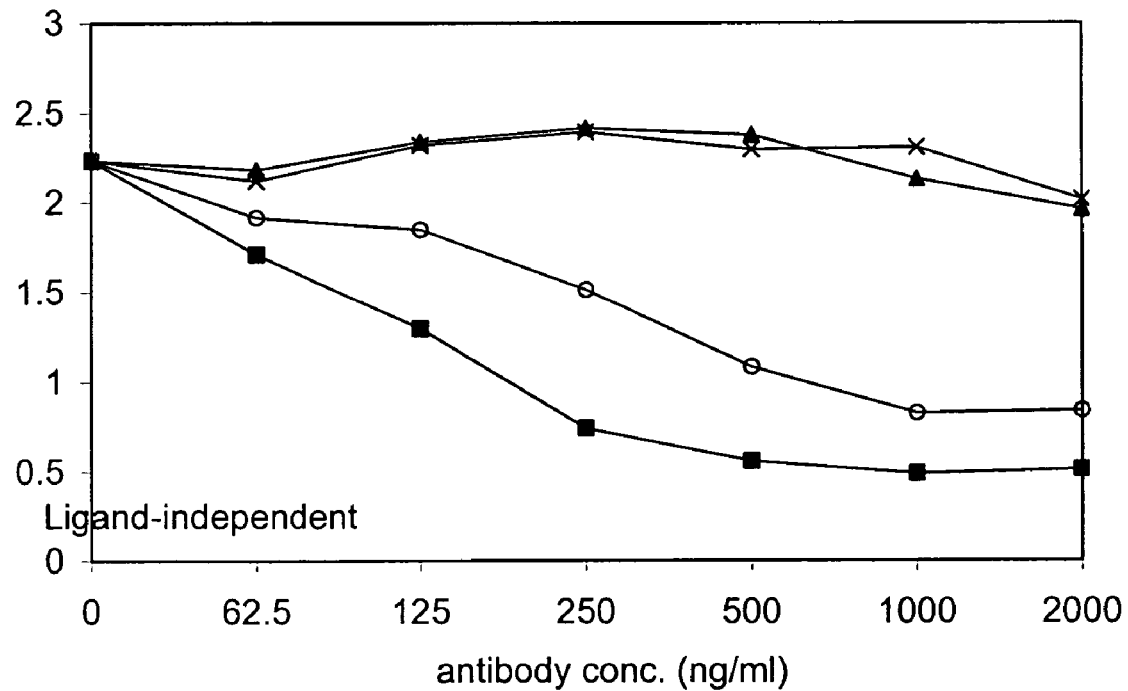
FIG. 18B shows that MSPRO12 and MSPRO59 inhibit the ligand independent proliferation of FDCP-FR3ach cells.

FDCP cells that express the achondroplasia FGFR3 (FDCP-FR3ach) and proliferate independently of ligand were incubated with the indicated amount of MSPRO12, 29, 59 or the control Ly6.3. Two days later, cell proliferation was determined by an XTT analysis. When inhibition of cell proliferation by the MS-PRO 12, 29, 54 and 59 were tested, only the antibodies 12 and 59 (the only Ab which recognized D2 domain) inhibited the ligand-independent cell proliferation (FIGS. 18A and 18B).

Example 11

RCS Chondrocyte Culture

Effect of Fabs on Growth Arrest of RCS Chondrocytes

RCS is a rat chondrosarcoma derived cell line expressing preferentially high levels of FGFR2 and FGFR3 and low levels of FGFR1 (Sahni, 1999). In this cell line FGFR functions as an inhibitor of cell proliferation similar to its expected role in the achondroplasia phenotype. Analysis of RCS cell proliferation mediated by the addition of different molecules of the invention, showed that MSPRO54 and MSPRO59 were able to restore cell proliferation.

Figure 19:
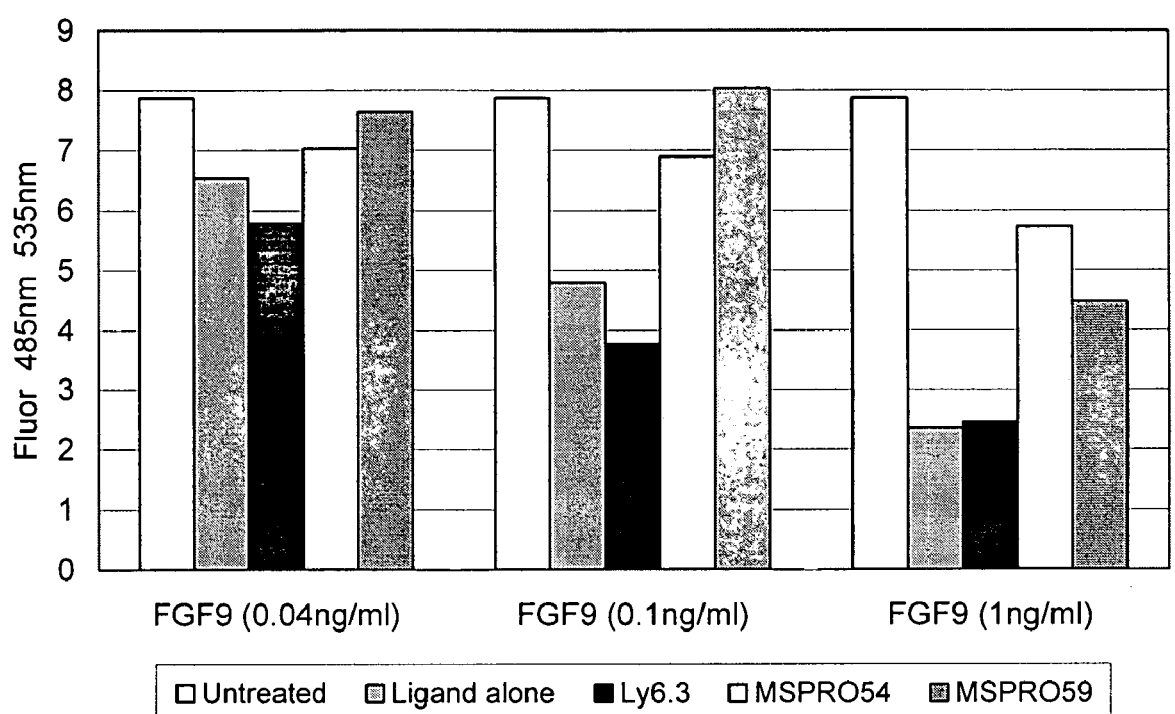
FIG. 19 shows the restoration of cell growth by MS-PRO54 and MSPRO59.

The screening was performed on RCS parental cells in 96 well plates. Cells were seeded at a concentration of 2,000 cells/well. The following day 10 ng/ml FGF-9 and 5 µg/ml heparin were added to the cells. 50 ug/ml of the antibodies were added. Positive and negative controls for cell proliferation are included in this assay at the same concentrations as the tested molecules. On the fourth day of incubation, plates were observed under the microscope. If all cells were viable, no quantitative assay to measure the effect of the variants was performed. If cell death was observed, the Cy-Quant assay kit is used to measure the amount of the cells. The results are measured in a fluoro ELISA reader. FIG. 19 shows the ELISA results in bar graph form. Untreated cells are shown speckled, ligand treated cells are shown in gray, control antibody (LY6.3) treated cells are in black while MSPRO54 and MSPRO59 treated cells are shown in diagonally hatched or checkered bars, respectively.

Example 12

Ex Vivo Bone Culture

The femoral bone cultures were performed by excising the hind limbs of 369-mice, heterozygous or homozygous mice for the achondroplasia G369C mutation (age P0). The limbs were carefully cleaned up from the surrounding tissue (skin and muscles) and the femora exposed. The femora were removed and further cleared from tissue remains and ligaments. The femora were measured for their initial length, using a binocular with an eyepiece micrometer ruler. The bones were grown in 1 ml of medium in a 24 well tissue culture dish. The growing medium is a-MEM supplemented with penicillin (100 units/ml), streptomycin (0.1 mg/ml) and nystatin (12.5 units/ml). In addition, the medium contains BSA (0.2%), a-glycerophosphate (1 mM) and freshly prepared ascorbic acid (50 µg/ml). The bones were cultured for 15 days. Measurements of bone length and medium replacement were performed every three days.

At the end of the experiment, the growth rate of the bones was determined. The growth rate of bones is calculated from the slope of a linear regression fit on the length measurements obtained from day 3 to 9.

Figure 20:
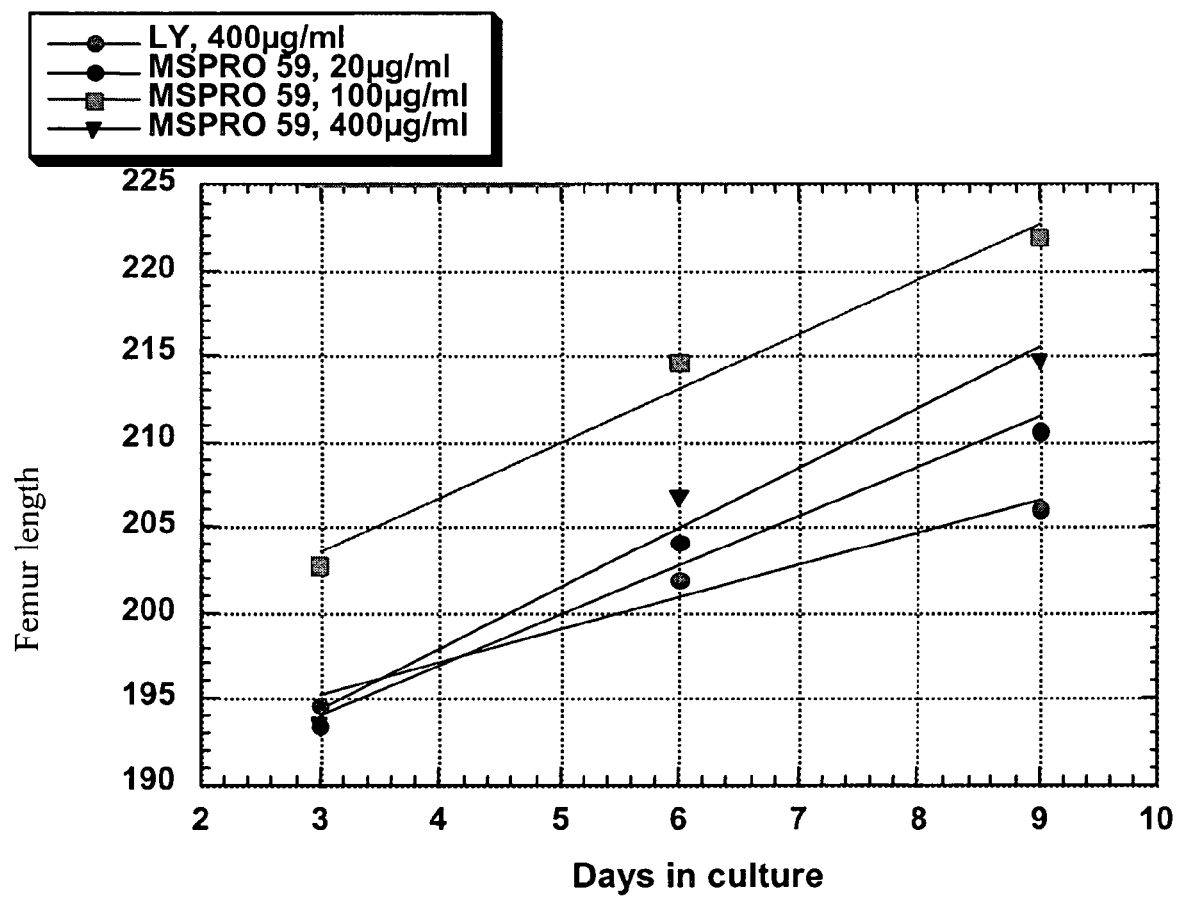
FIG. 20 represents the growth rate of treated bone with MS-PRO 59.

The result, as shown in FIG. 20, demonstrate a dose dependent increase in the growth rate of bones treated with MS-PRO 59 in comparison to non-relevant control LY6.3 Fab. The LY6.3-treated control femurs, marked with a circle, grew at the slowest rate. The MSPRO59 treated femurs exhibited a higher growth rate, with the optimal rate achieved at the highest MSPRO59 concentration of 400 ug/ml (square), which can be seen as the steeper slope. Moreover, the growth rates achieved by 400 microgram/ml of MSPRO59 doubled in comparison to the control Ab (3.55 U/day as compared to 1.88 U/day, respectively). This experiment shows the neutralizing effect of the MSPRO59 antibody on an ach mutant FGFR3, in an ex vivo model.

Example 13

In-vivo Trials

Figure 22:
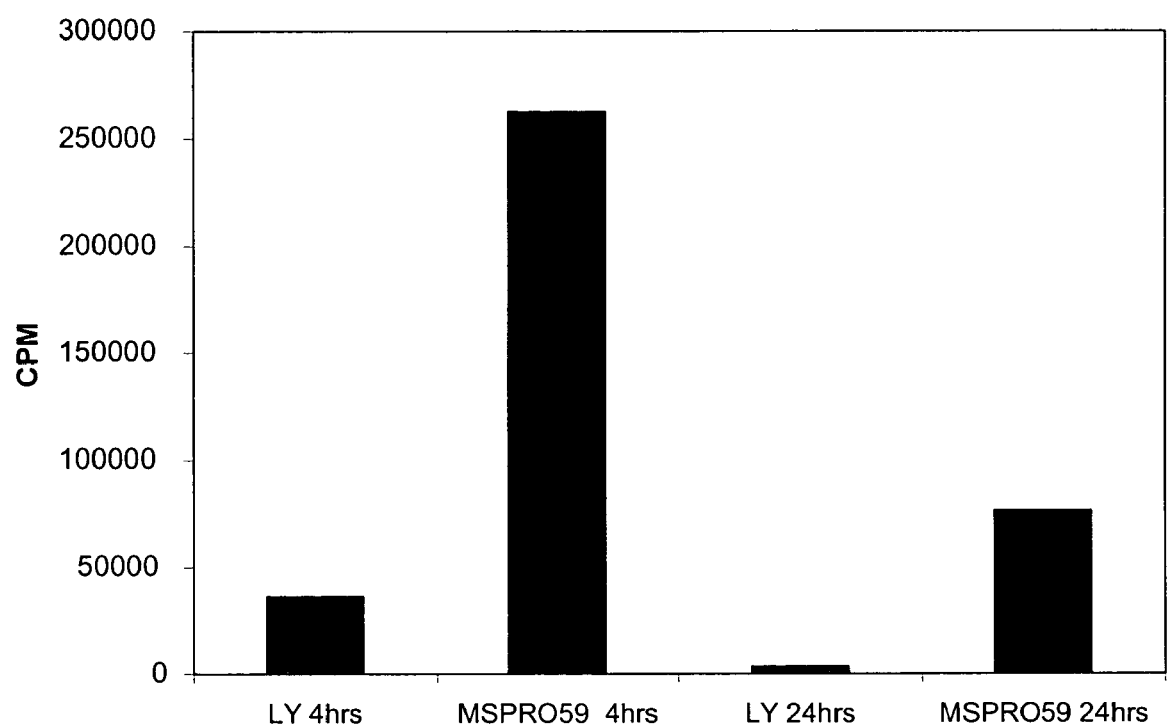
FIG. 22 shows $^{125}$I-MSPRO59 localization to the FDCP-FR3ach derived tumor.

FDCP-FR3ach cells, but not FDCP (control) cells, were found to be tumorigenic when injected into nude mice. Each of 9 mice received two sub-cutaneous injections with different amount of transfected cells. Fourteen days after injection, progressively growing tumors started to appear at the site of FDCP-FR3ach injection but not at the FDCP site of injection. External examination of the tumors showed a high vascular capsule. $^{125}$I-labeled MSPRO59 and LY6.3 were injected I.P. into nude mice carrying the FDCP-FR3ach derived tumor. The tumors were dissected 4 and 24 hours later and radioactivity was measured. Concentration of labeled MSPRO59 Abs in FDCP-FR3ach derived tumors is shown in FIG. 22.

Example 14

Animal Model for Bladder Carcinoma

Recent studies have shown that the IIIb isoform of FGFR3 is the only form expressed in bladder carcinoma, in particular an FGFR3 with an amino acid substitution wherein Serine 249 is replaced by Cysteine (S249C). The progression of the cancer is believed to be a result of the constitutive activation resulting from this amino acid substitution. In order to create the FGFR3 IIIb form, we isolated the IIIb region of FGFR3 from HeLa cells and generated a full length FFGR3IIIb isoform in pLXSN. Retroviruses, expressing either normal FGFR3 (FR3wt) or mutant FGFR3 (FR3-S249C) were produced and used to infect FDCP cells. Stable pools were generated and further used for in-vitro and in-vivo experiments.

MSPRO59 Reduces Tumor Size in Mice

Figure 23:
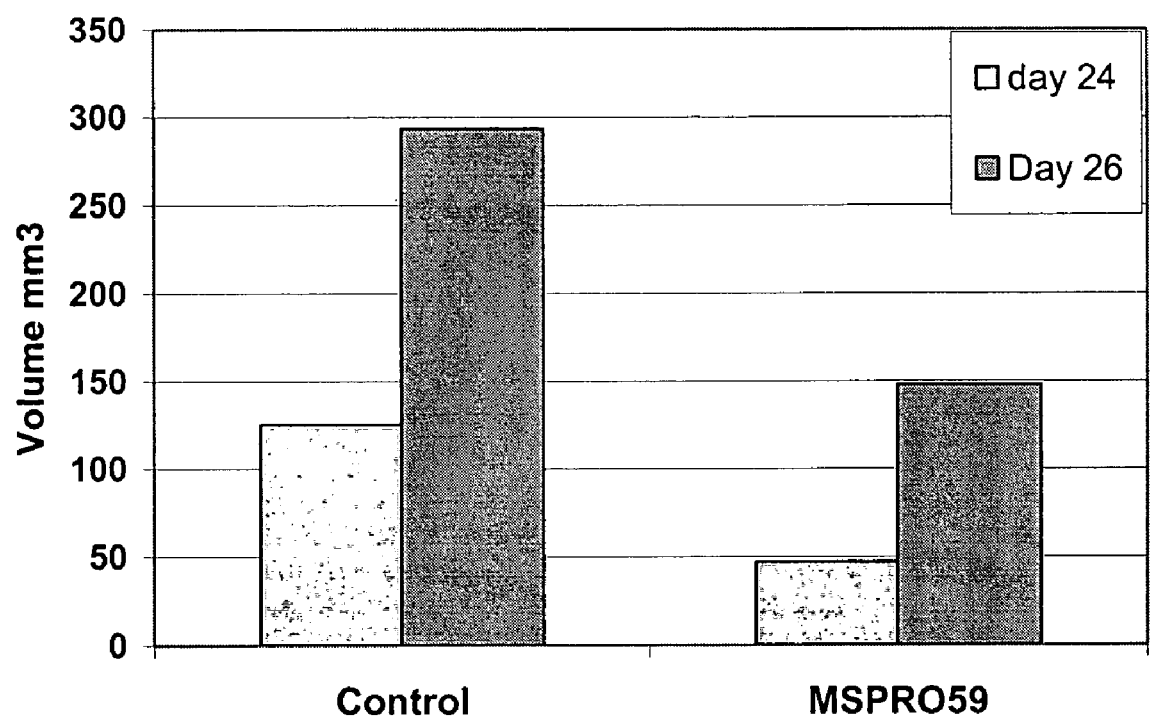
FIG. 23 shows the effect of MSPRO59 on inhibiting ligand-independent tumor growth.

Twelve nude mice were injected with $2 \times 10^6$ FDCP-S249C cells subcutaneous at 2 locations, one on each flank. A week later MSPRO59 was administered I.P. at 400 ug per mouse (3 mice in total), followed by 3 injections of 275 ug each, in 2 to 3 days intervals. Following 24 and 26 days the tumor size was measures. FIG. 23 shows the inhibitory effect of MSPRO59 on tumor size.

Treatment of FDCP-S249C-derived Tumors with MSPRO59

Figure 24:
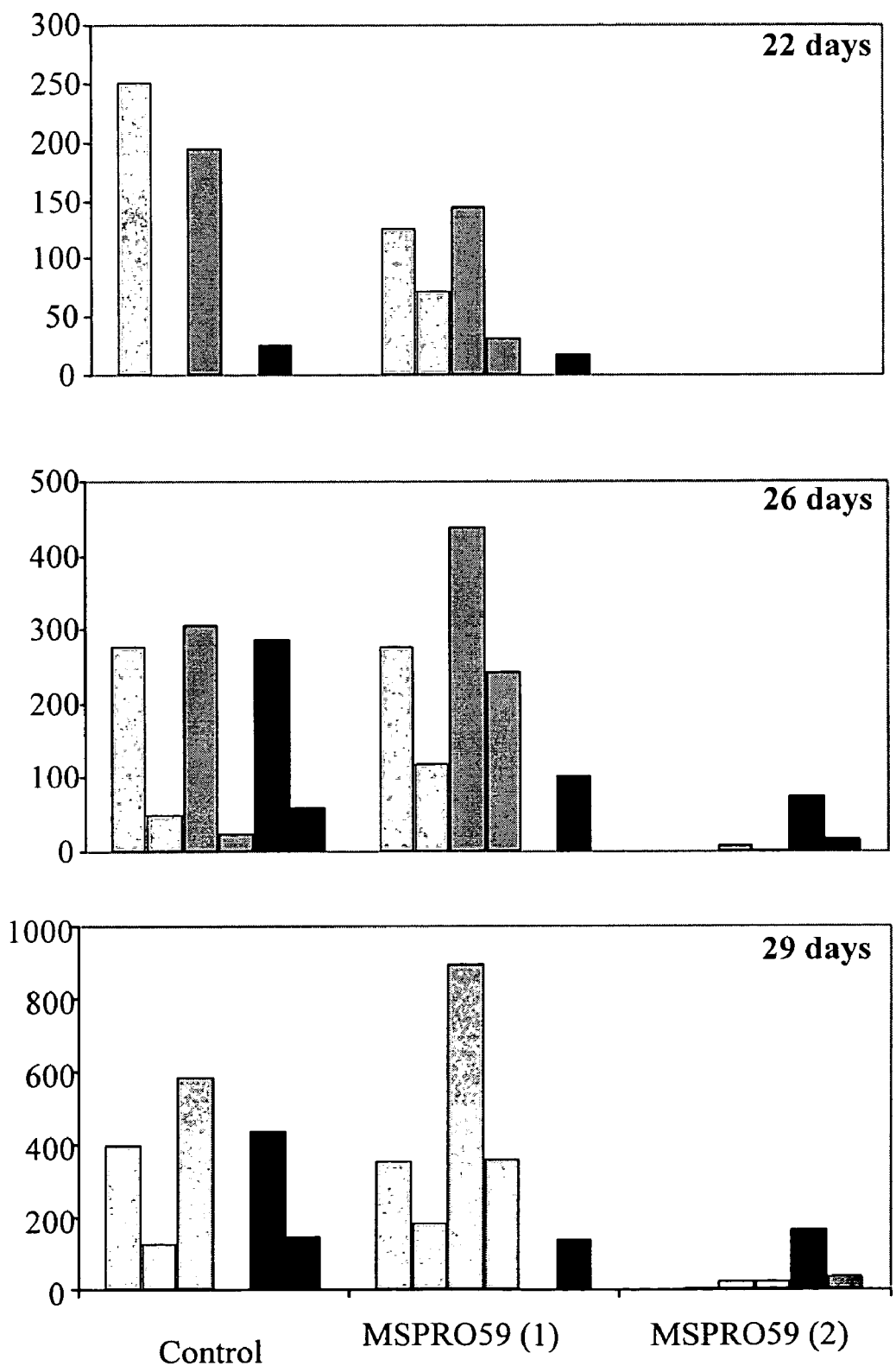
FIG. 24 shows the effect of MSPRO59 on inhibiting ligand-independent tumor growth.

Nude mice (3 in each group), were injected subcutaneous at 2 locations, one on each flank, with $2 \times 10^6$ FDCP-S249C cells each. A week later, 400 or 80 µg MSPRO59 were injected IP. Three days later, mice were injected with 400 µg followed by 5 additional injections with 275 µg MSPRO59, each, every 3 or 4 days. Mice initially treated with 80 µg MSPRO59 were similarly given an additional 80 µg MSPRO59 followed by 5 injections with 50 µg MSPRO59 at the same schedule. Mice injected with PBS were used as control. Tumor volume was estimated from measurements in 3 dimensions at 16, 20, 23 or 32 days post cell injection. As shown in FIG. 24 there is both a delay in tumor appearance and an inhibitory effect on tumor progression in the treated mice. This indicates that these FGFR3 inhibitors are potent in vivo.

These data may also help us understand the mechanism by which the S249C-derived tumors were developed. Since we are using pools of cells, treatment with MSPRO59 inhibited the susceptible cells, leading to delay in tumor appearance. However, over time, the resistant cells survived and proliferated, giving rise to a solid tumor.

MSPRO59 Inhibits FDCP-FR3ach380 Derived Tumor Growth.

Nude mice were injected subcutaneously in the flank with $2 \times 10^6$ FDCP-FR3ach380 cells, each. Treatment with MSPRO59 began at the day of tumor appearance. Three mice were treated with a known tyrosine kinase inhibitor (TKI –50 mg/Kg/injection) and three with 400 µg followed by 3 additional injections with 300 µg MSPRO59, every 3 or 4 days. Three mice were treated with PBS alone as control. The tumor size was estimated as before at the indicated days after cell injection. The dose schedule is shown in Table 8 below.

TABLE 8

| | Days After FDCP-FR3$^{ach380}$ Cell Injection | | | |
|---|---|---|---|---|
| | 21 | 25 | 28 | 31 |
| MSPRO59 (µg) | 400 µg | 300 µg | 300 µg | 300 µg |
| PBS (µl) | 50 | 50 | 50 | 50 |

Figure 25A:
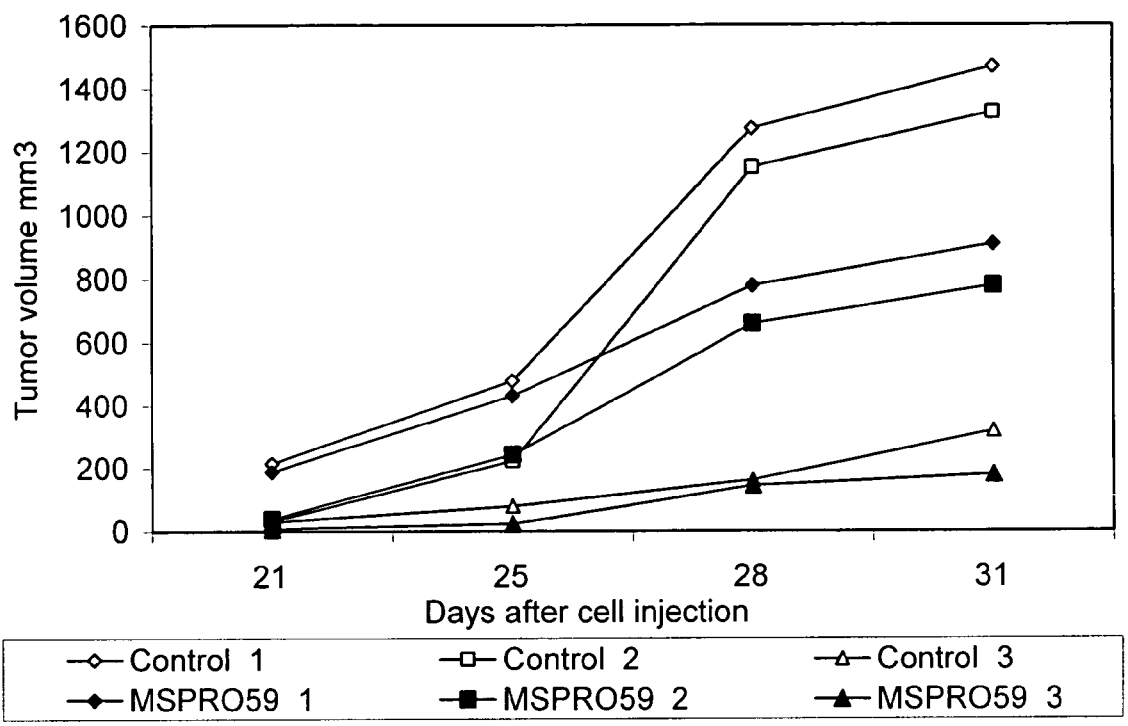
FIG. 25A shows the effect of MSPRO59 on inhibiting ligand-independent tumor growth.

Results are shown in bar graph format in FIG. 25A.

MSPRO59 Inhibits FDCP-S249C Induced Tumor Growth

After several months in culture FDCP-S249C cells acquire partial resistance to MSPRO antibodies and eventually become completely insensitive. To overcome the instability of the FDCP-derived pools, clones from a pool of FDCP-S249C cells were isolated and characterized. These clones were tested in an XTT proliferation assay and were shown to be inhibited by MSPRO59. $2 \times 10^6$ cells from each clone were injected into nude mice. Tumors appeared 18-30 after injection.

Figure 25B:
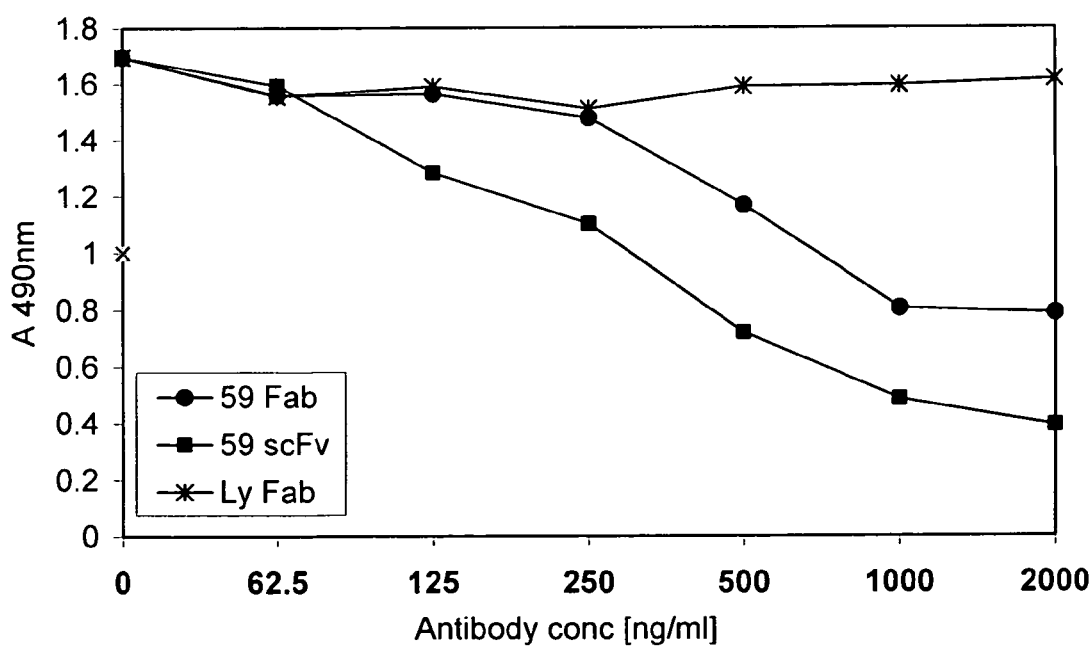
FIG. 25B shows scFv MSPRO59 blocking the proliferation of FDCP-FR3 (S375C) cells.
Figure 26:
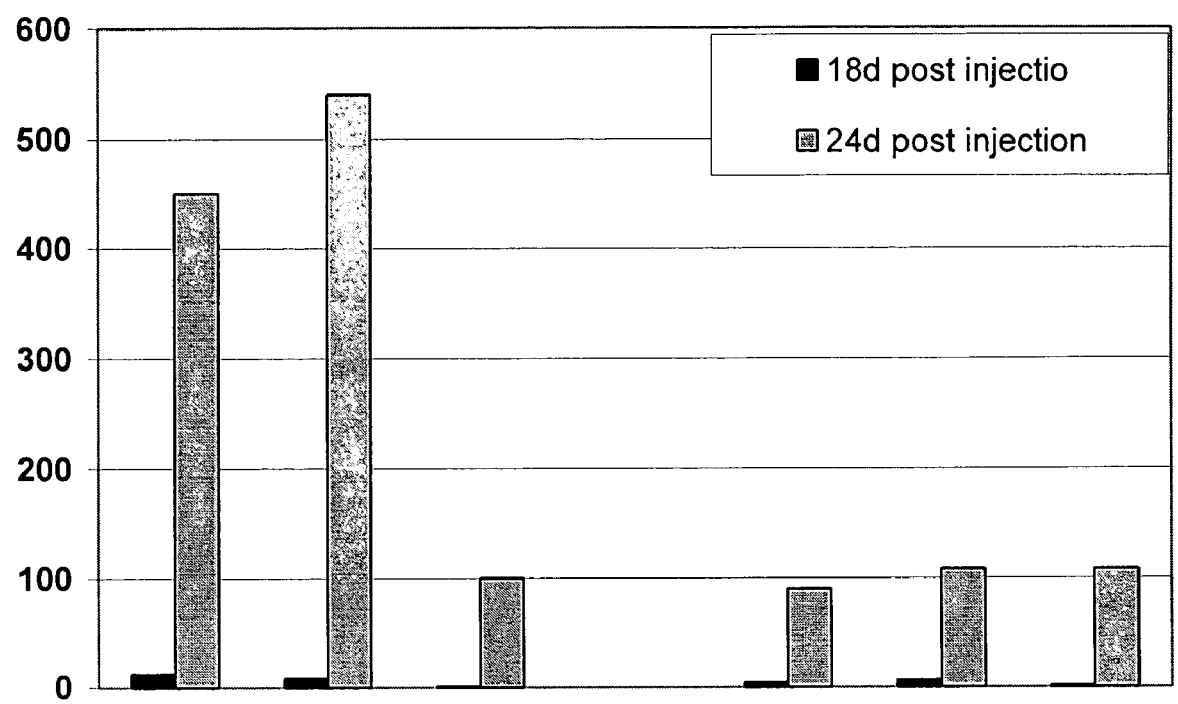
FIG. 26 shows the effect of MSPRO59 single chain antibody on inhibiting ligand-independent tumor growth.

FDCP-S249C clone cells were injected subcutaneously on the flank. A week later mice were injected with 280 µg MSPRO59 single chain (SC) I.P. every day. Mice injected with PBS were used as control. Tumor volume was estimated from measurements in 3 dimensions at 18 or 24 days post cell injection. An apparent inhibition of tumor growth by MSPRO59 (ScFv) was observed in tumors derived from clone 2 (FIG. 26). FIG. 25B shows the inhibition effected by MSPRO59scFv and MSPRO59 Fab compared to the control. Both inhibit growth of the tumor resulting from constitutively activated cells.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references. Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Ansel et al, *Pharmaceutical Dosage Forms and Drug Delivery Systems,* 5th Ed. (Lea & Febiger 1990)
Ausubel et al (Eds), *Current Protocols in Molecular Biology,* John Wiley & Sons, Inc. (New York) (1987-1999)

Bellus et al., *Nature Genetics*, 14:174-176 (1996)
Better et al, ", *Science* 240d(4855):1041-1043 (1988)
Blume-Jensen et al., *Nature* 411:355-365 (2001)
Boulianne et al, *Nature* 312(5995):643-646 (1984)
Burchiel et al., Chapter 13 in Tumor Imaging: The Radiochemical Detection of Cancer, Burchiel and Rhodes, eds., Masson Publishing Inc. (1982).
Cappellen et al., *Nature* Genetics, 23:18-20 (1999)
Chesi et al., *Blood*, 97(3):729-736 (2001)
Colligan et al (eds.), *Current Protocols in Immunology*, John Wiley & Sons, Inc. (New York) (1992-2000)
Frank, Opthalmic Res 29:341-53 (19997)
Galvin et al., *PNAS USA*, 93:7894-7899 (1996)
Gennaro (ed.), *Remington's Pharmaceutical Sciences*, 18th Ed. (Mack Publishing Co. 1990)
Gerwins et al., *Crit Rev Oncol Hematol* 34(3):185-94 (2000)
Grigoriadis et al, *J Cell Biol* 106(6):2139-51 (1988)
Harlow et al, *Antibodies: A Laboratory Manual*, CSHL (Cold Spring Harbor, N.Y.) (1988)
Knappik et al., *J. Mol. Biol.*, 296:57-86 (2000)
Kohfeldt et al., *FEBS Lett.* 414:557-561 (1997)
Kohler and Milstein, *Nature*, 256(5517):495-497 (1975)
Liu et al, PNAS *USA*. 84(10):3439-3443 (1987)
Martin, *Genes Dev.* 12:1571-1586 (1998)
Meinkoth et al, *Anal Biochem* 138:267-284 (1984)
Meyers et al., *Nature Genetics*, 11:462-464 (1995)
Morrison et al., *PNAS USA* 81(21):6851-6855 (1984)
Muenke et al., *Am. J. Hum. Genet.*, 60:555-564 (1997)
Neuberger et al, *Nature* 314(6008):268-270 (1985)
Ornitz et al, *J Biol Chem* 267:16305-16311 (1992)
Ornitz, *Novartis Found Symp* 232:63-76; discussion 76-80, 272-82 (2001)
Paques et al., *Diabetes Metab*, 23(2):125-30 (1997)
Queen et al., *PNAS USA*, 86:10029-10033 (1989)
Saito et al., *Mol Cell Biol*, 21(19):6387-94 (2001)
Sato et al., *Ann N Y Acad Sci*, 902:201-5; discussion 205-7 (2000)
Saltzman et al, *Biophys. J*, 55:163 (1989)
Sambrook, J., Fritsch, E. F. and Maniatis, T. (1989) Molecular Cloning: A laboratory manual, Cold Spring Harbor Laboratory Press, Cold Spring Harbor, USA.
Schell et al., Hum Mol Gen, 4:323-328 (1995)
Sherwood et al., *Biotechnology*, 10(11):1446-49 (1992)
Tavormina et al., Am. J. Hum. Genet., 64:722-731 (1999)
Vajo et al., *Endocrine Reviews*, 21(1):23-39 (2000)
Webster et al., *Trends Genetics* 13(5):178-182 (1997)
Yamaguchi et al., *EMBO J.* 18(16):4414-4423 (1999)

---

What is claimed is:

1. An isolated antibody or antigen-binding fragment thereof, wherein said antibody or said antigen-binding fragment thereof specifically binds the extracellular domain of the human fibroblast growth factor receptor 3 (FGFR3) polypeptide comprising the amino acid sequence of SEQ ID NO:1 and wherein said antibody or said antigen-binding fragment thereof comprises a heavy chain variable region comprising the amino acid sequence of SEQ ID NO:106 and a light chain variable region comprising the amino acid sequence of SEQ ID NO:95.

2. A composition comprising the antibody or antigen-binding fragment thereof according to claim 1.

3. A kit comprising the antibody or antigen-binding fragment thereof of claim 1.

4. An isolated antibody or antigen-binding fragment thereof, wherein said antibody or said antigen-binding fragment thereof specifically binds the extracellular domain of the human fibroblast growth factor receptor 3 (FGFR3) polypeptide comprising the amino acid sequence of SEQ ID NO:1 and wherein said antibody or said antigen-binding fragment thereof comprises a heavy chain variable region comprising the 3 complementarity determining region (CDR) amino acid sequences of the heavy chain variable region amino acid sequence of SEQ ID NO:106 and a light chain variable region comprising the 3 CDR amino acid sequences of the light chain variable region amino acid sequence of SEQ ID NO:95.

5. A composition comprising the antibody or antigen-binding fragment thereof according to claim 4.

6. A kit comprising the antibody or antigen-binding fragment thereof of claim 4.

* * * * *

UNITED STATES PATENT AND TRADEMARK OFFICE
CERTIFICATE OF CORRECTION

PATENT NO. : 7,498,416 B2
APPLICATION NO. : 10/734661
DATED : March 3, 2009
INVENTOR(S) : Yayon et al.

It is certified that error appears in the above-identified patent and that said Letters Patent is hereby corrected as shown below:

Column 34
Line 24, after "overnight at", delete "40°C" and insert -- 4°C --.

Column 38
Line 41, after "4 hour at", delete "40°C" and insert -- 4°C --.

Signed and Sealed this

Nineteenth Day of May, 2009

JOHN DOLL
*Acting Director of the United States Patent and Trademark Office*